(12) United States Patent
Tadokoro et al.

(10) Patent No.: US 10,527,940 B2
(45) Date of Patent: Jan. 7, 2020

(54) PHOTOSENSITIVE RESIN COMPOSITION, POLYAMIDE RESIN, METHOD FOR PRODUCING POLYAMIDE RESIN, COMPOUND, METHOD FOR PRODUCING COMPOUND, METHOD FOR PRODUCING CURED FILM, AND CURED FILM

(71) Applicant: TOKYO OHKA KOGYO CO., LTD., Kawasaki-shi (JP)

(72) Inventors: Yoshinori Tadokoro, Kawasaki (JP); Dai Shiota, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 114 days.

(21) Appl. No.: 15/699,292

(22) Filed: Sep. 8, 2017

(65) Prior Publication Data
US 2018/0107114 A1 Apr. 19, 2018
US 2019/0332012 A9 Oct. 31, 2019

(30) Foreign Application Priority Data

Sep. 13, 2016 (JP) .................. 2016-179000
Aug. 4, 2017 (JP) .................. 2017-151972

(51) Int. Cl.
| | | |
|---|---|---|
| *G03F 7/038* | (2006.01) | |
| *C07C 67/08* | (2006.01) | |
| *C09D 179/08* | (2006.01) | |
| *C08G 73/14* | (2006.01) | |
| *C08G 73/10* | (2006.01) | |
| *G03F 7/037* | (2006.01) | |
| *C07C 62/38* | (2006.01) | |
| *C07C 69/757* | (2006.01) | |
| *C07D 493/10* | (2006.01) | |
| *C08G 69/26* | (2006.01) | |
| *C08G 69/28* | (2006.01) | |
| *G03F 7/16* | (2006.01) | |
| *G03F 7/20* | (2006.01) | |
| *G03F 7/30* | (2006.01) | |

(52) U.S. Cl.
CPC ............ *G03F 7/0387* (2013.01); *C07C 62/38* (2013.01); *C07C 67/08* (2013.01); *C07C 69/757* (2013.01); *C07D 493/10* (2013.01); *C08G 69/26* (2013.01); *C08G 69/28* (2013.01); *C08G 73/1078* (2013.01); *C08G 73/14* (2013.01); *C09D 179/08* (2013.01); *G03F 7/037* (2013.01); *G03F 7/0388* (2013.01); *C07C 2603/94* (2017.05); *G03F 7/16* (2013.01); *G03F 7/20* (2013.01); *G03F 7/30* (2013.01)

(58) Field of Classification Search
CPC ...... C07C 69/757; C08G 69/26; G03F 7/0387; C07D 307/93
See application file for complete search history.

(56) References Cited

U.S. PATENT DOCUMENTS

| | | | |
|---|---|---|---|
| 4,450,273 A | 5/1984 | Graser | |
| 4,725,690 A | 2/1988 | Graser | |
| 6,503,937 B1 | 1/2003 | Nesvadba et al. | |
| 8,451,401 B2 | 5/2013 | Kawana et al. | |
| 8,629,303 B2 * | 1/2014 | Komatsu | C07C 49/643 568/351 |
| 9,399,703 B2 | 7/2016 | Komatsu et al. | |
| 2009/0322990 A1 | 12/2009 | Kawana et al. | |
| 2011/0049444 A1 | 3/2011 | Sako et al. | |
| 2013/0079490 A1 | 3/2013 | Matsumoto et al. | |
| 2015/0086753 A1 * | 3/2015 | Matsumoto | C09D 179/08 428/195.1 |
| 2015/0218317 A1 | 8/2015 | Komatsu et al. | |

FOREIGN PATENT DOCUMENTS

| | | |
|---|---|---|
| JP | S62-001753 A | 1/1987 |
| JP | S63-026784 B2 | 5/1988 |
| JP | 2011-038085 A | 2/2011 |
| JP | 2013-137543 A | 7/2013 |
| JP | 2013-225132 A | 10/2013 |
| JP | 2014-178477 A | 9/2014 |
| JP | 2014-197206 A | 10/2014 |
| WO | WO 00/24736 A1 | 5/2000 |
| WO | WO 2010/081624 A1 | 7/2010 |
| WO | WO 2011/099518 A1 | 8/2011 |
| WO | WO 2013/168675 A1 | 11/2013 |
| WO | WO 2014/034760 A1 | 3/2014 |

* cited by examiner

*Primary Examiner* — Cynthia Hamilton

(57) ABSTRACT

A photosensitive resin composition capable of forming a cured film with satisfactory adhesion to substrates and excellent transparency, a polyamide resin which is used in the photosensitive resin composition, a method for producing the polyamide resin, a compound which is used as a raw material of the polyamide resin, a method for producing the compound, a method for producing a cured film using the photosensitive resin composition, and a cured film which is obtained by curing the photosensitive resin composition. The photosensitive resin composition including a resin and a photopolymerization initiator. The resin is a polyamide resin including a structural unit, which includes a specific saturated alicyclic skeleton, and at least one carboxy group esterified by a unit containing a polymerizable group of a predetermined structure.

13 Claims, No Drawings

PHOTOSENSITIVE RESIN COMPOSITION, POLYAMIDE RESIN, METHOD FOR PRODUCING POLYAMIDE RESIN, COMPOUND, METHOD FOR PRODUCING COMPOUND, METHOD FOR PRODUCING CURED FILM, AND CURED FILM

RELATED APPLICATIONS

This application claims priority to Japanese Patent Application No. 2016-179000, filed Oct. 13, 2016 and Japanese Patent Application No. 2007-151972, filed Aug. 4, 2017, the entire contents of which are incorporated herein by reference.

BACKGROUND OF THE INVENTION

Field of the Invention

The present invention relates to a photosensitive resin composition containing a polyamide resin including an alicyclic skeleton of a specific structure, the polyamide resin, a method for producing the polyamide resin, a compound which is suitably used as a raw material of the polyamide resin, a method for producing the compound, a method for producing a cured film using the photosensitive resin composition, and a cured film which is obtained by curing the photosensitive resin composition.

Related Art

Polyamide resins, polyimide resins, and the like which are excellent in heat resistance, electrical properties, and mechanical properties have widely been used as materials of insulation films in various electronic parts, passivation films, surface protection films, and interlayer insulation films in semiconductor devices, and the like. Insulation films in electronic parts, passivation films, surface protection films, and interlayer insulation films in semiconductor devices, and the like are often formed to have accurate dimensions in a microscopic region. Therefore, a photosensitive composition containing a polyamide resin, a polyimide resin or a polyimide resin precursor, which facilitates accurate formation of a resin film with a predetermined size at a predetermined position by exposure and development, have often been used.

As the photosensitive composition, for example, a photosensitive composition has been proposed wherein the composition contains a polyamide resin which has a chemical structure of a polyamic acid ester of a predetermined structure and also contains two groups in a specific ratio as ester-bonded organic groups, namely a hydrocarbon group having 5 or more carbon atoms and a polymerizable functional group of a predetermined structure, such as a (meth) acryloyloxyethyl group (see Patent Document 1). According to Patent Document 1, a resin film patterned using this photosensitive composition is formed and then the resin film is heated, thus making it possible to form a cured film with a higher Young's modulus.

Patent Document 1: Pamphlet of PCT International Publication No. WO2013/168675

SUMMARY OF THE INVENTION

However, when using the photosensitive composition disclosed in Patent Document 1, the patterned resin film to be formed after exposure and development may not always exhibit satisfactory adhesion to substrates. Moreover, when an insulation film is formed using the photosensitive composition, the film is required to be transparent depending on the applications of the electronic parts and semiconductor devices. In this regard, even when using the photosensitive composition mentioned in Patent Document 1, it has become clear that there still remains room for improvement from the viewpoint of formation of transparent resin films.

The present invention has been made in light of the problems mentioned above, and an object thereof is to provide a photosensitive resin composition capable of forming a cured film with satisfactory adhesion to substrates and excellent transparency, a polyamide resin which is suitably used in the photosensitive resin composition, a method for producing the polyamide resin, a compound which is suitably used as a raw material of the polyamide resin, a method for producing the compound, a method for producing a cured film using the photosensitive resin composition, and a cured film which is obtained by curing the photosensitive resin composition.

The present inventors have found that the problems mentioned above can be solved by using, as the resin (A) of a photosensitive resin composition including a resin (A) and a photopolymerization initiator (B), a polyamide resin including a structural unit wherein a specific saturated alicyclic skeleton is included and at least one of the carboxy group is esterified by a unit containing a polymerizable group of a predetermined structure, and thus the present invention has been completed. More specifically, the present invention provides the followings.

A first aspect of the present invention is directed to a photosensitive resin composition including a resin (A) and a photopolymerization initiator (B), wherein the resin (A) includes a polyamide resin including a structural unit represented by the following formula (a1):

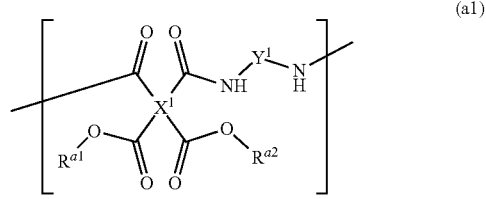

wherein, in the formula (a1), $X^1$ is a tetravalent group represented by the following formula (a2):

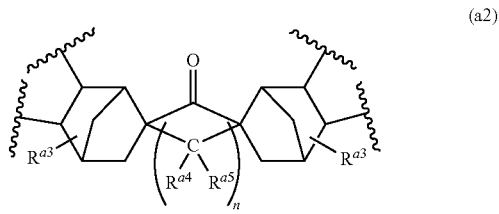

$Y^1$ is a divalent organic group, $R^{a1}$ and $R^{a2}$ each independently represent a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

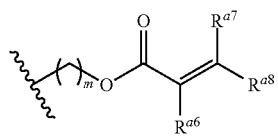

at least one of $R^{a1}$ and $R^{a2}$ is a group represented by the above formula (a3), in the formula (a2), $R^{a3}$, $R^{a4}$, and $R^{a5}$ each independently represent one selected from the group consisting of a hydrogen atom, an alkyl group having 1 or more and 10 or less carbon atoms, and a fluorine atom, n is an integer of 0 or more and 12 or less, in the formula (a3), $R^{a6}$, $R^{a7}$, and $R^{a8}$ each independently represent a hydrogen atom or an organic group having 1 or more and 3 or less carbon atoms, and m is an integer of 2 or more and 10 or less.

A second aspect of the present invention is directed to a polyamide resin including a structural unit represented by the following formula (a1):

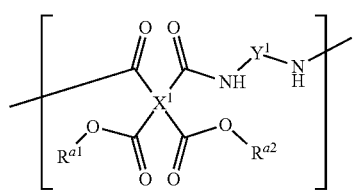

wherein, in the formula (a1), $X^1$ is a tetravalent group represented by the following formula (a2):

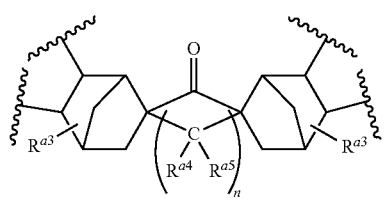

$Y^1$ is a divalent organic group, $R^{a1}$ and $R^{a2}$ each independently represent a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

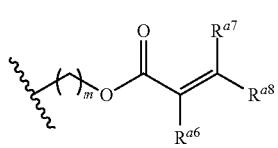

at least one of $R^{a1}$ and $R^{a2}$ is a group represented by the formula (a3), in the formula (a2), $R^{a3}$, $R^{a4}$, and $R^{a5}$ each independently represent one selected from the group consisting of a hydrogen atom, an alkyl group having 1 or more and 10 or less carbon atoms, and a fluorine atom, n is an integer of 0 or more and 12 or less, in the formula (a3), $R^{a6}$, $R^{a7}$, and $R^{a8}$ each independently represent a hydrogen atom or an organic group having 1 or more and 3 or less carbon atoms, m is an integer of 2 or more and 10 or less, and when at least one of $R^{a1}$ and $R^{a2}$ is a hydrogen atom, a carboxy group represented by —COOR$^{a1}$ or —COOR$^{a2}$ may form an acid halide or may form a salt.

A third aspect of the present invention is directed to a method for producing the polyamide resin according to the second aspect, the method including condensing a polyvalent carboxylic acid compound represented by the following formula (I):

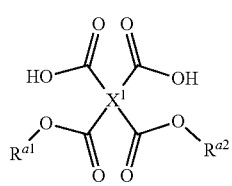

wherein, in the formula (I), $X^1$ is a tetravalent group represented by the following formula (a2):

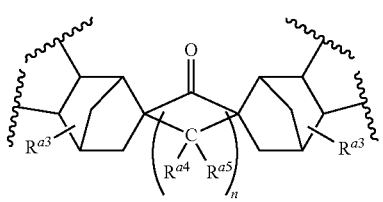

$R^{a1}$ and $R^{a2}$ each independently represent a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

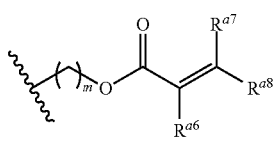

at least one of $R^{a1}$ and $R^{a2}$ is a group represented by the formula (a3), in the formula (a2), $R^{a3}$, $R^{a4}$, and $R^{a5}$ each independently represent one selected from the group consisting of a hydrogen atom, an alkyl group having 1 or more and 10 or less carbon atoms, and a fluorine atom, n is an integer of 0 or more and 12 or less, in the formula (a3), $R^{a6}$, $R^{a7}$, and $R^{a8}$ each independently represent a hydrogen atom or an organic group having 1 or more and 3 or less carbon atoms, and m is an integer of 2 or more and 10 or less, and/or an acid halide of the polyvalent carboxylic acid compound, with a diamine compound represented by the following formula (II):

$$H_2N-Y^1-NH_2 \quad (II)$$

wherein, in the formula (II), $Y^1$ is a divalent organic group.

A fourth aspect of the present invention is directed to a compound represented by the following formula (I):

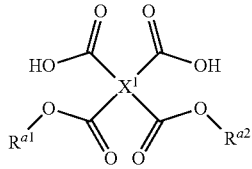
(I)

wherein, in the formula (I), $X^1$ is a tetravalent group represented by the following formula (a2):

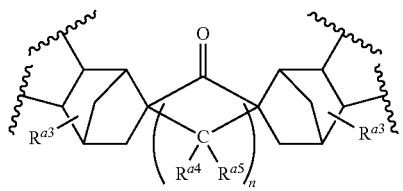
(a2)

$R^{a1}$ and $R^{a2}$ each independently represent a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

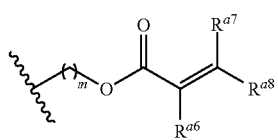
(a3)

at least one of $R^{a1}$ and $R^{a2}$ is a group represented by the formula (a3), in the formula (a2), $R^{a3}$, $R^{a4}$, and $R^{a5}$ each independently represent one selected from the group consisting of a hydrogen atom, an alkyl group having 1 or more and 10 or less carbon atoms, and a fluorine atom, n is an integer of 0 or more and 12 or less, in the formula (a3), $R^{a6}$, $R^{a7}$, and $R^{a8}$ each independently represent a hydrogen atom or an organic group having 1 or more and 3 or less carbon atoms, and m is an integer of 2 or more and 10 or less, wherein a carboxy group contained in the compound may form an acid halide, or may form a salt.

A fifth aspect of the present invention is directed to a method for producing the compound according to the fourth aspect, the method including reacting a tetracarboxylic dianhydride represented by the following formula (a4):

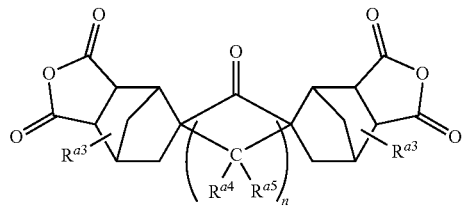
(a4)

wherein, in the formula (a4), $R^{a3}$, $R^{a4}$, and $R^{a5}$ each independently represent one selected from the group consisting of a hydrogen atom, an alkyl group having 1 or more and 10 or less carbon atoms, and a fluorine atom, n is an integer of 0 or more and 12 or less, with an unsaturated carboxylic acid ester represented by the following formula (a5):

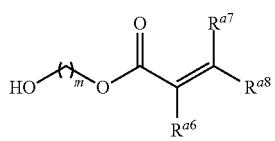
(a5)

wherein, in the formula (a5), $R^{a6}$, $R^{a7}$, and $R^{a8}$ each independently represent a hydrogen atom or an organic group having 1 or more and 3 or less carbon atoms, and m is an integer of 2 or more and 10 or less.

A sixth aspect of the present invention is directed to a method for producing a cured film, the method including: applying the photosensitive resin composition according to the first aspect to form a coating film; and exposing the coating film.

A seventh aspect of the present invention is directed to a cured film which is obtained by curing the photosensitive resin composition according to the first aspect.

According to the present invention, it is possible to provide a photosensitive resin composition capable of forming a cured film with satisfactory adhesion to substrates and excellent transparence, a polyamide resin which is suitably used in the photosensitive resin composition, a method for producing the polyamide resin, a compound which is suitably used as a raw material of the polyamide resin, a method for producing the compound, a method for producing a cured film using the photosensitive resin composition, and a cured film which is obtained by curing the photosensitive resin composition.

DETAILED DESCRIPTION OF THE INVENTION

The present invention will be described below by way of preferred embodiments. "To" as used herein means a range between the lower limit and the upper limit inclusive, unless otherwise specified.

<<Photosensitive Resin Composition>>

Hereinafter, the photosensitive resin composition according to the first aspect of the present invention will be described. The photosensitive resin composition according to the first aspect includes a resin (A) and a photopolymerization initiator (B). The photosensitive resin composition can form a cured film, which satisfactorily adheres to substrates and is excellent in transparency, by including a combination of a resin (A) containing a polyamide resin having a structure described later, and a photopolymerization initiator (B). Hereinafter, essential or optional components included in the photosensitive resin composition will be described.

<Resin (A)>

The resin (A) contains a polyamide resin including a structural unit represented by the following formula (a1):

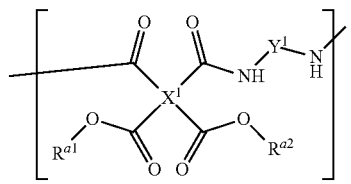
(a1)

wherein, in the formula (a1), $X^1$ is a tetravalent group represented by the following formula (a2):

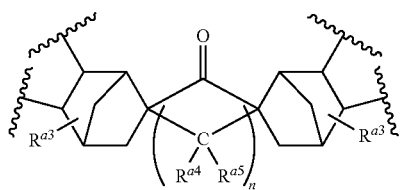
(a2)

$Y^1$ is a divalent organic group,
$R^{a1}$ and $R^{a2}$ each independently represent a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

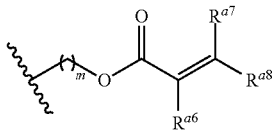
(a3)

at least one of $R^{a1}$ and $R^{a2}$ is a group represented by the formula (a3),
in the formula (a2), $R^{a3}$, $R^{a4}$, and $R^{a5}$ each independently represent one selected from the group consisting of a hydrogen atom, an alkyl group having 1 or more and 10 or less carbon atoms, and a fluorine atom,
n is an integer of 0 or more and 12 or less,
in the formula (a3), $R^{a6}$, $R^{a7}$, and $R^{a7}$ each independently represent a hydrogen atom or an organic group having 1 or more and 3 or less carbon atoms, and
m is an integer of 2 or more and 10 or less.

The polyamide resin contained in the resin (A) essentially contains the group represented by the formula (a3). Therefore, it is possible to form a cured film with excellent transparency by exposing the photosensitive resin composition. Moreover, the photosensitive resin composition essentially includes the photopolymerization initiator (B) mentioned later. Therefore, when the photosensitive resin composition is exposed, crosslinking between groups represented by the formula (a3) occurs between the molecules of the polyamide resin, leading to the curing of the photosensitive resin composition. When a cured film is formed using the photosensitive resin composition, crosslinking occurs between the molecules of the polyamide resin of the predetermined structure, thus making it possible to form a cured film which satisfactorily adheres to substrates.

[Polyamide Resin]

As mentioned above, the polyamide resin is not particularly limited as long as it is a polyamide resin including the structural unit represented by the formula (a1). The molecule of the polyamide resin may include bonds other than amide bonds (—CO—NH—), such as ester bonds, carbonate bonds, urethane bonds, ether bonds, sulfone bonds (—SO$_2$—), and imide bonds. Therefore, the polyamide resin including a structural unit represented by the formula (a1) is sometimes a resin which is generally called a polyesteramide resin, a polyetheramide resin, or the like. In the description and claims of the present application, a resin containing the molecule including the above-mentioned bonds other than the amide bond in addition to an amide bond will be conveniently mentioned as "polyamide resin".

The polyamide resin is not limited to a resin composed only of a straight-chain molecule, and may have a branched chain in the molecule, or may include a network molecule. When the polyamide resin includes a network molecule, the network molecule preferably includes a trivalent structural unit represented by either of the following formulas (a1-1) or (a1-2).

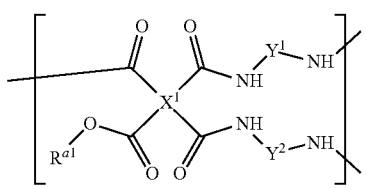
(a1-1)

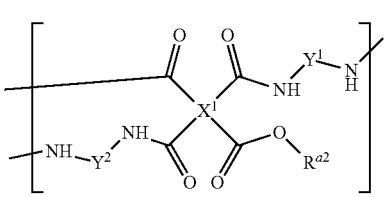
(a1-2)

In the formula (a1-1) and the formula (a1-2), $Y^2$ is a divalent organic group. Suitable examples of $Y^2$ are the same as those of $Y^1$ mentioned later. A bond which is bonded to an amino group (—NH—) possessed by a structural unit represented by the formula (a1-1) or the formula (a1-2) is bonded to a bond which is bonded to a carbonyl group (—CO—) contained in other structural units.

The content of the unit represented by the formula (a1) in the polyamide resin is not particularly limited as long as it does not interfere with the object of the present invention. The content of the unit represented by the formula (a1) in the polyamide resin is preferably 70% by mass or more, more preferably 80% by mass or more, particularly preferably 90% by mass or more, and most preferably 100% by mass, based on the total mass of the polyamide resin, since the photocurability of the photosensitive resin composition and the transparency of a cured film formed by using the photosensitive resin composition become satisfactory.

In the structural unit represented by the formula (a1), $R^{a1}$ and $R^{a2}$ each independently represent a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the formula (a3). The saturated aliphatic hydrocarbon group having 1 or more and 20 or less carbon atoms may be a straight-chain or branched-chain alkyl group, or may be a saturated aliphatic cyclic group, or may be a group composed of a combination of a saturated aliphatic cyclic group and an alkyl group or an alkylene group. When the saturated aliphatic hydrocarbon group is an alkyl group, the number of carbon atoms is preferably 1 or more and 10 or less, more preferably 1 or more and 8 or less, still more preferably 1 or more and 6 or less, and most preferably 1 or more and 4 or less. When the saturated aliphatic hydrocarbon group is a saturated aliphatic cyclic group, the number of carbon atoms is preferably 3 or more and 12 or less, and more preferably 4 or more and 10 or less. The number of carbon atoms of the aryl group is preferably 6 or more and 12 or less, and more preferably 6 or more and 10 or less. The number of carbon atoms of the aralkyl group is preferably 7 or more and 13 or less, and more preferably 7 or more and 11 or less. In the saturated aliphatic hydrocarbon group, the aryl group, and the aralkyl group in $R^{a1}$ and $R^{a2}$ in the structural unit represented by the formula (a1), as long as the number of carbon atoms satisfies the value mentioned above, heteroatoms such as nitrogen atoms (N), oxygen atoms (O), sulfur atoms (S), silicon atoms (Si), and selenium atoms (Se) may exist in addition to carbon atoms.

When $R^{a1}$ and $R^{a2}$ are alkyl groups, suitable examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a sec-pentyl group, a tert-pentyl group, an n-hexyl group, an n-heptyl group, an n-octyl group, a 2-ethylhexyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-icosyl group. Among these, a methyl group, an ethyl group, an n-propyl group, an isopropyl group, an n-butyl group, an isobutyl group, a sec-butyl group, and a tert-butyl group are preferable, and a methyl group, an ethyl group, an n-propyl group, and an isopropyl group are more preferable.

When $R^{a1}$ and $R^{a2}$ are saturated aliphatic cyclic groups, specific examples thereof include groups in which one hydrogen atom is eliminated from monocycloalkane or polycycloalkane such as bicycloalkane, tricycloalkane, or tetracycloalkane. Specific examples thereof include groups in which one hydrogen atom is eliminated from monocycloalkane such as cyclopentane, cyclohexane, cycloheptane, or cyclooctane, or polycycloalkane such as adamantane, norbornane, isobornane, tricyclodecane, or tetracyclododecane.

When $R^{a1}$ and $R^{a2}$ are aryl groups, specific examples thereof include a phenyl group, an α-naphthyl group, a β-naphthyl group, a biphenyl-4-yl group, a biphenyl-3-yl group, a biphenyl-2-yl group, a anthracen-1-yl group, a anthracen-2-yl group, an anthracene-9-yl group, a phenanthren-1-yl group, a phenanthren-2-yl group, a phenanthren-3-yl group, a phenanthren-4-yl group, and a phenanthren-9-yl group. Among these, a phenyl group, an α-naphthyl group, a β-naphthyl group, a biphenyl-4-yl group, a biphenyl-3-yl group, and a biphenyl-2-yl group are preferable, and a phenyl group is more preferable.

When $R^{a1}$ and $R^{a2}$ are aralkyl groups, specific examples thereof include a benzyl group, a phenethyl group, a 3-phenyl n-propyl group, a 4-phenyl n-propyl group, an α-naphthylmethyl group, a β-naphthylmethyl group, a 2-α-naphthylethyl group, and a 2-β-naphthylethyl group. Among these, a benzyl group and a phenethyl group are preferable, and a benzyl group is more preferable.

$R^{a6}$ in the formula (a3) is not particularly limited as long as it is a hydrogen atom or a monovalent organic group having 1 or more and 3 or less carbon atoms, but is preferably a hydrogen atom or a methyl group from the viewpoint of the photosensitive properties of the photosensitive resin composition. $R^{a7}$ and $R^{a8}$ in the formula (a3) are not particularly limited as long as each of them independently represent a hydrogen atom or a monovalent organic group having 1 or more and 3 or less carbon atoms, but are preferably hydrogen atoms from the viewpoint of the photosensitive properties of the photosensitive resin composition. m in the formula (a3) is an integer of 2 or more and 10 or less, and preferably an integer of 2 or more and 4 or less, from the viewpoint of the photosensitive properties. Typically, the group represented by the formula (a3) is preferably an acryloyloxyethyl group, a methacryloyloxyethyl group, a 3-acryloyloxy n-propyl group, a 3-methacryloyloxy n-propyl group, a 4-acryloyloxy n-butyl group, and a 4-methacryloyloxy n-butyl group.

In cases where $R^{a1}$ and $R^{a2}$ are saturated aliphatic hydrocarbon groups having 1 or more and 20 or less carbon atoms, aryl groups having 6 or more and 20 or less carbon atoms, aralkyl groups having 7 or more and 20 or less carbon atoms, or groups represented by the formula (a3), when subjecting a coating film made of a photosensitive resin composition to regioselective exposure and then developing the composition using an organic solvent as a developing solution, the solubility of the unexposed area in the developing solution is particularly satisfactory.

An alkyl group which can be selected as $R^{a3}$ in the formula (a2) is an alkyl group having 1 or more and 10 or less carbon atoms. When the number of carbon atoms of the alkyl group which can be selected as $R^{a3}$ is within a range of 1 or more and 10 or less, it is easy to form a cured film with satisfactory heat resistance. When $R^{a3}$ is an alkyl group, the number of carbon atoms is preferably 1 or more and 6 or less, more preferably 1 or more and 5 or less, still more preferably 1 or more and 4 or less, and particularly preferably 1 or more and 3 or less, since it becomes easier to form a cured film with satisfactory heat resistance. When $R^{a3}$ is an alkyl group, the alkyl group may be a straight-chain or branched-chain group.

Regarding the $R^{a3}$s in the formula (a2), it is more preferable that each of these are independently either a hydrogen atom or an alkyl group having 1 or more and 10 or less carbon atoms, since the heat resistance of the cured film formed using the photosensitive resin composition becomes excellent. Since the raw material compound for forming the structural unit represented by the formula (a1) can be made available and purified easily, $R^{a3}$ in the formula (a2) is more preferably a hydrogen atom, a methyl group, an ethyl group, an n-propyl group, or an isopropyl group, and particularly preferably a hydrogen atom or a methyl group. Plural $R^{a3}$s in the formula (a2) are preferably the same groups. Moreover, regarding the cured film to be produced, from the viewpoint of imparting water repellency, using a fluorine atom as $R^{a3}$ is also an example of a preferred aspect.

n in the formula (a2) represents an integer of 0 or more and 12 or less. When n is an integer of 0 or more and 12 or less, it is easy to purify the raw material compound which imparts the structure represented by the formula (a1), and the raw material compound becomes excellent in its chemical stability. Since the purification of a raw material compound for imparting a structure represented by the formula (a1) becomes easier, n is preferably 5 or less, and more preferably 3 or less. Since the chemical stability of the raw material compound which imparts the structure represented by the formula (a1) becomes excellent, n is preferably 1 or more, and more preferably 2 or more. n in the formula (a2) is particularly preferably 2 or 3.

An alkyl group having 1 or more and 10 or less carbon atoms, which can be selected as $R^{a4}$ and $R^{a5}$ in the formula (a2), is the same as an alkyl group having 1 or more and 10 or less carbon atoms which can be selected as $R^{a3}$. $R^{a4}$ and $R^{a5}$ preferably represent a hydrogen atom or an alkyl group having 1 or more and 10 or less carbon atoms (preferably 1 or more and 6 or less, more preferably 1 or more and 5 or less, still more preferably 1 or more and 4 or less, and particularly preferably 1 or more and 3 or less carbon atoms), and particularly preferably a hydrogen atom or a methyl group, since the purification of the raw material compound which imparts the structure represented by the formula (a1) becomes easier.

In a structural unit represented by the formula (a1), $Y^1$ is a divalent organic group. It is possible to employ, as $Y^1$, for example, a divalent organic group having 6 or more and 40 or less carbon atoms. When the number of carbon atoms of $Y^1$ is in the above range, it is easy to form a cured film with excellent heat resistance using the photosensitive resin composition, and the developability during the formation of the cured film is satisfactory. It is possible to employ, as the divalent organic group having 6 or more and 40 or less carbon atoms, an organic group having 1 or more and 4 or less aromatic rings or aliphatic rings.

When $Y^1$ is an organic group having 1 or more and 4 or less aromatic rings or aliphatic rings, the organic group is preferably an organic group having aromatic rings. The organic group having an aromatic ring is preferably at least one of the groups represented by the following formulas (1) to (4) from the viewpoint of the balance between the heat resistance of the cured film formed using the photosensitive resin composition and the solubility of the unexposed photosensitive resin composition in an organic solvent:

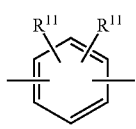

(1)

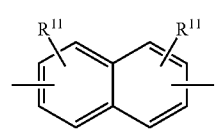

(2)

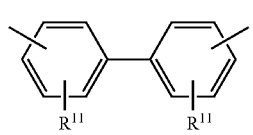

(3)

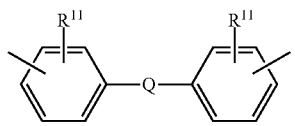

(4)

In the formula (4), $R^{11}$ represents one selected from the group consisting of a hydrogen atom, a fluorine atom, hydroxyl group, an alkyl group having 1 or more and 4 or less carbon atoms, and a halogenated alkyl group having 1 or more and 4 or less carbon atoms. In the formula (4), Q represents a 9,9'-fluorenylidene group, or one selected from the group consisting of groups represented by the formulas: —$C_6H_4$—, —CONH—$C_6H_4$—NHCO—, —NHCO—$C_6H_4$—CONH—, —O—$C_6H_4$—CO—$C_6H_4$—O—, —OCO—$C_6H_4$—COO—, —OCO—$C_6H_4$—$C_6H_4$—COO—, —OCO—, —O—, —S—, —CO—, —CONH—, —$SO_2$—, —$C(CF_3)_2$—, —$C(CH_3)_2$—, —$CH_2$—, —O—$C_6H_4$—$C(CH_3)_2$—$C_6H_4$—O—, —O—$C_6H_4$—$C(CF_3)_2$—$C_6H_4$—O—, —O—$C_6H_4$—$SO_2$—$C_6H_4$—O—, —$C(CH_3)_2$—$C_6H_4$—$C(CH_3)_2$—, —O—$C_{10}H_6$—O—, —O—$C_6H_4$—$C_6H_4$—O—, and —O—$C_6H_4$—O—.

—$C_6H_4$— in the exemplification of Q is a phenylene group, preferably an m-phenylene group and a p-phenylene group, and more preferably a p-phenylene group.

—$C_{10}H_6$— is a naphthalenediyl group, preferably a naphthalene-1,2-diyl group, a naphthalene-1,4-diyl group, a naphthalene-2,3-diyl group, a naphthalene-2,6-diyl group, and a naphthalene-2,7-diyl group, and more preferably a naphthalene-1,4-diyl group and a naphthalene-2,6-diyl group.

$R^{11}$ in the formula (1) to the formula (4) is more preferably a hydrogen atom, a hydroxyl group, a fluorine atom, a methyl group, an ethyl group, or a trifluoromethyl group, and particularly preferably a hydrogen atom, a hydroxyl group, or a trifluoromethyl group, in view of the heat resistance of a cured film to be formed.

Q in the formula (4) is preferably a 9,9'-fluorenylidene group, —O—$C_6H_4$—O—, —$C(CF_3)_2$—, —O—, —$C(CH_3)_2$—, —$CH_2$—, or —O—$C_6H_4$—$C(CH_3)_2$—$C_6H_4$—O—, or —CONH—, and particularly preferably —O—$C_6H_4$—O—, —$C(CF_3)_2$—, or —O—, in view of the balance between the heat resistance of the cured film to be formed and the solubility of the unexposed photosensitive resin composition in an organic solvent.

Among the groups represented by the formulas (1) to (4), a group represented by the formula (3) or the formula (4) is more preferable, and a group represented by the formula (4) is particularly preferable, since it becomes easier to form a cured film with a more excellent heat resistance.

It is possible to employ, as $Y^1$, a silicon atom-containing group optionally having a chain aliphatic group and/or an aromatic ring. It is typically preferred to use, as the silicon atom-containing group, groups shown below.

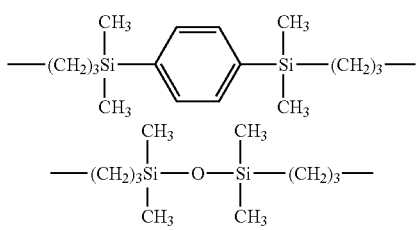

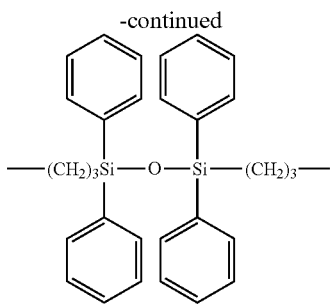

In view of further improving the transparency and mechanical properties of the resulting cured film, it is also possible to preferably use as $Y^1$ a group represented by the following formula (Si-1):

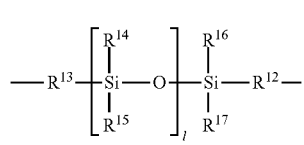

(Si-1)

wherein, in the formula, $R^{12}$ and $R^{13}$ each independently represent a single bond, a methylene group, an alkylene group having 2 or more and 20 or less carbon atoms, a cycloalkylene group having 3 or more and 20 or less carbon atoms, or an arylene group having 6 or more and 20 or less carbon atoms; $R^{14}$, $R^{15}$, $R^{16}$, and $R^{17}$ each independently represent an alkyl group having 1 or more and 20 or less carbon atoms, a cycloalkyl group having 3 or more and 20 or less carbon atoms, an aryl group having 6 or more and 20 or less carbon atoms, an amino group having 20 or less carbon atoms, a group represented by —O—$R^{18}$ ($R^{18}$ is a hydrocarbon group having 1 or more and 20 or less carbon atoms), or an organic group containing an epoxy group having 2 or more and 20 or less carbon atoms; and $l$ is an integer of 3 or more and 50 or less.

The alkylene group having 2 or more and 20 or less carbon atoms as $R^{12}$ and $R^{13}$ in the formula (Si-1) is preferably an alkylene group having 2 or more and 10 or less carbon atoms in view of the heat resistance and residual stress, and examples thereof include a dimethylene group, a trimethylene group, a tetramethylene group, a pentamethylene group, a hexamethylene group, and the like.

The cycloalkylene group having 3 or more and 20 or less carbon atoms as $R^{12}$ and $R^{13}$ in the formula (Si-1) is preferably a cycloalkylene group having 3 or more and 10 or less carbon atoms according to the abovementioned viewpoint, and examples thereof include a cyclobutylene group, a cyclopentylene group, a cyclohexylene group, a cycloheptylene group, and the like. The arylene group having 6 or more and 20 or less carbon atoms as $R^{12}$ and $R^{13}$ in the formula (Si-1) is preferably an aromatic group having 3 or more and 20 or less carbon atoms according to the abovementioned viewpoint, and examples thereof include a phenylene group, a naphthylene group, and the like.

The alkyl group having 1 or more and 20 or less carbon atoms as $R^{14}$, $R^{15}$, $R^{16}$, and $R^{17}$ in the formula (Si-1) is preferably an alkyl group having 1 or more and 10 or less carbon atoms from the viewpoint of the heat resistance and residual stress, and specific examples thereof include a methyl group, an ethyl group, a propyl group, an isopropyl group, a butyl group, an isobutyl group, a tert-butyl group, a pentyl group, a hexyl group, and the like. The cycloalkyl group having 3 or more and 20 or less carbon atoms as $R^{14}$, $R^{15}$, $R^{16}$, and $R^{17}$ in the formula (Si-1) is preferably a cycloalkyl group having 3 or more and 10 or less carbon atoms according to the abovementioned viewpoint, and specific examples thereof include a cyclopentyl group, a cyclohexyl group, and the like. The aryl group having 6 or more and 20 or less carbon atoms as $R^{14}$, $R^{15}$, $R^{16}$, and $R^{17}$ in the formula (Si-1) is preferably an aryl group having 6 or more and 12 or less carbon atoms according to the abovementioned viewpoint, and specific examples thereof include a phenyl group, a tolyl group, a naphthyl group, and the like. Examples of the amino group having 20 or less carbon atoms as $R^{14}$, $R^{15}$, $R^{16}$, and $R^{17}$ in the formula (Si-1) include an amino group, a substituted amino group (e.g., bis(trialkylsilyl)amino group), and the like. Examples of a group represented by —O—$R^{18}$ as $R^{14}$, $R^{15}$, $R^{16}$, and $R^{17}$ in the formula (Si-1) include a methoxy group, an ethoxy group, a propoxy group, an isopropyloxy group, a butoxy group, a phenoxy group, a tolyloxy group, a naphthyloxy group, a propenyloxy group (e.g., allyloxy group), and a cyclohexyloxy group. Among these, $R^{14}$, $R^{15}$, $R^{16}$, and $R^{17}$ preferably represent a methyl group, an ethyl group, a propyl group, or a phenyl group.

The group represented by the formula (Si-1) can be introduced by reacting a silicon-containing compound having an amino group at both ends with an acid anhydride. Specific examples of the silicon-containing compound include both-end amino-modified methyl phenyl silicone (e.g, X-22-1660B-3 (number average molecular weight of about 4,400) and X-22-9409 (number average molecular weight of about 1,300) manufactured by Shin-Etsu Chemical Co., Ltd.), both-end amino-modified dimethyl silicone (e.g., X-22-161A (number average molecular weight of about 1,600), X-22-161B (number average molecular weight of about 3,000), and KF8012 (number average molecular weight of about 4,400) manufactured by Shin-Etsu Chemical Co., Ltd., BY16-835U (number average molecular weight of about 900 manufactured by Dow Corning Toray Co., Ltd.), and Silaplane FM3311 manufactured by JNC Corporation (number average molecular weight of about 1,000).

In the above-mentioned polyamide resin including a structural unit represented by the formula (a1), the amount of the group represented by the formula (a3) is preferably 50 mol % or more, more preferably 60 mol % or more, still more preferably 70 mol % or more, yet more preferably 80 mol % or more, further preferably 90 mol % or more, and most preferably 100 mol %, based on the total amount of $R^{a1}$ and $R^{a2}$, since the curability of the photosensitive resin composition and the transparency of a cured film formed by using the photosensitive resin composition are satisfactory.

The polyamide resin may include a structural unit other than the above structural unit represented by the formula (a1), as long as it does not interfere with the object of the present invention. The structural unit other than the above structural unit represented by the formula (a1) is preferably, for example, a structural unit produced by condensation of a diamine component, which imparts the above $Y^1$, with various dicarboxylic acids. The condensation is performed in accordance with a conventionally known method for producing a polyamide resin.

Suitable specific examples of the dicarboxylic acid which imparts other structural units include adipic acid, sebacic acid, terephthalic acid, isophthalic acid, 2,6-naphthalenedicarboxylic acid, 1,6-naphthalenedicarboxylic acid, 2,7-naphthalenedicarboxylic acid, 1,4-naphthalenedicarboxylic acid, and 4,4'-dicarboxybiphenyl, and alkyl, alkoxy, or halogen substitution products thereof.

The other structural unit may be a polyamide unit derived from lactam. Examples of the other structural unit include a nylon 6 unit derived from ε-caprolactam, a nylon 11 unit derived from undecanelactam, a nylon 12 unit derived from lauryllactam, and the like.

Moreover, a polyamic acid type structural unit produced by condensation of a tetracarboxylic dianhydride with a diamine component, which imparts the $Y^1$, is also preferable as the other structural unit.

Suitable examples of tetracarboxylic dianhydrides, which impart other structural units, include aliphatic or alicyclic tetracarboxylic dianhydrides such as butanetetracarboxylic dianhydride, 1,2,3,4-cyclobutanetetracarboxylic dianhydride, 1,2,3,4-cyclopentanetetracarboxylic dianhydride, 2,3,5-tricarboxycyclopentylacetic dianhydride, 3,5,6-tricarboxynorbornane-2-acetic dianhydride, 2,3,4,5-tetrahydrofurantetracarboxylic dianhydride, 1,3,3a,4,5,9b-hexahydro-5-(tetrahydro-2,5-dioxo-3-furanyl)-naphtho[1,2-c]-furan-1,3-dione, 1,3,3a,4,5,9b-hexahydro-5-methyl-5-(tetrahydro-2,5-dioxo-3-furanyl)-naphtho[1,2-c]-furan-1,3-dione, 1,3,3a,4,5,9b-hexahydro-8-methyl-5-(tetrahydro-2,5-dioxo-3-furanyl)-naphtho[1,2-c]-furan-1,3-dione, 5-(2,5-dioxotetrahydrofuranyl)-3-methyl-3-cyclohexene-1,2-dicarboxylic dianhydride, bicyclo[2.2.2]-oct-7-ene-2,3,5,6-tetracarboxylic dianhydride, bicyclo[2.2.1]-heptane-2,3,5,6-tetracarboxylic dianhydride, (4H,8H)-decahydro-1,4:5,8-dimethanonaphthalene-2,3,6,7-tetracarboxylic dianhydride, and pentacyclo[9.2.1.1$^{4,7}$.0$^{2,10}$.0$^{3,8}$]-pentadecane-5,6,12,13-tetracarboxylic dianhydride; and aromatic tetracarboxylic dianhydrides such as pyromellitic dianhydride, 3,3',4,4'-benzophenonetetracarboxylic dianhydride, 3,3',4,4'-biphenyl sulfonetetracarboxylic dianhydride, 1,4,5,8-naphthalenetetracarboxylic dianhydride, 2,3,6,7-naphthalenetetracarboxylic dianhydride, 3,3',4,4'-biphenylethertetracarboxylic dianhydride, 3,3',4,4'-dimethyldiphenylsilanetetracarboxylic dianhydride, 3,3',4,4'-tetraphenylsilanetetracarboxylic dianhydride, 1,2,3,4-furantetracarboxylic dianhydride, 4,4'-bis(3,4-dicarboxyphenoxy)diphenyl sulfide dianhydride, 4,4'-bis(3,4-dicarboxyphenoxy)diphenyl sulfone dianhydride, 4,4'-bis(3,4-dicarboxyphenoxy)diphenylpropane dianhydride, 3,3',4,4'-perfluoroisopropylidenediphthalic dianhydride, 4,4'-(2,2-hexafluoroisopropylidene)diphthalic dianhydride, 3,3',4,4'-biphenyltetracarboxylic dianhydride, 2,3,3',4'-biphenyltetracarboxylic dianhydride, bis(phthalic acid) phenylphosphine oxide dianhydride, p-phenylene-bis(triphenylphthalic acid) dianhydride, m-phenylene-bis(triphenylphthalic acid) dianhydride, bis(triphenylphthalic acid)-4,4'-diphenylether dianhydride, and bis(triphenylphthalic acid)-4,4'-diphenylmethane dianhydride.

The method for producing the polyamide resin described above is not particularly limited, but is preferably a method including condensing a polyvalent carboxylic acid compound represented by the following formula (I):

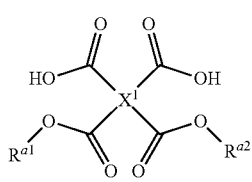

(I)

wherein, in the formula (I), $X^1$ is a tetravalent group represented by the following formula (a2):

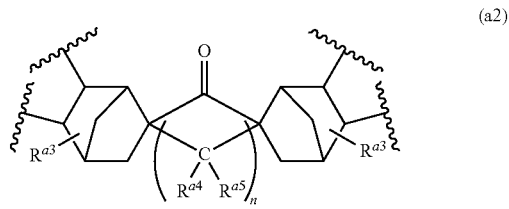

(a2)

$R^{a1}$ and $R^{ae}$ each independently represent a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

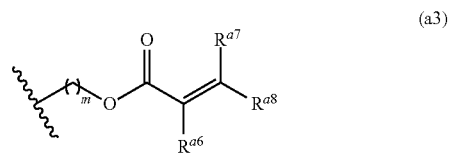

(a3)

at least one of $R^{a1}$ and $R^{a2}$ is a group represented by the formula (a3), in the formula (a2), $R^{a3}$, $R^{a4}$, and $R^{a5}$ each independently represent one selected from the group consisting of a hydrogen atom, an alkyl group having 1 or more and 10 or less carbon atoms, and a fluorine atom, n is an integer of 0 or more and 12 or less, in the formula (a3), $R^{a6}$, $R^{a7}$, and $R^{a8}$ each independently represent a hydrogen atom or an organic group having 1 or more and 3 or less carbon atoms, m is an integer of 2 or more and 10 or less, and/or an acid halide of the polyvalent carboxylic acid compound, with a diamine compound represented by the following formula (II):

$$H_2N-Y^1-NH_2 \quad (II)$$

wherein, in the formula (II), $Y^1$ is a divalent organic group.

$R^{a1}$, $R^{a2}$, and $X^1$ in the formula (I) and $Y^1$ in the formula (II) are as mentioned hereinabove with respect to the formula (a1). The formula (a2) and the formula (a3) are also as mentioned hereinabove.

The preferred method for producing a polyamide resin is, for example, a method in which a polyvalent carboxylic acid compound represented by the formula (I) is condensed with a diamine compound represented by the formula (II) in the presence of a condensing agent. Examples of the condensing agent include dicyclohexylcarbodiimide, 1-ethoxycarbonyl-2-ethoxy-1,2-dihydroquinoline, 1,1-carbonyldioxy-di-1,2,3-benzotriazole, N,N'-disuccinimidyl carbonate, and the like.

Other preferred methods include a method in which a polyvalent carboxylic acid compound represented by the formula (I), or an acid halide of the polyvalent carboxylic acid compound represented by the formula (I) is condensed with a diamine represented by the formula (II) in the presence of a base. In this method, if necessary, a condensing agent may be used along with the base. The acid halide is preferably an acid chloride and an acid bromide, and more preferably an acid chloride. Examples of the base include pyridine, triethylamine, 4-dimethylaminopyridine, and the like. Examples of the condensing agent include triphenyl phosphite, dicyclohexylcarbodiimide, 1-ethyl-3-(3-dimethylaminopropyl)carbodiimide hydrochloride, N,N'-carbonyldiimidazole, dimethoxy-1,3,5-triazinylmethylmorpholinium, O-(benzotriazol-1-yl)-N,N,N',N'-tetramethyluronium tetrafluoroborate, O-(benzotriazol-1-yl)-N,N,N',N'-tetramethyluroniumhexafluorophospahte, diphenyl (2,3-dihydro-2-thioxo-3-benzooxazolyl)phosphonate, 4-(4,6-dimethoxy-1,3,5-triazin-2-yl)4-methoxymorpholiniumchloride hydrate, and the like.

Specifically, a polyvalent carboxylic acid compound represented by the formula (I) or an acid halide of the polyvalent carboxylic acid compound represented by the formula (I) is reacted with a diamine represented by the formula (II) in the presence of the base in an organic solvent, for example, at −20° C. or higher and 150° C. or lower, preferably 0° C. or higher and 50° C. or lower, for 30 minutes or more and 24 hours or less, preferably 1 hour or more and 4 hours or less. The amount of the base to be used is preferably 2 times or more and 4 times or less based on the amount of the mol of the polyvalent carboxylic acid compound represented by the formula (I) or an acid halide of the polyvalent carboxylic acid compound represented by the formula (I), since this is an amount which allows easy obtainment of a high-molecular-weight body and easy removal.

An organic solvent to be used when reacting a polyvalent carboxylic acid compound represented by the formula (I) or an acid halide of the polyvalent carboxylic acid compound represented by the formula (I) with a diamine represented by the formula (II) can be appropriately selected from known organic solvents which do not inhibit this reaction. Among known organic solvents, nitrogen-containing polar organic solvents such as N-methyl-2-pyrrolidone, N,N-dimethylacetamide, N,N-diethylacetamide, N,N-dimethylformamide, N,N-diethylformamide, N,N-dimethylisobutylamide, N-methylcaprolactam, and N,N,N',N'-tetramethylurea are preferable since a raw material compound and the polyamide resin to be produced are satisfactorily dissolved.

It is also possible to produce a polyamide resin including a structural unit represented by the formula (a1) by condensing a tetracarboxylic dianhydride represented by the following formula (a4):

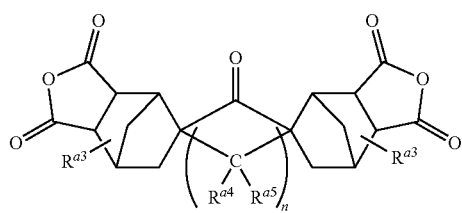

(a4)

with a diamine compound represented by the formula (II) in accordance with an ordinary method to obtain a polyamic acid, and then partially or entirely esterifying the carboxy groups contained in the resulting polyamic acid.

The reaction of the tetracarboxylic dianhydride component with the diamine compound is usually performed in an organic solvent. The organic solvent to be used in the reaction of the tetracarboxylic dianhydride component with the diamine compound is not particularly limited as long as it is an organic solvent which can dissolve the diamine compound and the tetracarboxylic dianhydride component, and does not react with the diamine compound and the tetracarboxylic dianhydride component. These organic solvents can be used alone, or two or more organic solvents can be used in combination. The preferred organic solvent is the same as the organic solvent which is used when reacting a polyvalent carboxylic acid compound represented by the formula (I) or an acid halide thereof with a diamine represented by the formula (II).

During the synthesis of the polyamic acid, the organic solvent is used in an amount so that the total mass of the tetracarboxylic dianhydride component and the diamine compound is 0.1% by mass or more and 50% by mass or less, preferably 10% by mass or more and 30% by mass or less, in the reaction solution.

When reacting the tetracarboxylic dianhydride component with the diamine compound, a base compound may be further added in the organic solvent in view of improving the reaction rate and obtaining a polyamic acid with high polymerization degree. Examples of the basic compound include, but are not particularly limited to, triethylamine, tetrabutylamine, tetrahexylamine, 1,8-diazabicyclo[5.4.0]-undecene-7, pyridine, isoquinoline, α-picoline, and the like. The amount of the base compound to be used is preferably 0.001 equivalent or more and 10 equivalents or less, and more preferably 0.01 equivalent or more and 0.1 equivalent or less, based on 1 equivalent of the tetracarboxylic dianhydride component.

The reaction temperature at which the tetracarboxylic dianhydride component is reacted with the diamine compound is not particularly limited as long as the reaction satisfactorily proceeds, but is preferably 15° C. or higher and 30° C. or lower. The reaction is preferably performed under an inert gas atmosphere. The reaction time is also not particularly limited, but is preferably, for example, 10 hours or more and 48 hours or less.

Suitable specific examples of the diamine represented by the formula (II) include p-phenylenediamine, m-phenylenediamine, o-phenylenediamine, 4,4'-diaminodiphenyl ether, 3,3'-diaminodiphenyl ether, 3,4'-diaminodiphenyl ether, 4,4'-diaminodiphenyl sulfide, 3,3'-diaminodiphenyl sulfide, 3,4'-diaminodiphenyl sulfide, 4,4'-diaminodiphenyl sulfone, 3,3'-diaminodiphenyl sulfone, 3,4'-diaminodiphenyl sulfone, 4,4'-diaminobiphenyl, 3,3'-diaminobiphenyl, 2,2'-diaminobiphenyl, 3,4'-diaminobiphenyl, 4,4'-diaminobenzophenone, 3,3'-diaminobenzophenone, 3,4'-diaminobenzophenone, 4,4'-diaminodiphenylmethane, 3,3'-diaminodiphenylmethane, 3,4'-diaminophenylmethane, 4,4'-diaminobenzanilide, 1,4-bis(4-aminophenoxy)benzene, 1,3-bis(4-aminophenoxy)benzene, 1,3-bis(3-aminophenoxy)benzene, bis[4-(4-aminophenoxy)phenyl] sulfone, bis[4-(3-aminophenoxy)phenyl] sulfone, 4,4'-bis(4-aminophenoxy)biphenyl, 4,4'-bis(3-aminophenoxy)biphenyl, bis-[4-(4-aminophenoxy)phenyl]ether, bis-[4-(3-aminophenoxy)phenyl]ether, 1,4-bis(4-aminophenyl)benzene, 1,3-bis(4-aminophenyl)benzene, 9,10-bis(4-aminophenyl)anthracene, 2,2-bis(4-aminophenyl)propane, 2,2-bis(3-aminophenyl) hexafluoropropane, 2,2-bis(4-aminophenyl)hexafluoropropane, 2,2-bis[4-(4-aminophenoxy)phenyl]propane, 2,2-bis[4-(4-aminophenoxy)phenyl]hexafluoropropane, 1,4-bis(3-aminopropyldimethylsilyl)benzene, o-tolidine sulfone, 9,9-bis(4-aminophenyl)fluorine, and the like. The diamine is also preferably a compound in which hydrogen atoms on the aromatic ring contained in these aromatic diamines are partially substituted with a methyl group, an ethyl group, a hydroxyl group, a methoxy group, an ethoxy group, a trifluoromethyl group, a hydroxymethyl group, a hydroxyethyl group, halogen, or the like. Specific examples thereof include aromatic diamines substituted with a methyl group, such as 3,3'-dimethyl-4,4'-diaminobiphenyl, 2,2'-dimethyl- 4,4'-diaminobiphenyl, 3,3'-dimethyl-4,4'-diaminodiphenylmethane, 2,2'-dimethyl-4,4'-diaminodiphenylmethane, 2,2-bis(3-methyl-4-aminophenyl)propane, 2,2-bis(2-methyl-4-aminophenyl)propane, 2,2-bis(3-methyl-4-aminophenyl)hexafluoropropane, and 2,2-bis(2-methyl-4-aminophenyl)hexafluoropropane; aromatic diamines substituted with a trifluoromethyl group, such as 3,3'-ditrifluoromethyl-4,4'-diaminobiphenyl, 2,2'-ditrifluoromethyl-4,4'-diaminobiphenyl, 3,3'-ditrifluoromethyl-4,4'-diaminodiphenylmethane, 2,2'-ditrifluoromethyl-4,4'-diaminodiphenylmethane, 2,2-bis(3-trifluoromethyl-4-aminophenyl)propane, 2,2-bis(2-trifluoromethyl-4-aminophenyl)propane, 2,2-bis(3-trifluoromethyl-4-aminophenyl)hexafluoropropane, and 2,2-bis(2-trifluoromethyl-4-aminophenyl)hexafluoropropane;
aromatic diamines substituted with a methoxy group, such as 3,3'-dimethoxy-4,4'-diaminobiphenyl, 2,2'-dimethoxy-4,4'-diaminobiphenyl, 3,3'-dimethoxy-4,4'-diaminodiphenylmethane, 2,2'-dimethoxy-4,4'-diaminodiphenylmethane, 2,2-bis(3-methoxy-4-aminophenyl)propane, 2,2-bis(2-methoxy-4-aminophenyl)propane, 2,2-bis(3-methoxy-4-aminophenyl)hexafluoropropane, and 2,2-bis(2-methoxy-4-aminophenyl)hexafluoropropane; aromatic diamines substituted with a chlorine atom, such as 3,3'-dichloro-4,4'-diaminobiphenyl, 2,2'-dichloro-4,4'-diaminobiphenyl, 3,3'-dichloro-4,4'-diaminodiphenylmethane, 2,2'-dichloro-4,4'-diaminodiphenylmethane, 2,2-bis(3-chloro-4-aminophenyl)propane, 2,2-bis(2-chloro-4-aminophenyl)propane, 2,2-bis(3-chloro-4-aminophenyl)hexafluoropropane, and 2,2-bis(2-chloro-4-aminophenyl)hexafluoropropane; and aromatic diamines substituted with a hydroxy group, such as 3,3'-dihydroxy-4,4'-diaminobiphenyl, 2,2'-dihydroxy-4,4'-diaminobiphenyl, 3,3'-dihydroxy-4,4'-diaminodiphenylmethane, 2,2'-dihydroxy-4,4'-diaminodiphenylmethane, 2,2-bis(3-hydroxy-4-aminophenyl)propane, 2,2-bis(2-hydroxy-4-aminophenyl)propane, 2,2-bis(3-hydroxy-4-aminophenyl)hexafluoropropane, 2,2-bis(2-hydroxy-4-aminophenyl)hexafluoropropane, and 2,2-bis(3-amino-4-hydroxyphenyl)hexafluoropropane.

The weight average molecular weight (Mw) of the above-described polyamide resin including a structural unit represented by the formula (a1) is preferably 50,000 or less, more preferably 4,000 or more and 30,000 or less, and still more preferably 5,000 or more and 20,000 or less. Use of a polyamide resin having a molecular weight in the above range tends to suppress the generation of gel-like insolubles during the preparation of the photosensitive resin composition. Even if gel-like insolubles are generated, it is possible to obtain a photosensitive resin composition which can be used without problems by removing the insolubles using methods such as filtration. However, it is more suitable to adjust the weight average molecular weight to the value mentioned above since such a process would no longer be required. As used herein, the weight average molecular weight is defined as a relative value in terms of polystyrene in gel permeation chromatography (GPC) measurement.

[Other Resin]

The resin (A) may include, in addition to a polyamide resin including a structural unit represented by the above formula (a1), other resins. The other resins are not particularly limited as long as it is possible to uniformly mix them with the photosensitive resin composition and they do not interfere with the object of the present invention. Specific examples of the other resins include a polyamide resin including no structural units represented by the formula (a1), a polymer of a styrene-based monomer, a novolac resin, a polymer of a (meth)acryl-based monomer, a copolymer of a styrene-based monomer and a (meth)acryl-based monomer, a polyolefin (polyethylene, polypropylene, etc.), a polyimide resin, and the like.

The content of the resin (A) in the photosensitive resin composition is not particularly limited as long as it does not interfere with the object of the present invention. Typically, the content is preferably 30% by mass or more and 98% by mass or less, more preferably 40% by mass or more and 95% by mass or less, and still more preferably 50% by mass or more and 92% by mass or less, based on the mass of the total solid component of the photosensitive resin composition.

<Photopolymerization Initiator (B)>

The photosensitive resin composition contains a photopolymerization initiator (B). Due to the photosensitive resin composition containing a photopolymerization initiator, when the photosensitive resin composition is exposed, intermolecular crosslinking of resin (A) having a polymerizable group represented by the formula (a3) proceeds, and thus the photosensitive resin composition is cured. The photopolymerization initiator (B) is not particularly limited, and it is possible to use a conventionally known photopolymerization initiator.

Specific examples of the photopolymerization initiator (B) include 1-hydroxycyclohexyl phenyl ketone, 2-hydroxy-2-methyl-1-phenylpropan-1-one, 1-[4-(2-hydroxyethoxy)phenyl]-2-hydroxy-2-methyl-1-propan-1-one, 1-(4-isopropylphenyl)-2-hydroxy-2-methylpropan-1-one, 1-(4-dodecylphenyl)-2-hydroxy-2-methylpropan-1-one, 2,2-dimethoxy-1,2-diphenylethan-1-one, bis(4-dimethylaminophenyl)ketone, 2-methyl-1-[4-(methylthio)phenyl]-2-morpholinopropan-1-one, 2-benzyl-2-dimethylamino-1-(4-morpholinophenyl)-butan-1-one, O-acetyl-1-[6-(2-methylbenzoyl)-9-ethyl-9H-carbazol-3-yl] ethanone oxime, (9-ethyl-6-nitro-9H-carbazol-3-yl) [4-(2-methoxy-1-methylethoxy)-2-methylphenyl]methanone O-acetyl oxime, 2-(benzoyloxyimino)-1-[4-(phenylthio)phenyl]-1-octanone, 2,4,6-trimethylbenzoyl diphenylphosphine oxide, 4-benzoyl-4'-methyldimethyl sulfide, 4-dimethylaminobenzoic acid, methyl 4-dimethylaminobenzoate, ethyl 4-dimethylaminobenzoate, butyl 4-dimethylaminobenzoate, 4-dimethylamino-2-ethylhexylbenzoic acid, 4-dimethylamino-2-isoamylbenzoic acid, benzyl-β-methoxyethylacetal, benzyldimethylketal, 1-phenyl-1,2-propanedione-2-(O-ethoxycarbonyl)oxime, methyl o-benzoylbenzoate, 2,4-diethylthioxanthone, 2-chlorothioxanthone, 2,4-dimethylthioxanthone, 1-chloro-4-propoxythioxanthone, thioxanthene, 2-chlorothioxanthene, 2,4-diethylthioxanthene, 2-methylthioxanthene, 2-isopropylthioxanthene, 2-ethylanthraquinone, octamethylanthraquinone, 1,2-benzanthraquinone, 2,3-diphenylanthraquinone, azobisisobutyronitrile, benzoyl peroxide, cumene hydroperoxide, 2-mercaptobenzimidazole, 2-mercaptobenzoxazole, 2-mercaptobenzothiazole, 2-(o-chlorophenyl)-4,5-di(m-methoxyphenyl)-imidazolyl dimer, benzophenone, 2-chlorobenzophenone, p,p'-bisdimethylaminobenzophenone, 4,4'-bisdiethylaminobenzophenone, 4,4'-dichlorobenzophenone, 3,3-dimethyl-4-methoxybenzophenone, benzyl, benzoin, benzoin methyl ether, benzoin ethyl ether, benzoin isopropyl ether, benzoin n-butyl ether, benzoin isobutyl ether, benzoin butyl ether, acetophenone, 2,2-diethoxyacetophenone, p-dimethylacetophenone, p-dimethylaminopropiophenone, dichloroacetophenone, trichloroacetophenone, p-tert-butylacetophenone, p-dimethylaminoacetophenone, p-tert-butyltrichloroacetophenone, p-tert-butyldichloroacetophenone, α,α-dichloro-4-phenoxyacetophenone, thioxanthone, 2-methylthioxanthone, 2-isopropylthioxanthone, dibenzosuberone, pentyl-4-dimethylaminobenzoate, 9-phenylacridine, 1,7-bis-(9-acridinyl)heptane, 1,5-bis-(9-acridinyl)pentane, 1,3-bis-(9-acridinyl)propane, p-methoxytriazine, 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, 2-(4-n-butoxyphenyl)-4,6-bis(trichloromethyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(3-bromo-4-methoxy)styrylphenyl-s-triazine, 2,4-bis-trichloromethyl-6-(2-bromo-4-methoxy)styrylphenyl-s-triazine, and the like. These photopolymerization initiators can be used alone, or two or more photopolymerization initiators can be used in combination.

Among these, an oxime-based photopolymerization initiator is particularly preferably used in view of the sensitivity. Among oxime-based photopolymerization initiators, O-acetyl-1-[6-(2-methylbenzoyl)-9-ethyl-9H-carbazol-3-yl]ethanone oxime, ethanone,1-[9-ethyl-6-(pyrrol-2-ylcarbonyl)-9H-carbazol-3-yl], 1-(O-acetyloxime), and 2-(benzoyloxyimino)-1-[4-(phenylthio)phenyl]-1-octanone are particularly preferable.

It is also preferred to use, as the photopolymerization initiator, an oxime-based compound represented by the following formula (b1):

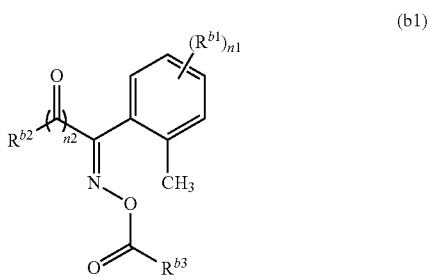

wherein $R^{b1}$ is a group selected from the group consisting of a monovalent organic group, an amino group, halogen, a nitro group, and a cyano group,
n1 is an integer of 0 or more and 4 or less,
n2 is 0 or 1,
$R^{b2}$ is an optionally substituted phenyl group or an optionally substituted carbazolyl group, and
$R^{b3}$ is a hydrogen atom, or an alkyl group having 1 or more and 6 or less carbon atoms.

In the formula (b1), $R^{b1}$ is not particularly limited as long as the object of the present invention is not inhibited, and is appropriately selected from various organic groups. When $R^{b1}$ is an organic group, suitable examples include an alkyl group, an alkoxy group, an cycloalkyl group, an cycloalkoxy group, a saturated aliphatic acyl group, a saturated aliphatic acyloxy group, an alkoxycarbonyl group, a phenyl group which may have a substituent, a phenoxy group which may have a substituent, a benzoyl group which may have a substituent, a phenoxycarbonyl group which may have a substituent, a benzoyloxy group which may have a substituent, a phenylalkyl group which may have a substituent, a naphthyl group which may have a substituent, a naphthoxy group which may have a substituent, a naphthoyl group which may have a substituent, a naphthoxycarbonyl group which may have a substituent, a naphthoyloxy group which may have a substituent, a naphthylalkyl group which may have a substituent, a heterocyclylic group which may have a substituent, an amino group, an amino group substituted with one or two organic groups, a morpholin-1-yl group, a piperazin-1-yl group, a halogen, a nitro group, a cyano group, and the like. When n1 is an integer of 2 or more and 4 or less, $R^{b1}$ may be the same or different. The number of carbon atoms of the substituent does not include the number of carbon atoms of the substituent possessed by the substituent.

When $R^{b1}$ is an alkyl group, the number of carbon atoms of the alkyl group is preferably 1 or more and 20 or less, and more preferably 1 or more and 6 or less. When $R^{b1}$ is an alkyl group, the alkyl group may be either one of a straight chain or branched chain alkyl group. When $R^{b1}$ is an alkyl group, specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group, and the like. When $R^{b1}$ is an alkyl group, the alkyl group may contain an ether bond (—O—) in the carbon chain. Examples of the alkyl group having an ether bond in the carbon chain include a methoxyethyl group, an ethoxyethyl group, a methoxyethoxyethyl group, an ethoxyethoxyethyl group, a propyloxyethoxyethyl group, a methoxypropyl group, and the like.

When $R^{b1}$ is an alkoxy group, the number of carbon atoms of the alkoxy group is preferably 1 or more and 20 or less, and more preferably 1 or more and 6 or less. When $R^{b1}$ is an alkoxy group, the alkoxy group may be either one of a straight chain or branched chain alkoxy group. When $R^{b1}$ is an alkoxy group, specific examples include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, an isodecyloxy group, and the like. When $R^{b1}$ is an alkoxy group, the alkoxy group may include an ether bond (—O—) in the carbon chain. Examples of the alkoxy group having an ether bond in the carbon chain include a methoxyethoxy group, an ethoxyethoxy group, a methoxyethoxyethoxy group, an ethoxyethoxyethoxy group, a propyloxyethoxyethoxy group, a methoxypropyloxy group, and the like.

When $R^{b1}$ is a cycloalkyl group or a cycloalkoxy group, the number of carbon atoms of the cycloalkyl group or cycloalkoxy group is preferably 3 or more and 10 or less, and more preferably 3 or more and 6 or less. When $R^{b1}$ is a cycloalkyl group, specific examples include a cyclopropyl group, a cyclobutyl group, a cyclopentyl group, a cyclohexyl group, a cycloheptyl group, a cyclooctyl group, and the like. When $R^{b1}$ is a cycloalkoxy group, specific examples include a cyclopropyloxy group, a cyclobutyloxy group, a cyclopentyloxy group, a cyclohexyloxy group, a cycloheptyloxy group, a cyclooctyloxy group, and the like.

When $R^{b1}$ is a saturated aliphatic acyl group or a saturated aliphatic acyloxy group, the number of carbon atoms of the saturated aliphatic acyl group or saturated aliphatic acyloxy group is preferably 2 or more and 20 or less, and more preferably 2 or more and 7 or less. When $R^{b1}$ is a saturated aliphatic acyl group, specific examples include an acetyl group, a propanoyl group, an n-butanoyl group, a 2-methylpropanoyl group, an n-pentanoyl group, a 2,2-dimethylpropanoyl group, an n-hexanoyl group, an n-heptanoyl group, an n-octanoyl group, an n-nonanoyl group, an n-decanoyl group, an n-undecanoyl group, an n-dodecanoyl group, an n-tridecanoyl group, an n-tetradecanoyl group, an n-pentadecanoyl group, n-hexadecanoyl group, and the like. When $R^{b1}$ is a saturated aliphatic acyloxy group, specific examples include an acetyloxy group, a propanoyloxy group, an n-butanoyloxy group, a 2-methylpropanoyloxy group, an n-pentanoyloxy group, a 2,2-dimethylpropanoyloxy group, an n-hexanoyloxy group, an n-heptanoyloxy group, an n-octanoyloxy group, an n-nonanoyloxy group, an n-decanoyloxy group, an n-undecanoyloxy group, an n-dodecanoyloxy group, an n-tridecanoyloxy group, an n-tetradecanoyloxy group, an n-pentadecanoyloxy group, an n-hexadecanoyloxy group, and the like.

When $R^{b1}$ is an alkoxycarbonyl group, the number of carbon atoms of the alkoxycarbonyl group is preferably 2 or more and 20 or less, and more preferably 2 or more and 7 or less. When $R^{b1}$ is an alkoxycarbonyl group, specific examples include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an isopentyloxycarbonyl group, a sec-pentyloxycarbonyl group, a tert-pentyloxycarbonyl group, an n-hexyloxycarbonyl group, an n-heptyloxycarbonyl group, an n-octyloxycarbonyl group, an isooctyloxycarbonyl group, a sec-octyloxycarbonyl group, a tert-octyloxycarbonyl group, an n-nonyloxycarbonyl group, an isononyloxycarbonyl group, an n-decyloxycarbonyl group, an isodecyloxycarbonyl group, and the like.

When $R^{b1}$ is a phenylalkyl group, the number of carbon atoms of the phenylalkyl group is preferably 7 or more and 20 or less, and more preferably 7 or more and 10 or less. When $R^{b1}$ is a naphthylalkyl group, the number of carbon atoms of the naphthylalkyl group is preferably 11 or more and 20 or less, and more preferably 11 or more and 14 or less. When $R^{b1}$ is a phenylalkyl group, specific examples include a benzyl group, a 2-phenylethyl group, a 3-phenylpropyl group, and a 4-phenylbutyl group. When $R^{b1}$ is a naphthylalkyl group, specific examples include an α-naphthylmethyl group, a β-naphthylmethyl group, a 2-(α-naphthyl)ethyl group, and a 2-(β-naphthyl)ethyl group. When $R^{b1}$ is a phenylalkyl group or naphthylalkyl group, $R^{b1}$ may further have a substituent on a phenyl group or a naphthyl group.

When $R^{b1}$ is a heterocyclylic group, the heterocyclylic group is a 5- or 6-membered single ring containing one or more N, S, and O, or a heterocyclylic group in which single rings are fused each other, or a single ring is fused with a benzene ring. When the heterocyclylic group is a fused ring, the number of rings in the fused ring is 3 or less. Examples of the heterocycle constituting the heterocyclylic group include furan, thiophene, pyrrole, oxazole, isoxazole, thiazole, thiadiazole, isothiazole, imidazole, pyrazole, triazole, pyridine, pyrazine, pyrimidine, pyridazine, benzofuran, benzothiophene, indole, isoindole, indolizine, benzoimidazole, benzotriazole, benzoxazole, benzothiazole, carbazole, purine, quinoline, isoquinoline, quinazoline, phthalazine, cinnoline, quinoxaline, and the like. When $R^{b1}$ is a heterocyclylic group, the heterocyclylic group may have a substituent.

When $R^{b1}$ is an amino group substituted with one or two organic groups, suitable examples of the organic group include an alkyl group having 1 or more and 20 or less carbon atoms, a cycloalkyl group having 3 or more and 10 or less carbon atoms, a saturated aliphatic acyl group having 2 or more and 20 or less carbon atoms, a phenyl group which may have a substituent, a benzoyl group which may have a substituent, a phenylalkyl group having 7 or more and 20 or less carbon atoms which may have a substituent, a naphthyl group which may have a substituent, a naphthoyl group which may have a substituent, a naphthylalkyl group having 11 or more and 20 or less carbon atoms which may have a substituent, a heterocyclylic group, and the like. Specific examples of suitable organic group are the same as those in $R^{b1}$. Specific examples of the amino group substituted with one or two organic group include a methylamino group, an ethylamino group, a diethylamino group, an n-propylamino group, a di-n-propylamino group, an isopropylamino group, an n-butylamino group, a di-n-butylamino group, an n-pentylamino group, an n-hexylamino group, an n-heptylamino group, an n-octylamino group, an n-nonylamino group, an n-decylamino group, a phenylamino group, a naphthylamino group, an acetylamino group, an propanoylamino group, an n-butanoylamino group, an n-pentanoylamino group, an n-hexanoylamino group, an n-heptanoylamino group, an n-octanoylamino group, an n-decanoylamino group, a benzoylamino group, an α-naphthoylamino group, a β-naphthoylamino group, and the like.

When an phenyl group, an naphthyl group, and a heterocyclylic group included in $R^{b1}$ further have a substituent, examples of the substituent include an alkyl group having 1 or more and 6 or less carbon atoms, an alkoxy group having 1 or more and 6 or less carbon atoms, a saturated aliphatic acyl group having 2 or more and 7 or less carbon atoms, an alkoxycarbonyl group having 2 or more and 7 or less carbon atoms, a saturated aliphatic acyloxy group having 2 or more and 7 or less carbon atoms, a monoalkylamino group which has an alkyl group having 1 or more and 6 or less carbon atoms, a dialkylamino group which has two alkyl groups having 1 or more and 6 or less carbon atoms, a morpholin-1-yl group, an piperazin-1-yl group, halogen, a nitro group, a cyano group, and the like. When a phenyl group, a naphthyl group, and a heterocyclylic group included in $R^{b1}$ further have a substituent, the number of substituents is not particularly limited as long as the object of the present invention is not inhibited, and is preferably 1 or more and 4 or less. When a phenyl group, a naphthyl group, and a heterocyclylic group included in $R^{b1}$ have plural substituents, plural substituents may be the same as or different each other.

Among $R^{b1}$(s), a group selected from the group consisting of an alkyl group having 1 or more and 6 or less carbon atoms, an alkoxy group having 1 or more and 6 or less carbon atoms, and a saturated aliphatic acyl group having 2 or more and 7 or less carbon atoms is preferable, an alkyl having 1 or more and 6 or less carbon atoms is more preferable, and a methyl group is particularly preferable, since these are chemically stable and facilitates the synthesis of an oxime ester compound due to little steric hindrance.

When the position of a bond of a phenyl group and a main skeleton of an oxime ester compound is regarded as the 1-position and the position of a methyl group is regarded as the 2-position with respect to the phenyl group to which $R^{b1}$ is bonded, the position at which $R^{b1}$ is bonded to a phenyl group is preferably the 4-position or the 5-position, more preferably the 5-position.

n1 is preferably an integer of 0 or more and 3 or less, more preferably an integer of 0 or more and 2 or less, and particularly preferably 0 or 1.

$R^{b2}$ is a phenyl group which may have a substituent, or a carbazolyl group which may have a substituent. When $R^{b2}$ is a carbazolyl group which may have a substituent, the nitrogen atom on the carbazolyl group may be substituted with an alkyl group having 1 or more and 6 or less carbon atoms.

For $R^{b2}$, there is no particular limitation for substituents on the phenyl group or the carbazolyl group as long as they do not interfere with the object of the present invention. Examples of suitable substituents which the phenyl group or carbazolyl group may have on the carbon atom include an alkyl group having 1 or more and 20 or less carbon atoms, an alkoxy group having 1 or more and 20 or less carbon atoms, a cycloalkyl group having 3 or more and 10 or less carbon atoms, a cycloalkoxy group having 3 or more and 10 or less carbon atoms, a saturated aliphatic acyl group having 2 or more and 20 or less carbon atoms, an alkoxycarbonyl group having 2 or more and 20 or less carbon atoms, a saturated aliphatic acyloxy group having 2 or more and 20 or less carbon atoms, an optionally substituted phenyl group, an optionally substituted phenoxy group, an optionally substituted phenylthio group, an optionally substituted benzoyl group, an optionally substituted phenoxycarbonyl group, an optionally substituted benzoyloxy group, an optionally substituted phenylalkyl group having 7 or more and 20 or less carbon atoms, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group having 11 or more and 20 or less carbon atoms, an optionally substituted heterocyclyl group, an optionally substituted heterocyclylcarbonyl group, an amino group, an amino group substituted with 1 or 2 organic groups, a morpholine-1-yl group, a piperazine-1-yl group, halogen, a nitro group, a cyano group and the like.

In a case where $R^{b2}$ is a carbazolyl group, examples of suitable substituent which the carbazolyl group may have on the nitrogen atom include an alkyl group having 1 or more and 20 or less carbon atoms, a cycloalkyl group having 3 or more and 10 or less carbon atoms, a saturated aliphatic acyl group having 2 or more and 20 or less carbon atoms, an alkoxycarbonyl group having 2 or more and 20 or less carbon atoms, an optionally substituted phenyl group, an optionally substituted benzoyl group, an optionally substituted phenoxycarbonyl group, an optionally substituted phenylalkyl group having 7 or more and 20 or less carbon atoms, an optionally substituted naphthyl group, an optionally substituted naphthoyl group, an optionally substituted naphthoxycarbonyl group, an optionally substituted naphthylalkyl group having 11 or more and 20 or less carbon atoms, an optionally substituted heterocyclyl group, an optionally substituted heterocyclylcarbonyl group and the like. Among these substituents, an alkyl group having 1 or more and 20 or less carbon atoms is preferred, and an alkyl group having 1 or more and 6 or less carbon atoms is more preferred, and in particular an ethyl group is preferred.

For an alkyl group, an alkoxy group, a cycloalkyl group, a cycloalkoxy group, a saturated aliphatic acyl group, an alkoxycarbonyl group, a saturated aliphatic acyloxy group, an optionally substituted phenylalkyl group, an optionally substituted naphthylalkyl group, an optionally substituted heterocyclyl group and an amino group substituted with 1 or 2 organic groups, specific examples of optional substituents on the phenyl group or the carbazolyl group are same as those in $R^{b1}$.

In a case where the phenyl group, the naphthyl group and the heterocyclyl group included in the substituent on the phenyl group or the carbazolyl group in $R^{b2}$ further have a substituent, examples of the substituent include an alkyl group having 1 or more and 6 or less carbon atoms; an alkoxy group having 1 or more and 6 or less carbon atoms; a saturated aliphatic acyl group having 2 or more and 7 or less carbon atoms; an alkoxycarbonyl group having 2 or more and 7 or less carbon atoms; a saturated aliphatic acyloxy group having 2 or more and 7 or less carbon atoms; a phenyl group; a naphthyl group; a benzoyl group; a naphthoyl group; a benzoyl group substituted with a group selected from the group consisting of an alkyl group having 1 or more and 6 or less carbon atoms, a morpholine-1-yl group, a piperazine-1-yl group and a phenyl group; a monoalkylamino group having an alkyl group having 1 or more and 6 or less carbon atoms; a dialkylamino group having alkyl groups having 1 or more and 6 or less carbon atoms; a morpholine-1-yl group; a piperazine-1-yl group; halogen; a nitro group; and a cyano group. In a case where the phenyl group, the naphthyl group and the heterocyclyl group included in the substituent on the phenyl group or the carbazolyl group further have a substituent, the number of the substituent is not limited as far as objects of the present invention are not inhibited, but 1 or more and 4 or less is preferred. In a case where the phenyl group, the naphthyl group and the heterocyclyl group have multiple substituents, the substituents may be different from or the same as each other.

Among $R^{b2}(s)$, a group represented by the following formula (b2) or (b3) is preferable, a group represented by the following formula (b2) is more preferable, and a group represented by the following formula (b2) in which A is S is particularly preferable, since a photopolymerization initiator with excellent sensitivity is easily obtained.

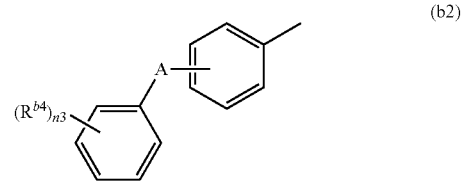

(b2)

$R^{b4}$ is a group selected from the group consisting of a monovalent organic group, an amino group, halogen, a nitro group and a cyano group; A is S or O; and n is an integer of 0 or more and 4 or less.

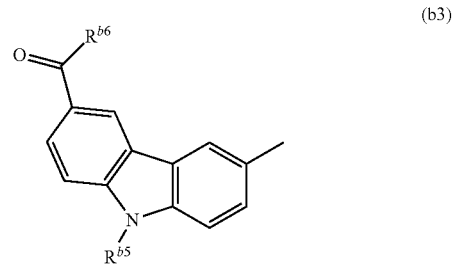

(b3)

$R^{b5}$ and $R^{b6}$ each are a monovalent organic group.

When $R^{b4}$ in formula (b2) is an organic group, $R^{b4}$ can be selected from various kinds of organic groups as far as objects of the present invention are not inhibited. Preferred examples when $R^{b4}$ is an organic group in formula (b2) include alkyl groups having 1 or more and 6 or less carbon atoms; alkoxy groups having 1 or more and 6 or less carbon atoms; saturated aliphatic acyl groups having 2 or more and 7 or less carbon atoms; alkoxycarbonyl groups having 2 or more and 7 or less carbon atoms; saturated aliphatic acyloxy groups having 2 or more and 7 or less carbon atoms; a phenyl group; a naphthyl group; a benzoyl group; a naphthoyl group; benzoyl groups substituted with a group selected from the group consisting of an alkyl group having 1 or more and 6 or less carbon atoms, a morpholine-1-yl group, a piperazine-1-yl group and a phenyl group; monoalkylamino groups having an alkyl group having 1 or more and 6 or less carbon atoms; dialkylamino groups having alkyl groups having 1 or more and 6 or less carbon atoms; a morpholine-1-yl group; a piperazine-1-yl group; halogen; a nitro group; and a cyano group.

Among $R^{b4}$, a benzoyl group; a naphthoyl group; a benzoyl groups substituted with a group selected from the group consisting of an alkyl group having 1 or more and 6 or less carbon atoms, a morpholine-1-yl group, a piperazine-1-yl group, and a phenyl group; and a nitro group are preferred, and a benzoyl group; a naphthoyl group; a 2-methylphenyl carbonyl group; a 4-(piperazine-1-yl) phenyl carbonyl group; and a 4-(phenyl) phenyl carbonyl group are more preferred.

In formula (b2), n3 is preferably an integer of 0 or more and 3 or less, more preferably an integer of 0 or more and 2 or less, and particularly preferably 0 or 1. When n3 is 1, the position at which $R^{b4}$ bonds is preferably the para-position to the bonding through which the phenyl group (to which $R^{b4}$ bonds) bonds to a oxygen atom or a sulfur atom.

$R^{b5}$ in the formula (b3) can be selected from various organic groups as long as they do not interfere with the object of the present invention. Suitable examples of $R^{b5}$ include an alkyl group having 1 or more and 20 or less carbon atoms, a cycloalkyl group having 3 or more and 10 or less carbon atoms, a saturated aliphatic acyl group having 2 or more and 20 or less carbon atoms, an alkoxycarbonyl group having 2 or more and 20 or less carbon atoms, an optionally substituted phenyl group, an optionally substituted benzoyl group, an optionally substituted phenoxycarbonyl group, an optionally substituted phenylalkyl group having 7 or more and 20 or less carbon atoms, an optionally substituted naphthyl group, an optionally substituted naphthoyl group, an optionally substituted naphthoxycarbonyl group, an optionally substituted naphthylalkyl group having 11 or more and 20 or less carbon atoms, an optionally substituted heterocyclyl group, an optionally substituted heterocyclylcarbonyl group, and the like.

Among $R^{b5}$, an alkyl group having 1 or more and 20 or less carbon atoms is preferred, an alkyl group having 1 or more and 6 or less carbon atoms is more preferred, and an ethyl group is particulary preferred.

There is no particular limitation for $R^{b6}$ in the formula (b3) as long as they do not interfere with the object of the present invention, and it can be selected from various organic groups. Specific examples of the suitable group for $R^{b6}$ include an alkyl group having 1 or more and 20 or less carbon atoms, an optionally substituted phenyl group, an optionally substituted naphthyl group and an optionally substituted heterocyclyl group. Among these groups, $R^{b6}$ is more preferably an optionally substituted phenyl group, and in particular preferably a 2-methylphenyl group.

when a phenyl group, a naphthyl group, and a heterocyclyl group included in $R^{b4}$, $R^{b5}$, or $R^{b6}$ further has a substituent, examples of the substituent include an alkyl group having 1 or more and 6 or less carbon atoms, an alkoxy group having 1 or more and 6 or less carbon atoms, a saturated aliphatic acyl group having 2 or more and 7 or less carbon atoms, an alkoxycarbonyl group having 2 or more and 7 or less carbon atoms, a saturated aliphatic acyloxy group having 2 or more and 7 or less carbon atoms, a monoalkylamino group having an alkyl group which has 1 or more and 6 or less carbon atoms, a dialkylamino group having an alkyl group which has 1 or more and 6 or less carbon atoms, a morpholin-1-yl group, a piperazin-1-yl group, halogen, a nitro group, and a cyano group. When the phenyl group, naphthyl group, and heterocyclyl group included in $R^{b4}$, $R^{b5}$, or $R^{b6}$ further has a substituent, the number of substituents is not particularly limited as long as it does not interfere with the object of the present invention, but is preferably 1 or more and 4 or less. When the phenyl group, naphthyl group, and heterocyclyl group included in $R^{b4}$, $R^{b5}$, or $R^{b6}$ further has plural substituents, plural substituents may be the same or different.

$R^{b3}$ in the formula (b1) is a hydrogen atom, or an alkyl group having 1 or more and 6 or less carbon atoms. $R^{b3}$ is preferably a methyl group or an ethyl group, and more preferably a methyl group.

Among the oxime ester compounds represented by the formula (b1), the particularly suitable compounds include the following PI-1 to PI-42:

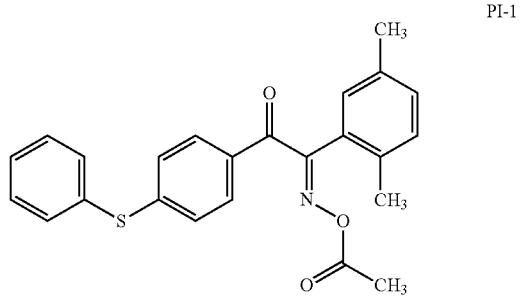

PI-1

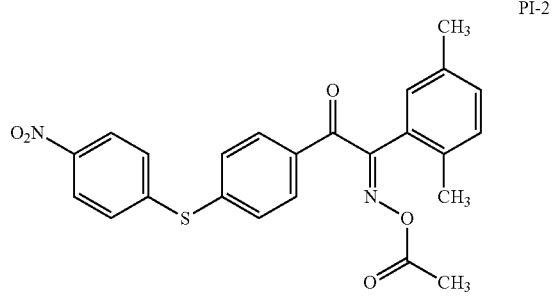

PI-2

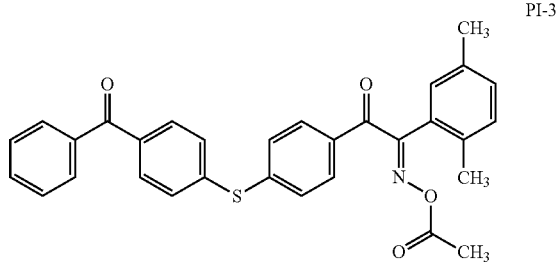

PI-3

-continued
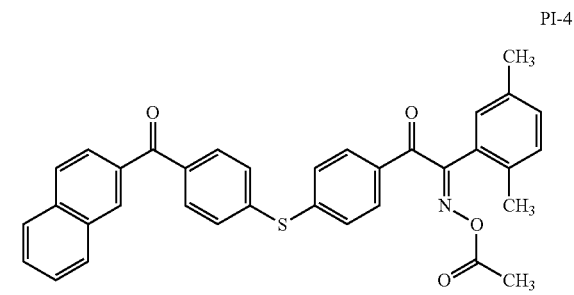
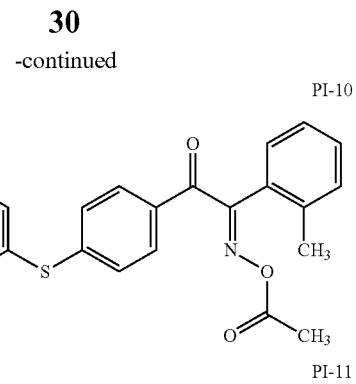

-continued
PI-16
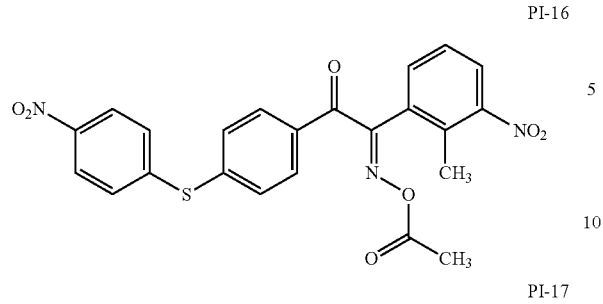
PI-23
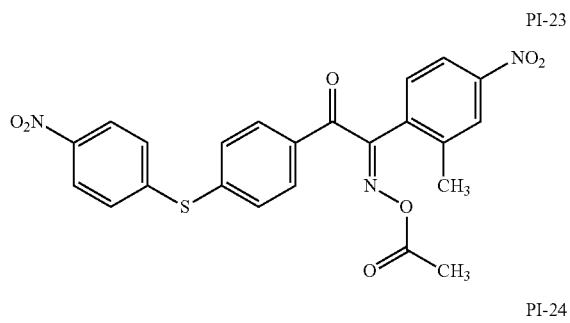
PI-17
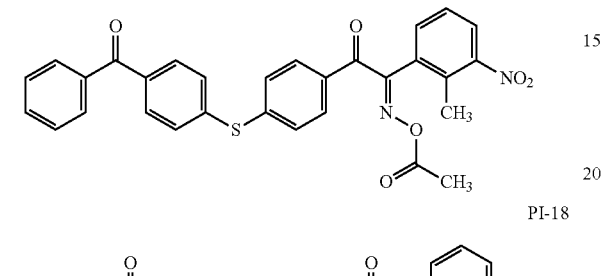
PI-24
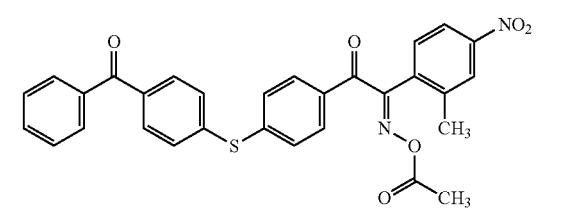
PI-18
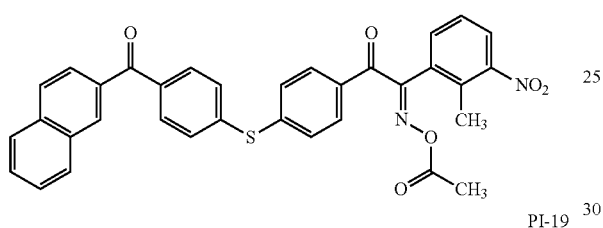
PI-25
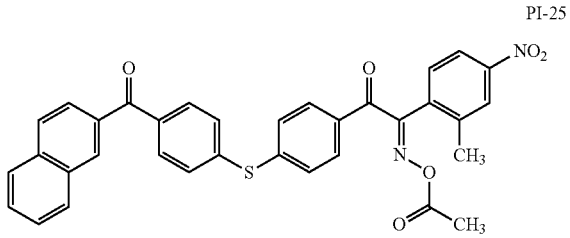
PI-19
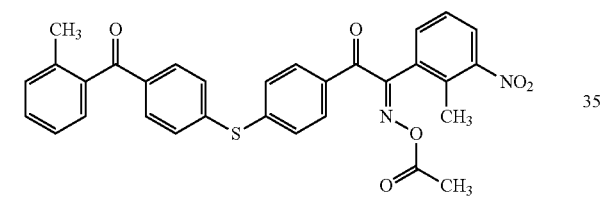
PI-26
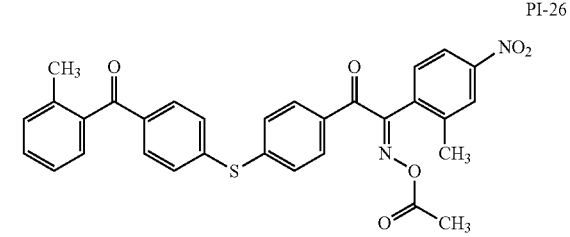
PI-20
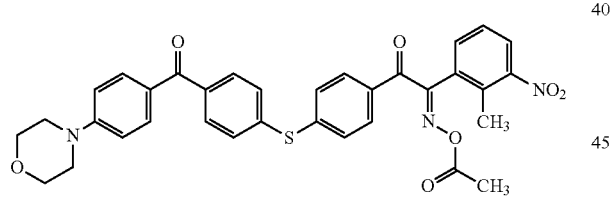
PI-27
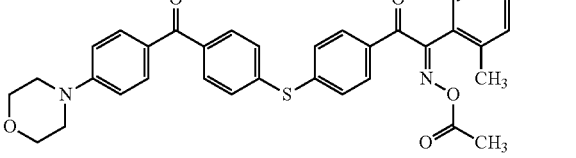
PI-21
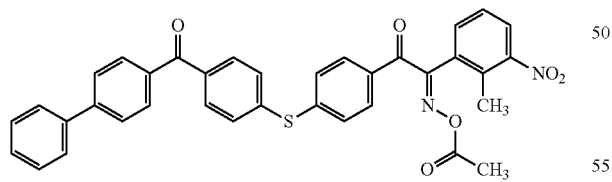
PI-22
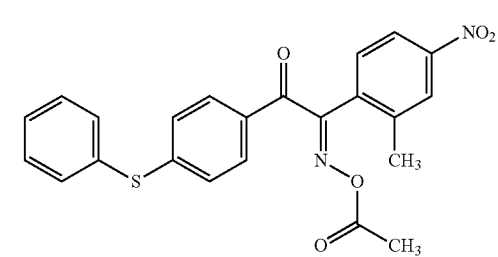
PI-28
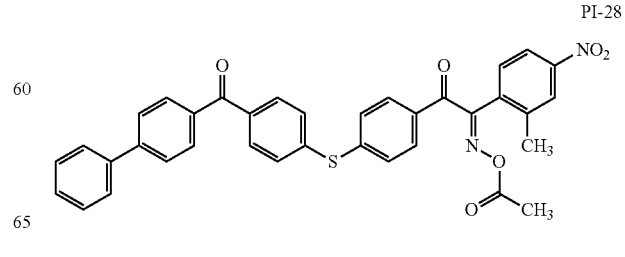

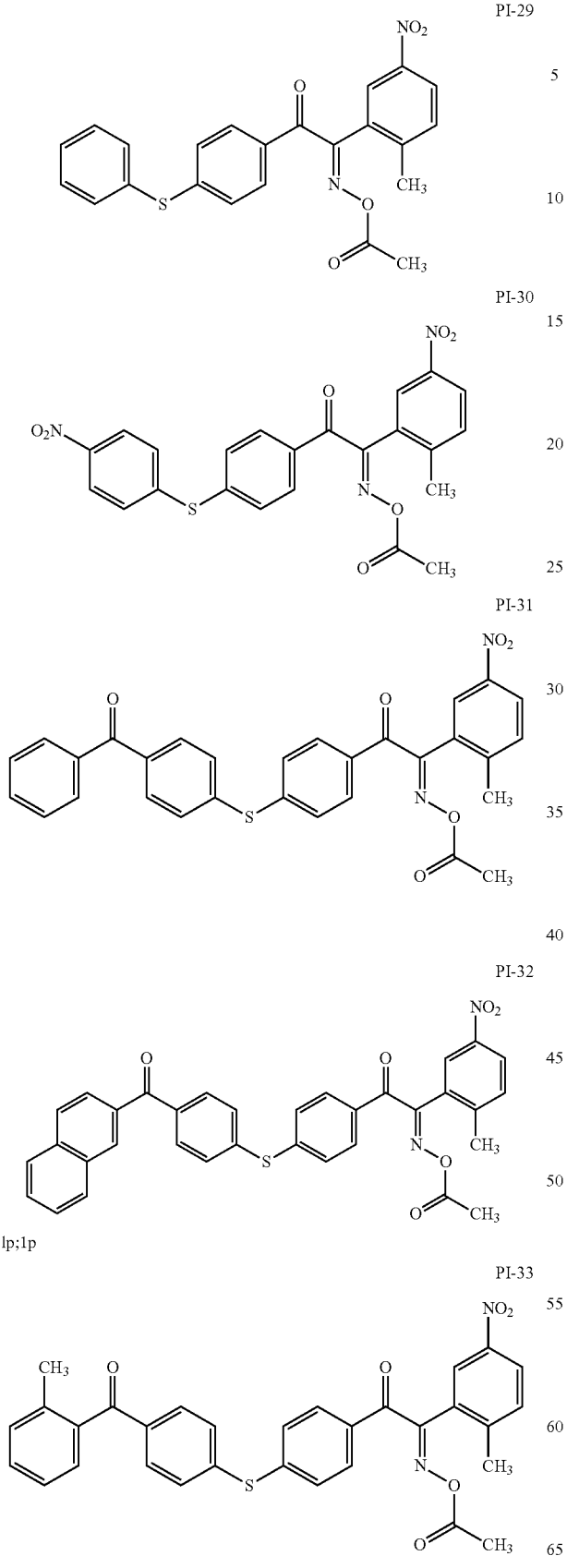
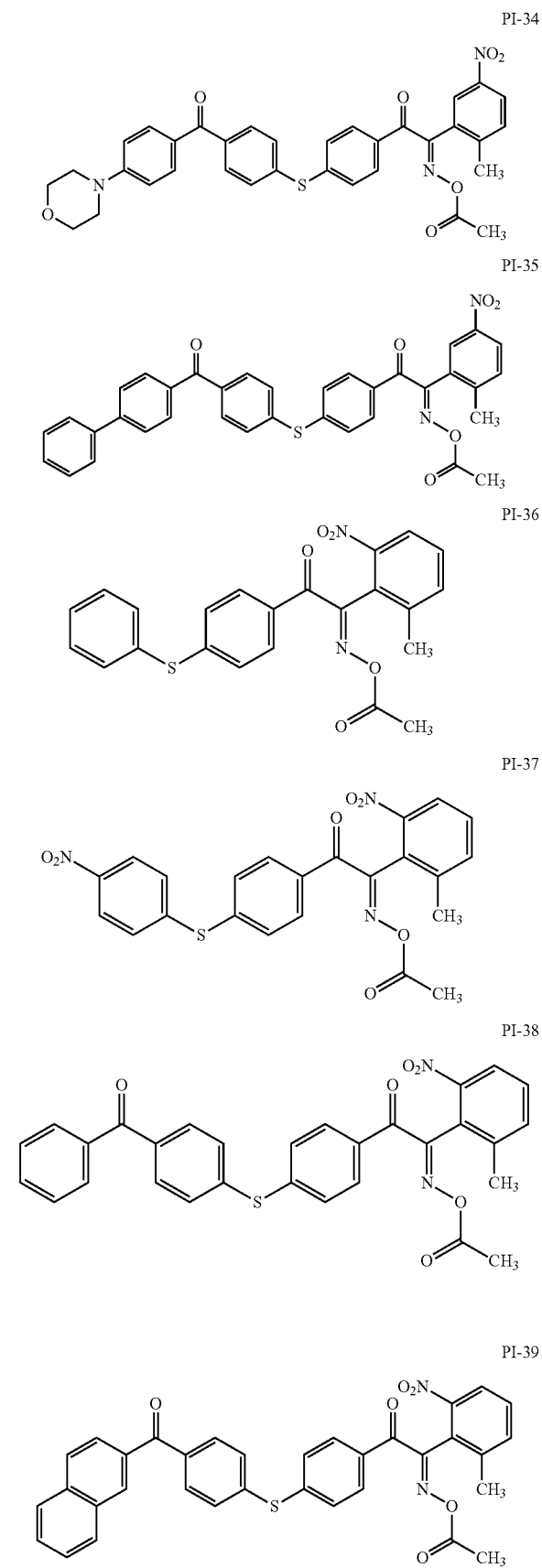

-continued

PI-40

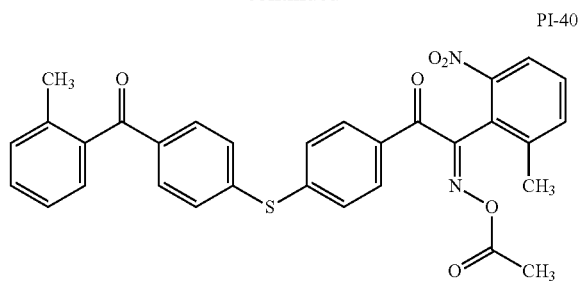

PI-41

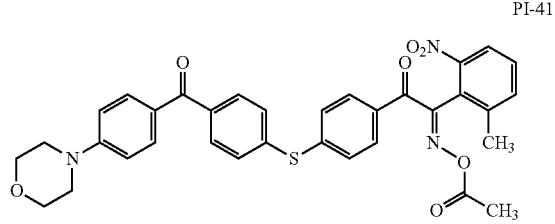

PI-42

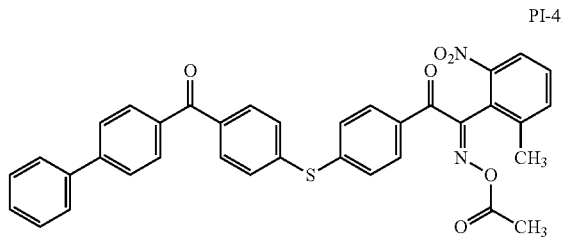

Also preferable as a photopolymerization initiator is an oxime ester compound represented by the following formula (b4).

(b4)

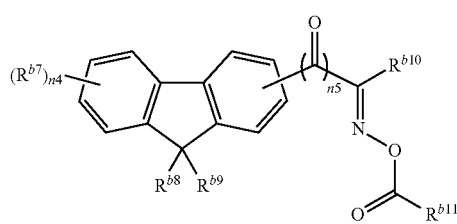

$R^{b7}$ is a hydrogen atom, a nitro group, or a monovalent organic group, $R^{b8}$ and $R^{b9}$ each represent an optionally substituted chain alkyl group, an optionally substituted cyclic organic group, or a hydrogen atom, $R^{b8}$ and $R^{b9}$ may be bonded to one another to form a ring, $R^{b10}$ is a monovalent organic group, $R^{b11}$ is a hydrogen atom, an optionally substituted alkyl group having 1 or more and 11 or less carbon atoms, or an optionally substituted aryl group, n4 is an integer of 0 or more and 4 or less, and n5 is 0 or 1.

An oxime compound for producing an oxime ester compound of the formula (b4) is suitably a compound represented by the following formula (b5).

(b5)

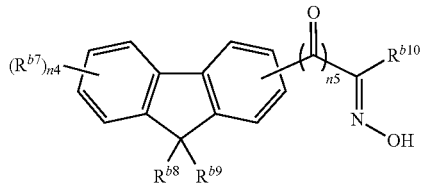

$R^{b7}$, $R^{b8}$, $R^{b9}$, $R^{b10}$, n4, and n5 are the same as defined in the formula (b4).

In the formula (b4) and (b5), $R^{b7}$ is a hydrogen atom, a nitro group, or a monovalent organic group. $R^{b7}$ is bonded to a 6-membered aromatic ring which is different from the 6-membered aromatic ring bonded to a group represented as —(CO)$_{n5}$— on a fluorene ring in the formula (b4). In the formula (b4), the bond position of $R^{b7}$ to a fluorene ring is not particularly limited. When a compound represented by the formula (b4) has 1 or more $R^{b7}$(s), one of the one or more $R^{b7}$(s) is preferably bonded at the 2-position in the fluorene ring since the synthesis of the compound represented by the formula (b4) becomes easy. When plural $R^{b7}$s exist, the plural $R^{b7}$s may be the same or different.

When $R^{b7}$ is an organic group, $R^{b7}$ is not particularly limited as long as it does not interfere with the object of the present invention, and is appropriately selected from various organic groups. When $R^{b7}$ is an organic group, suitable examples include an alkyl group, an alkoxy group, a cycloalkyl group, a cycloalkoxy group, a saturated aliphatic acyl group, a saturated aliphatic acyloxy group, an alkoxycarbonyl group, an optionally substituted phenyl group, an optionally substituted phenoxy group, an optionally substituted benzoyl group, an optionally substituted phenoxycarbonyl group, an optionally substituted benzoyloxy group, an optionally substituted phenylalkyl group, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group, an optionally substituted heterocyclyl group, an optionally substituted heterocyclylcarbonyl group, an amino group substituted with one or two organic groups, a morpholin-1-yl group, and a piperazin-1-yl group.

When $R^{b7}$ is an alkyl group, the number of carbon atoms of the alkyl group is preferably 1 or more and 20 or less, and more preferably 1 or more and 6 or less. When $R^{b7}$ is an alkyl group, the alkyl group may be either one of a straight chain or branched chain alkyl group. When $R^{b7}$ is an alkyl group, specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group, and the like. When $R^{b7}$ is an alkyl group, the alkyl group may contain an ether bond (—O—) in the carbon chain. Examples of the alkyl group having an ether bond in the carbon chain include a methoxyethyl group, an ethoxyethyl group, a methoxyethoxyethyl group, an ethoxyethoxyethyl group, a propyloxyethoxyethyl group, a methoxypropyl group, and the like.

When $R^{b7}$ is an alkoxy group, the number of carbon atoms of the alkoxy group is preferably 1 or more and 20 or less, and more preferably 1 or more and 6 or less. When $R^{67}$ is an alkoxy group, the alkoxy group may be a straight-chain or branched-chain group. When $R^{67}$ is an alkoxy group, specific examples thereof include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, and an isodecyloxy group. When $R^{67}$ is an alkoxy group, the alkoxy group may contain an ether bond (—O—) in the carbon chain. Examples of the alkoxy group having an ether bond in the carbon chain include a methoxyethoxy group, an ethoxyethoxy group, a methoxyethoxyethoxy group, an ethoxyethoxyethoxy group, a propyloxyethoxyethoxy group, and a methoxypropyloxy group.

When $R^{67}$ is a cycloalkyl group or a cycloalkoxy group, the number of carbon atoms of the cycloalkyl group or cycloalkoxy group is preferably 3 or more and 10 or less, and more preferably 3 or more and 6 or less. When $R^{67}$ is a cycloalkyl group, specific examples thereof include a cyclopropyl group, a cyclobutyl group, a cyclopentyl group, a cyclohexyl group, a cycloheptyl group, and a cyclooctyl group. When $R^{67}$ is a cycloalkoxy group, specific examples thereof include a cyclopropyloxy group, a cyclobutyloxy group, a cyclopentyloxy group, a cyclohexyloxy group, a cycloheptyloxy group, and a cyclooctyloxy group.

When $R^{67}$ is a saturated aliphatic acyl group or a saturated aliphatic acyloxy group, the number of carbon atoms of the saturated aliphatic acyl group or saturated aliphatic acyloxy group is preferably 2 or more and 21 or less, and more preferably 2 or more and 7 or less. When $R^{67}$ is a saturated aliphatic acyl group, specific examples thereof include an acetyl group, a propanoyl group, an n-butanoyl group, a 2-methylpropanoyl group, an n-pentanoyl group, a 2,2-dimethylpropanoyl group, an n-hexanoyl group, an n-heptanoyl group, an n-octanoyl group, an n-nonanoyl group, an n-decanoyl group, an n-undecanoyl group, an n-dodecanoyl group, an n-tridecanoyl group, an n-tetradecanoyl group, an n-pentadecanoyl group, and an n-hexadecanoyl group. When $R^{67}$ is a saturated aliphatic acyloxy group, specific examples thereof include an acetyloxy group, a propanoyloxy group, an n-butanoyloxy group, a 2-methylpropanoyloxy group, an n-pentanoyloxy group, a 2,2-dimethylpropanoyloxy group, an n-hexanoyloxy group, an n-heptanoyloxy group, an n-octanoyloxy group, an n-nonanoyloxy group, an n-decanoyloxy group, an n-undecanoyloxy group, an n-dodecanoyloxy group, an n-tridecanoyloxy group, an n-tetradecanoyloxy group, an n-pentadecanoyloxy group, and an n-hexadecanoyloxy group.

When $R^{67}$ is an alkoxycarbonyl group, the number of carbon atoms of the alkoxycarbonyl group is preferably 2 or more and 20 or less, and preferably 2 or more and 7 or less. When $R^{67}$ is an alkoxycarbonyl group, specific examples thereof include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an isopentyloxycarbonyl group, a sec-pentyloxycarbonyl group, a tert-pentyloxycarbonyl group, an n-hexyloxycarbonyl group, an n-heptyloxycarbonyl group, an n-octyloxycarbonyl group, an isooctyloxycarbonyl group, a sec-octyloxycarbonyl group, a tert-octyloxycarbonyl group, an n-nonyloxycarbonyl group, an isononyloxycarbonyl group, an n-decyloxycarbonyl group, and an isodecyloxycarbonyl group.

When $R^{67}$ is a phenylalkyl group, the number of carbon atoms of the phenylalkyl group is preferably 7 or more and 20 or less, and more preferably 7 or more and 10 or less. When $R^{67}$ is a naphthylalkyl group, the number of carbon atoms of the naphthylalkyl group is preferably 11 or more and 20 or less, and more preferably 11 or more and 14 or less. When $R^{67}$ is a phenylalkyl group, specific examples thereof include a benzyl group, a 2-phenylethyl group, a 3-phenylpropyl group, and a 4-phenylbutyl group. When $R^{67}$ is a naphthylalkyl group, specific examples thereof include an α-naphthylmethyl group, a β-naphthylmethyl group, a 2-(α-naphthyl)ethyl group, and a 2-(β-naphthyl)ethyl group. When $R^{67}$ is a phenylalkyl group or a naphthylalkyl group, $R^{67}$ may further have a substituent on a phenyl group or a naphthyl group.

When $R^{67}$ is a heterocyclylic group, the heterocyclylic group is a 5- or 6-membered single ring containing one or more N, S, and O, or a heterocyclylic group in which single rings are fused each other, or a single ring is fused with a benzene ring. When the heterocyclic group is a fused ring, the number of fused ring is 3 or less. The heterocyclic group may be any one of an aromatic group (heteroaryl group) and a non-aromatic group. Examples of the heterocycle constituting the heterocyclylic group include furan, thiophene, pyrrole, oxazole, isoxazole, thiazole, thiadiazole, isothiazole, imidazole, pyrazole, triazole, pyridine, pyrazine, pyrimidine, pyridazine, benzofuran, benzothiophene, indole, isoindole, indolizine, benzoimidazole, benzotriazole, benzoxazole, benzothiazole, carbazole, purine, quinoline, isoquinoline, quinazoline, phthalazine, cinnoline, quinoxaline, piperidine, piperazine, morpholine, piperidine, tetrahydropyran, and tetrahydrofuran. When $R^{67}$ is a heterocyclyl group, the heterocyclyl group may further have a substituent.

When $R^{67}$ is a heterocyclylcarbonyl group, a heterocyclyl group included in the heterocyclylcarbonyl group is the same as that in the case where $R^{67}$ is a heterocyclyl group.

When $R^{67}$ is an amino group substituted with one or two organic group(s), suitable examples of the organic group(s) include an alkyl group having 1 or more and 20 or less carbon atoms, a cycloalkyl group having 3 or more and 10 or less carbon atoms, a saturated aliphatic acyl group having 2 or more and 21 or less carbon atoms, an optionally substituted phenyl group, an optionally substituted benzoyl group, an optionally substituted phenylalkyl group having 7 or more and 20 or less carbon atoms, an optionally substituted naphthyl group, an optionally substituted naphthoyl group, an optionally substituted naphthylalkyl group having 11 or more 20 or less carbon atoms, and a heterocyclyl group. The specific examples of these suitable organic groups are the same as those of $R^{67}$. Specific examples of the amino group substituted with one or two organic groups include a methylamino group, an ethylamino group, a diethylamino group, an n-propylamino group, a di-n-propylamino group, an isopropylamino group, an n-butylamino group, a di-n-butylamino group, an n-pentylamino group, an n-hexylamino group, an n-heptylamino group, an n-octylamino group, an n-nonylamino group, an n-decylamino group, a phenylamino group, a naphthylamino group, an acetylamino group, a propanoylamino group, an n-butanoylamino group, an n-pentanoylamino group, an n-hexanoylamino group, an n-heptanoylamino group, an n-octanoylamino group, an n-decanoylamino group, an benzoylamino group, an α-naphthoylamino group, and a β-naphthoylamino group.

When the phenyl group, the naphthyl group, and the heterocyclyl group included in $R^{b7}$ further have a substituent, examples thereof include an alkyl group having 1 or more and 6 or less carbon atoms, an alkoxy group having 1 or more and 6 or less carbon atoms, a saturated aliphatic acyl group having 2 or more and 7 or less carbon atoms, an alkoxycarbonyl group having 2 or more and 7 or less carbon atoms, a saturated aliphatic acyloxy group having 2 or more and 7 or less carbon atoms, a monoalkylamino group having an alkyl group which has 1 or more and 6 or less carbon atoms, a dialkylamino group having an alkyl group which has 1 or more and 6 or less carbon atoms, a morpholin-1-yl group, a piperazin-1-yl group, halogen, a nitro group, and a cyano group. When a phenyl group, a naphthyl group, and a heterocyclyl group included in $R^{b7}$ further have substituents, the number of substituents is not particularly limited as long as it does not interfere with the object of the present invention, but is preferably 1 or more 4 or less. When a phenyl group, a naphthyl group, and a heterocyclyl group included in $R^{b7}$ have plural substituents, the plural substituents may be the same or different.

Among the above-described groups, $R^{b7}$ is preferably a nitro group or a group represented as $R^{b12}$—CO— since the sensitivity tends to be improved. $R^{b12}$ is not particularly limited as long as it does not interfere with the object of the present invention, and can be selected from various organic groups. Examples of the group suitable as $R^{b12}$ include an alkyl group having 1 or more and 20 or less carbon atoms, an optionally substituted phenyl group, an optionally substituted naphthyl group, and an optionally substituted heterocyclyl group. Among these groups, $R^{b12}$ is particularly preferably a 2-methylphenyl group, a thiophen-2-yl group, and an α-naphthyl group. Moreover, it is preferred that $R^{b7}$ is a hydrogen atom since the transparency tends to be satisfactory. When $R^{b7}$ is a hydrogen atom and $R^{b10}$ is a group represented by the formula (b4a) or (b4b) mentioned later, the transparency tends to be even more satisfactory.

In the formula (b4), $R^{b8}$ and $R^{b9}$ each represent an optionally substituted chain alkyl group, an optionally substituted cyclic organic group, or a hydrogen atom. $R^{b8}$ and $R^{b9}$ may be bonded to one another to form a ring. Among these, preferably, $R^{b8}$ and $R^{b9}$ are optionally substituted chain alkyl groups. When $R^{b8}$ and $R^{b9}$ are optionally substituted chain alkyl groups, a chain alkyl group may be either a straight-chain alkyl group or a branched-chain alkyl group.

When $R^{b8}$ and $R^{b9}$ are chain alkyl groups having no substituent, the number of carbon atoms of the chain alkyl group is preferably 1 or more and 20 or less, more preferably 1 or more and 10 or less, and particularly preferably 1 or more and 6 or less. When $R^{b8}$ and $R^{b9}$ are chain alkyl groups, specific examples thereof include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, and an isodecyl group. When $R^{b8}$ and $R^{b9}$ are alkyl groups, the alkyl group may have an ether bond (—O—) in a carbon chain. Examples of the alkyl group having an ether bond in a carbon chain include a methoxyethyl group, an ethoxyethyl group, a methoxyethoxyethyl group, an ethoxyethoxyethyl group, a propyloxyethoxyethyl group, and a methoxypropyl group.

When $R^{b8}$ and $R^{b9}$ are chain alkyl groups having a substituent, the number of carbon atoms of the chain alkyl group is preferably 1 or more and 20 or less, more preferably 1 or more and 10 or less, and particularly preferably 1 or more and 6 or less. In this case, the number of carbon atoms of the substituent is not included in the number of carbon atoms of the chain alkyl group. The chain alkyl group having a substituent is preferably a straight-chain group. The substituent, with which the alkyl group is optionally substituted, is not particularly limited as long as it does not interfere with the object of the present invention. Suitable examples of the substituent include a cyano group, a halogen atom, a cyclic organic group, and an alkoxycarbonyl group. Examples of the halogen atom include a fluorine atom, a chlorine atom, a bromine atom, and an iodine atom. Among these, a fluorine atom, a chlorine atom, and a bromine atom are preferable. Examples of the cyclic organic group include a cycloalkyl group, an aromatic hydrocarbon group, and a heterocyclyl group. Specific examples of the cycloalkyl group are the same as suitable examples in case $R^{b7}$ is a cycloalkyl group. Specific examples of the aromatic hydrocarbon group include a phenyl group, a naphthyl group, a biphenylyl group, an anthryl group, and a phenanthryl group. Specific examples of the heterocyclyl group are the same as suitable examples in case $R^{b7}$ is a heterocyclyl group. When $R^{b7}$ is an alkoxycarbonyl group, an alkoxy group included in the alkoxycarbonyl group may be either a straight-chain or branched-chain group, and preferably a straight-chain group. The number of carbon atoms of an alkoxy group included in the alkoxycarbonyl group is preferably 1 or more and 10 or less, and more preferably 1 or more and 6 or less.

When the chain alkyl group has a substituent, the number of substituents is not particularly limited. The number of substituents preferably varies depending on the number of carbon atoms of the chain alkyl group. The number of substituents is typically 1 or more and 20 or less, preferably 1 or more and 10 or less, and more preferably 1 or more and 6 or less.

When $R^{b8}$ and $R^{b9}$ are cyclic organic groups, and the cyclic organic group may be either an alicyclic group or an aromatic group. Examples of the cyclic organic group include an aliphatic cyclic hydrocarbon group, an aromatic hydrocarbon group, and a heterocyclyl group. When $R^{b8}$ and $R^{b9}$ are cyclic organic groups, the substituent, with which the cyclic organic group is optionally substituted, is the same as in case $R^{b8}$ and $R^{b9}$ are chain alkyl groups.

When $R^{b8}$ and $R^{b9}$ are aromatic hydrocarbon groups, the aromatic hydrocarbon group is preferably a phenyl group, or a group formed by bonding plural benzene rings through a carbon-carbon bond, or a group formed by condensing plural benzene rings. When the aromatic hydrocarbon group is a phenyl group, or a group formed by bonding or condensing plural benzene rings, the number of rings of a benzene ring included in the aromatic hydrocarbon group is not particularly limited, and is preferably 3 or less, more preferably 2 or less, and particularly preferably 1. Preferred specific examples of the aromatic hydrocarbon group include a phenyl group, a naphthyl group, a biphenylyl group, an anthryl group, and a phenanthryl group.

When $R^{b8}$ and $R^{b9}$ are aliphatic cyclic hydrocarbon groups, the aliphatic cyclic hydrocarbon group may be either a monocyclic or polycyclic group. The number of carbon atoms of the aliphatic cyclic hydrocarbon group is not particularly limited, and is preferably 3 or more 20 or less, and more preferably 3 or more and 10 or less. Examples of the monocyclic cyclic hydrocarbon group include cyclopropyl group, a cyclobutyl group, a cyclopentyl group, a cyclohexyl group, a cycloheptyl group, a cyclooctyl group, a norbornyl group, a isobornyl group, a tricyclononyl group, a tricyclodecyl group, a tetracyclododecyl group, and an adamantyl group.

When $R^{b8}$ and $R^{b9}$ are heterocyclyl groups, the heterocyclyl group is a 5-membered or 6-membered monocycle containing one or more N, S, and O, or a heterocyclyl group in which these monocycles are condensed, or the monocycle and a benzene ring are condensed. When the heterocyclyl group is a condensation ring, the number of rings is 3 or less. The heterocyclyl group may be either an aromatic group (heteroaryl group) or a non-aromatic group. Examples of the heterocycle constituting the heterocyclylic group include furan, thiophene, pyrrole, oxazole, isoxazole, thiazole, thiadiazole, isothiazole, imidazole, pyrazole, triazole, pyridine, pyrazine, pyrimidine, pyridazine, benzofuran, benzothiophene, indole, isoindole, indolizine, benzoimidazole, benzotriazole, benzoxazole, benzothiazole, carbazole, purine, quinoline, isoquinoline, quinazoline, phthalazine, cinnoline, quinoxaline, piperidine, piperazine, morpholine, piperidine, tetrahydropyran, and tetrahydrofuran.

$R^{b8}$ and $R^{b9}$ may be bonded to one another to form a ring. The group composed of the ring formed by $R^{b8}$ and $R^{b9}$ is preferably a cycloalkylidene group. When $R^{b8}$ and $R^{b9}$ are bonded to form a cycloalkylidene group, the ring constituting the cycloalkylidene group is preferably a 5- to 6-membered ring, and more preferably a 5-membered ring.

When the group formed by bonding $R^{b8}$ and $R^{b9}$ is a cycloalkylidene group, the cycloalkylidene group may be fused with one or more other rings. Examples of the ring which may be fused with the cycloalkylidene group include a benzene ring, a naphthalene ring, a cyclobutane ring, a cyclopentane ring, a cyclohexane ring, a cycloheptane ring, a cyclooctane ring, a furan ring, a thiophene ring, a pyrrole ring, a pyridine ring, a pyrazine ring, a pyrimidine ring, and the like.

Examples of suitable group among $R^{b8}$ and $R^{b9}$ desried above include a group represented by the formula: $-A^1-A^2$. In the formula, $A^1$ is a straight chain alkylene group, and $A^2$ is an alkoxy group, a cyano group, a halogen atom, a halogenated alkyl group, a cyclic organic group, or an alkoxycarbonyl group.

The number of carbon atoms of the straight chain alkylene group for $A^1$ is preferably 1 or more and 10 or less, and more preferably 1 or more and 6 or less. When $A^2$ is an alkoxy group, the alkoxy group may be any one of straight chain and branched chain alkoxy groups, and preferably a straight chain alkoxy group. The number of carbon atoms of the alkoxy group is preferably 1 or more and 10 or less, and more preferably 1 or more and 6 or less. When $A^2$ is a halogen atom, a fluorine atom, a chlorine atom, a bromine atom, or an iodine atom is preferable, and a fluorine atom, a chlorine atom, or a bromine atom is more preferable. When $A^2$ is a halogenated alkyl group, a halogen atom included in the halogenated alykyl group is preferably a fluorine atom, a chlorine atom, a bromine atom, or an iodine atom, and more preferably is a fluorine atom, a chlorine atom, or a bromine atom. The halogenated alkyl group may be any one of straight chain and branched chain halogenated alkyl groups, and preferably a straight chain halogenated alkyl group. When $A^2$ is a cyclic organic group, examples of the cyclic organic group are the same as the cyclic organic group possessed by $R^{b8}$ and $R^{b9}$ as the substituent. When $A^2$ is an alkoxycarbonyl group, examples of the alkoxycarbonyl group are the same as the alkoxycarbonyl group possessed by $R^{b8}$ and $R^{b9}$ as the substituent.

Suitable specific examples of $R^{b8}$ and $R^{b9}$ include alkyl groups such as an ethyl group, an n-propyl group, an n-butyl group, an n-hexyl group, an n-heptyl group, and an n-octyl group; alkoxyalkyl groups such as a 2-methoxyethyl group, a 3-methoxy-n-propyl group, a 4-methoxy-n-butyl group, a 5-methoxy-n-pentyl group, a 6-methoxy-n-hexyl group, a 7-methoxy-n-heptyl group, a 8-methoxy-n-octyl group, a 2-ethoxyethyl group, a 3-ethoxy-n-propyl group, a 4-ethoxy-n-butyl group, a 5-ethoxy-n-pentyl group, a 6-ethoxy-n-hexyl group, a 7-ethoxy-n-heptyl group, and a 8-ethoxy-n-octyl group; cyanoalkyl groups such as a 2-cyanoethyl group, a 3-cyano-n-propyl group, a 4-cyano-n-butyl group, a 5-cyano-n-pentyl group, a 6-cyano-n-hexyl group, a 7-cyano-n-heptyl group, and a 8-cyano-n-octyl group; phenylalkyl groups such as a 2-phenylethyl group, a 3-phenyl-n-propyl group, a 4-phenyl-n-butyl group, a 5-phenyl-n-pentyl group, a 6-phenyl-n-hexyl group, a 7-phenyl-n-heptyl group, and a 8-phenyl-n-octyl group; cycloalkylalkyl groups such as a 2-cyclohexylethyl group, a 3-cyclohexyl-n-propyl group, a 4-cyclohexyl-n-butyl group, a 5-cyclohexyl-n-pentyl group, a 6-cyclohexyl-n-hexyl group, a 7-cyclohexyl-n-heptyl group, a 8-cyclohexyl-n-octyl group, a 2-cyclopentylethyl group, a 3-cyclopentyl-n-propyl group, a 4-cyclopentyl-n-butyl group, a 5-cyclopentyl-n-pentyl group, a 6-cyclopentyl-n-hexyl group, a 7-cyclopentyl-n-heptyl group, and a 8-cyclopentyl-n-octyl group; alkoxycarbonylalkyl groups such as a 2-methoxycarbonylethyl group, a 3-methoxycarbonyl-n-propyl group, a 4-methoxycarbonyl-n-butyl group, a 5-methoxycarbonyl-n-pentyl group, a 6-methoxycarbonyl-n-hexyl group, a 7-methoxycarbonyl-n-heptyl group, a 8-methoxycarbonyl-n-octyl group, a 2-ethoxycarbonylethyl group, a 3-ethoxycarbonyl-n-propyl group, a 4-ethoxycarbonyl-n-butyl group, a 5-ethoxycarbonyl-n-pentyl group, a 6-ethoxycarbonyl-n-hexyl group, a 7-ethoxycarbonyl-n-heptyl group, and a 8-ethoxycarbonyl-n-octyl group; and halogenated alkyl groups such as a 2-chloroethyl group, a 3-chloro-n-propyl group, a 4-chloro-n-butyl group, a 5-chloro-n-pentyl group, a 6-chloro-n-hexyl group, a 7-chloro-n-heptyl group, a 8-chloro-n-octyl group, a 2-bromoethyl group, a 3-bromo-n-propyl group, a 4-bromo-n-butyl group, a 5-bromo-n-pentyl group, a 6-bromo-n-hexyl group, a 7-bromo-n-heptyl group, a 8-bromo-n-octyl group, a 3,3,3-trifluoropropyl group, and a 3,3,4,4,5,5,5-heptafluoro-n-pentyl group.

Among groups mentioned above, groups suitable as $R^{b8}$ and $R^{b9}$ are an ethyl group, an n-propyl group, an n-butyl group, an n-pentyl group, a 2-methoxyethyl group, a 2-cyanoethyl group, a 2-phenylethyl group, a 2-cyclohexylethyl group, a 2-methoxycarbonylethyl group, a 2-chloroethyl group, a 2-bromoethyl group, a 3,3,3-trifluoropropyl group, and a 3,3,4,4,5,5,5-heptafluoro-n-pentyl group.

In the same manner as $R^{b7}$, examples of suitable organic group for $R^{b10}$ include an alkyl group, an alkoxy group, a cycloalkyl group, a cycloalkoxy group, a saturated aliphatic acyl group, an alkoxycarbonyl group, a saturated aliphatic acyloxy group, a phenyl group which may have a substituent, a phenoxy group which may have a substituent, a benzoyl group which may have a substituent, a phenoxycarbonyl group which may have a substituent, a benzoyloxy group which may have a substituent, a phenylalkyl group which may have a substituent, a naphthyl group which may have a substituent, a naphthoxy group which may have a substituent, a naphthoyl group which may have a substituent, a naphthoxycarbonyl group which may have a substituent, a naphthoyloxy group which may have a substituent, a naphthylalkyl group which may have a substituent, a heterocyclylic group which may have a substituent, a heterocyclylcarbonyl group which may have a substituent, an amino group substituted with one or two organic groups, a morpholin-1-yl group, a piperazin-1-yl group, and the like. Specific examples of these groups are the same as those described for $R^{b7}$. $R^{b10}$ is also preferably a cycloalkylalkyl group, a phenoxyalkyl group which may have a substituent on an aromatic ring, and a phenylthioalkyl group which may have a substituent on an aromatic ring. The substituent which may be possessed by a phenoxyalkyl group and phenylthioalkyl group is the same as the substituent which may be possessed by a phenyl group included in $R^{b7}$.

Among organic groups, $R^{b10}$ is preferably an alkyl group, a cycloalkyl group, a phenyl group which may have a substituent or cycloalkylalkyl group, or a phenylthioalkyl group which may have a substituent on an aromatic ring. The alkyl group is preferably an alkyl group having 1 or more and 20 or less carbon atoms, more preferably, an alkyl group having 1 or more and 8 or less carbon atoms, particularly preferably, an alkyl group having 1 or more and 4 or less carbon atoms, and most preferably a methyl group. Among phenyl groups which may have a substituent, a methylphenyl group is preferable and a 2-methylphenyl group is more preferable. The number of carbon atoms of the cycloalkyl group included in the cycloalkylalkyl group is preferably 5 or more and 10 or less, more preferably 5 or more and 8 or less, and particularly preferably 5 or 6. The number of carbon atoms of the alkylene group included in the cycloalkylalkyl group is preferably 1 or more and 8 or less, more preferably 1 or more and 4 or less, and particularly preferably 2. Among cycloalkylalkyl groups, a cyclopentylethyl group is preferable. The number of carbon atoms of the alkylene group which may have a substituent on an aromatic ring included in the phenylthioalkyl group, is preferably 1 or more and 8 or less, more preferably 1 or more and 4 or less, and particularly preferably 2. Among the phenylthioalkyl group which may have a substituent on an aromatic ring, a 2-(4-chlorophenylthio)ethyl group is preferable.

$R^{b10}$ is also preferably a group represented by -$A^3$-CO—O-$A^4$. $A^3$ is a divalent organic group, preferably a divalent hydrocarbon group, and more preferably an alkylene group. $A^4$ is a monovalent organic group, and preferably a monovalent hydrocarbon group.

When $A^3$ is an alkylene group, alkylene group may be any one of straight chain and branched chain alkylene groups, and preferably a straight chain alkylene group. When $A^3$ is an alkylene group, the number of carbon atoms of the alkylene group is preferably 1 or more and 10 or less, more preferably 1 or more and 6 or less, and particularly preferably 1 or more and 4 or less.

Suitable examples of $A^4$ include an alkyl group having 1 or more and 10 or less carbon atoms, an aralkyl group having 7 or more and 20 or less carbon atoms, and an aromatic hydrocarbon group having 6 or more and 20 or less carbon atoms. Suitable specific examples of $A^4$ include a methyl group, an ethyl group, an n-propyl group, an isopropyl group, an n-butyl group, an isobutyl group, a sec-butyl group, an tert-butyl group, an n-pentyl group, an n-hexyl group, a phenyl group, a naphthyl group, a benzyl group, a phenethyl group, an α-naphthylmethyl group, a β-naphthylmethyl group, and the like.

Suitable specific examples of the group represented by -$A^3$-CO—O-$A^4$ include a 2-methoxycarbonylethyl group, a 2-ethoxycarbonylethyl group, a 2-n-propyloxycarbonylethyl group, a 2-n-butyloxycarbonylethyl group, a 2-n-pentyloxycarbonylethyl group, a 2-n-hexyloxycarbonylethyl group, a 2-benzyloxycarbonylethyl group, a 2-phenoxycarbonylethyl group, a 3-methoxycarbonyl-n-propyl group, a 3-ethoxycarbonyl-n-propyl group, a 3-n-propyloxycarbonyl-n-propyl group, a 3-n-butyloxycarbonyl-n-propyl group, a 3-n-pentyloxycarbonyl-n-propyl group, a 3-n-hexyloxycarbonyl-n-propyl group, a 3-benzyloxycarbonyl-n-propyl group, a 3-phenoxycarbonyl-n-propyl group, and the like.

While $R^{b10}$ has been described above, $R^{b10}$ is preferably a group represented by the following formula (b4a) or (b4b):

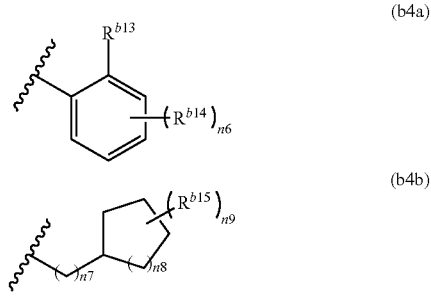

in which, in the formulas (b4a) and (b4b), $R^{b13}$ and $R^{b14}$ each are an organic group, n6 is an integer of 0 or more and 4 or less; when $R^{b13}$ and $R^{b14}$ exist at adjacent positions on a benzene ring, $R^{b13}$ and $R^{b14}$ may be bonded to one another to form a ring; n7 is an integer of 1 or more and 8 or less; n8 is an integer of 1 or more and 5 or less; n9 is an integer of 0 or more and (n8+3); and $R^{b15}$ is an organic group.

Examples of the organic group for $R^{b13}$ and $R^{b14}$ in the formula (b4a) are the same as those in $R^{b7}$. $R^{b13}$ is preferably an alkyl group or a phenyl group. When $R^{b13}$ is an alkyl group, the number of carbon atoms thereof is preferably 1 or more and 10 or less, more preferably 1 or more and 5 or less, preferably 1 or more and 3 or less, and most preferably 1. Namely, $R^{b13}$ is most preferably a methyl group. When $R^{b13}$ and $R^{b14}$ are bonded to form a ring, the ring may be either one of an aromatic ring or an aliphatic ring. Suitable examples of the group represented by the formula (b4a) in which $R^{b13}$ and $R^{b14}$ form a ring include a naphthalen-1-yl group, a 1,2,3,4-tetrahydronaphthalen-5-yl group, and the like. In the above formula (b4a), n6 is an integer of 0 or more and 4 or less, preferably 0 or 1, and more preferably 0.

In the above formula (b4b), $R^{b15}$ is an organic group. Examples of the organic group include the same group as the organic group described for $R^{b7}$. Among the organic groups, an alkyl group is preferable. The alkyl group may be any one of straight chain and branched chain alkyl groups. The number of carbon atoms of the alkyl group is preferably 1 or more and 10 or less, more preferably, 1 or more and 5 or less, and particularly preferably 1 or more and 3 or less. Preferable examples of $R^{b15}$ include a methyl group, an ethyl group, a propyl group, an isopropyl group, a butyl group, and the like. Among these, a methyl group is more preferable.

In the above formula (b4b), n8 is an integer of 1 or more and 5 or less, preferably 1 or more and 3 or less, and more preferably 1 or 2. In the formula (b4b), n9 is 0 or more and (n8+3) or less, preferably an integer of 0 or more and 3 or less, more preferably an integer of 0 or more and 2 or less, and particularly preferably 0. In the formula (b4b), n7 is an integer of 1 or more and 8 or less, preferably an integer of 1 or more and 5 or less, more preferably an integer of 1 or more and 3 or less, and particularly preferably 1 or 2.

In the formula (b4), $R^{b11}$ is a hydrogen atom, an alkyl group having 1 or more and 11 or less carbon atoms which may have a substituent, or an aryl group which may have a substituent. When $R^{b11}$ is an alkyl group, preferable examples of the substituent which may be possessed include a phenyl group, a naphthyl group, or the like. When $R^{b7}$ is an aryl group, preferable examples of the substituent which may be possessed include an alkyl group having 1 or more and 5 or less carbon atoms, an alkoxy group, a halogen atom, or the like.

In the formula (b4), preferable examples of $R^{b11}$ include a hydrogen atom, a methyl group, an ethyl group, an n-propyl group, an isopropyl group, an n-butyl group, a phenyl group, a benzyl group, a methylphenyl group, a naphthyl group, and the like. Among these, a methyl group or a phenyl group is more preferable.

The compound represented by the formula (b4) is produced by a method including the step of converting an oxime group (>C=N—OH) contained in a compound represented by the formula (b5) into an oxime ester group represented by >C=N—O—COR$^{b11}$. $R^{b11}$ is the same as $R^{b11}$ in the formula (b4).

Conversion of the oxime group (>C=N—OH) into the oxime ester group represented by >C=N—O—COR$^{b11}$ is performed by reacting a compound represented by the formula (b5) with an acylating agent. Examples of the acylating agent, which imparts an acyl group represented by —COR$^{b11}$, include an acid anhydride represented by $(R^{b11}CO)_2O$, and an acid halide represented by $R^{b11}COHal$ (Hal is a halogen atom).

Suitable specific examples of the compound represented by the formula (b4) include the following PI-43 to PI-83.

PI-43

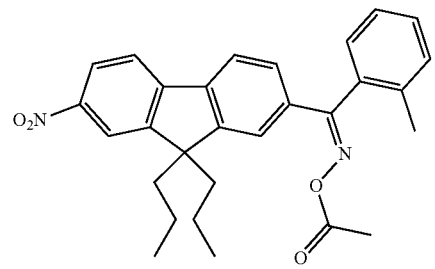

PI-44

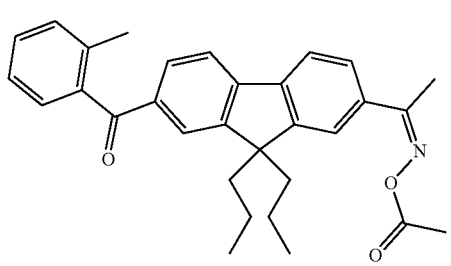

PI-45

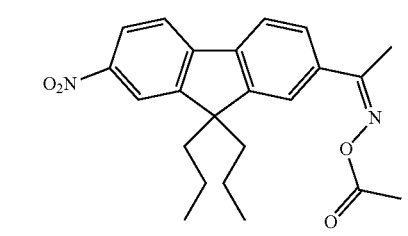

-continued

PI-46

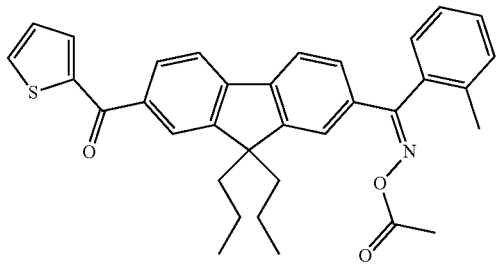

PI-47

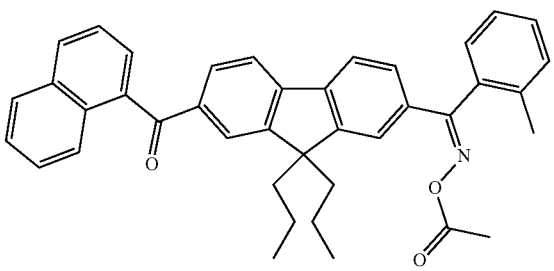

PI-48

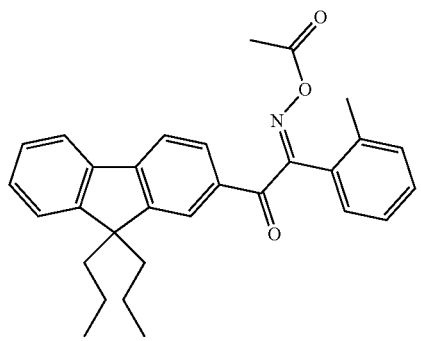

PI-49

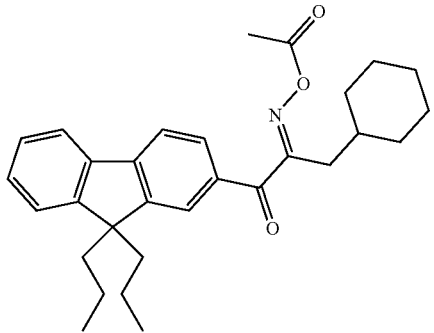

PI-50

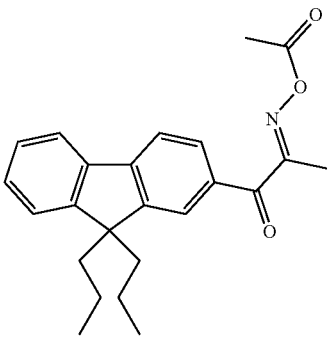

PI-51
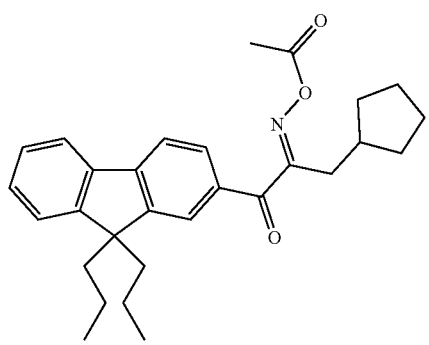
PI-55
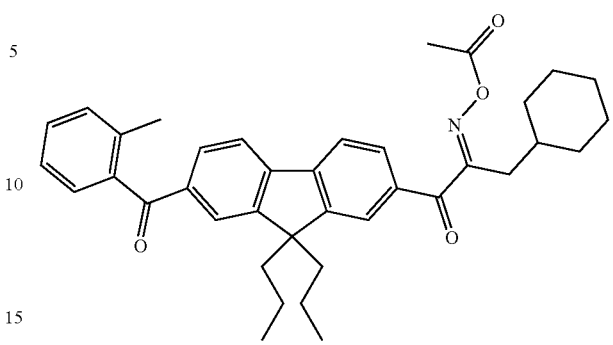
PI-52
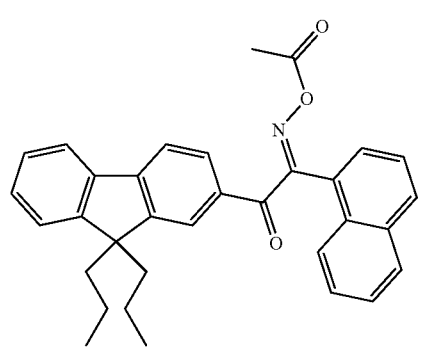
PI-56
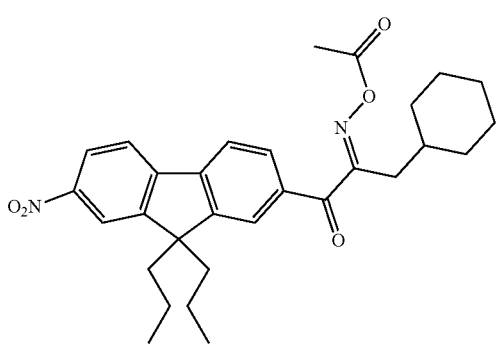
PI-53
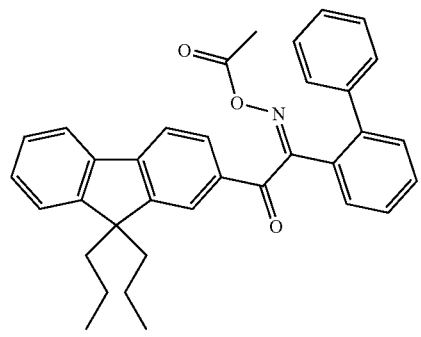
PI-57
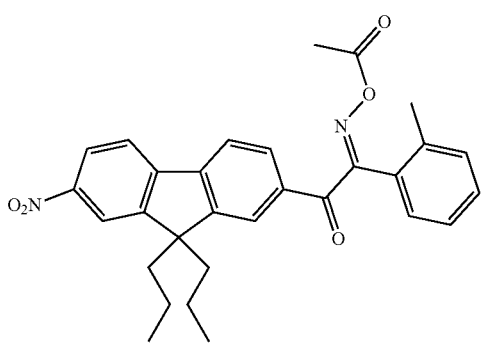
PI-54
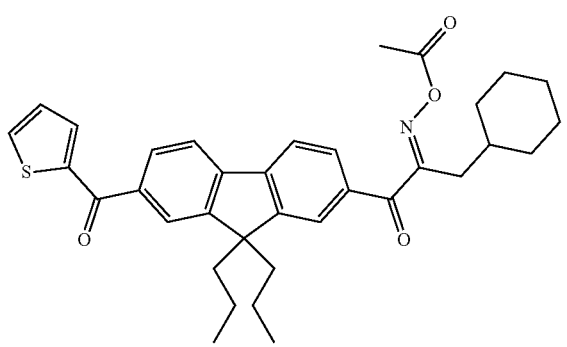
PI-58
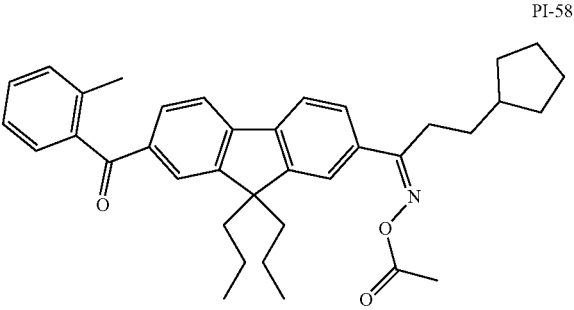

-continued
PI-59
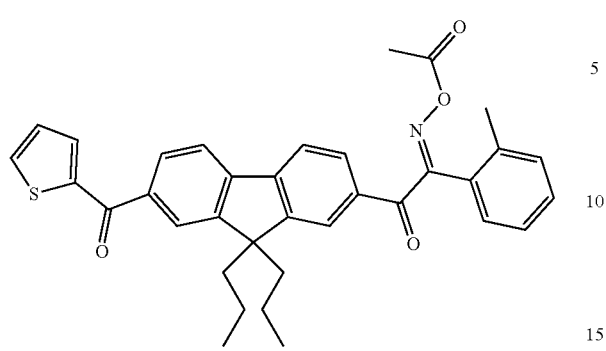
PI-63
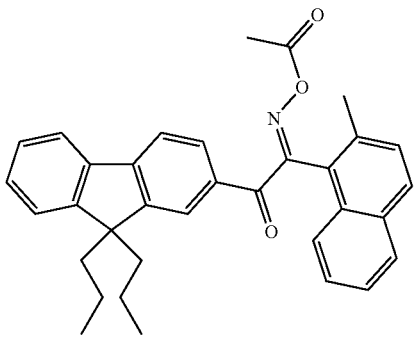
PI-60
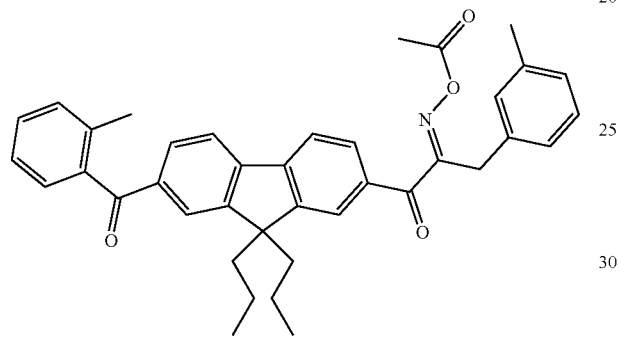
PI-64
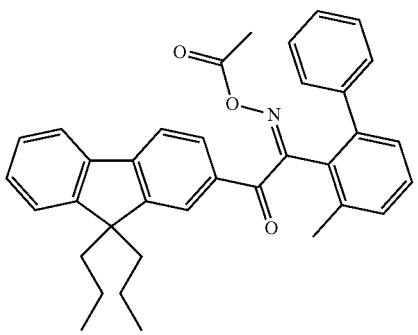
PI-61
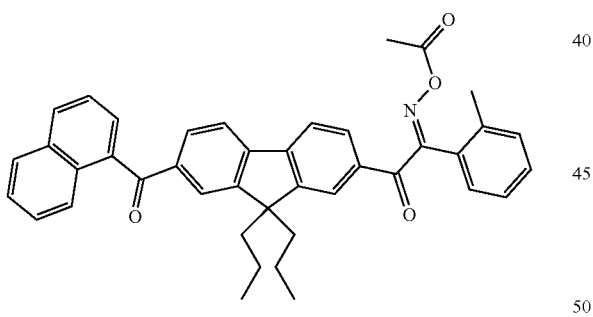
PI-65
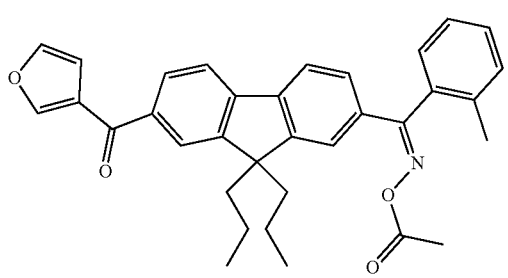
PI-62
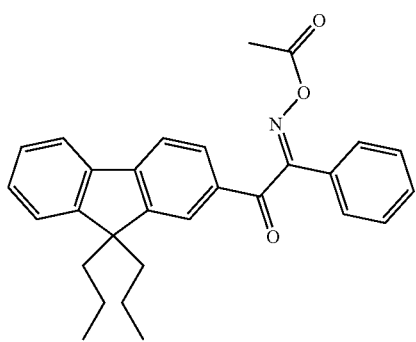
PI-66
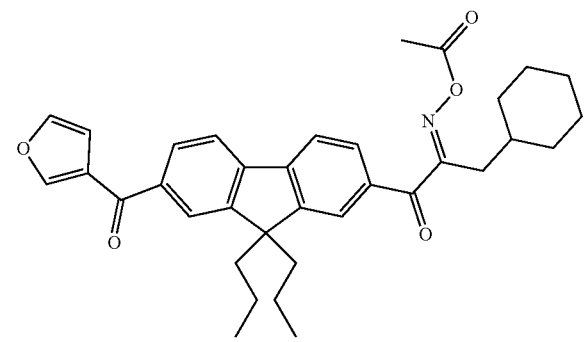

-continued
PI-67
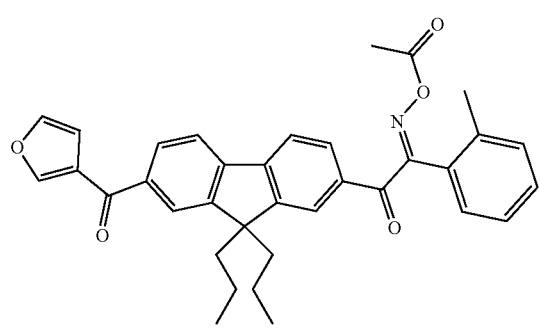
PI-68
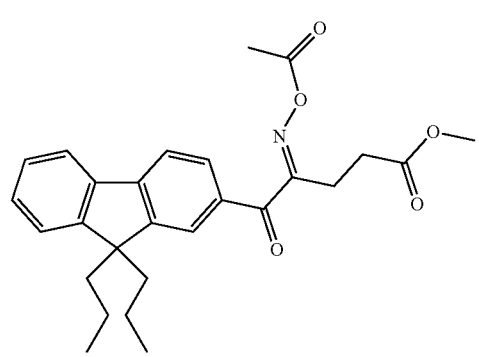
PI-69
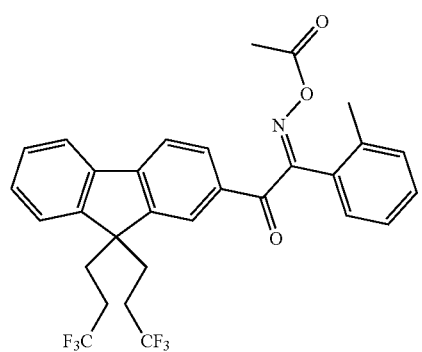
PI-70
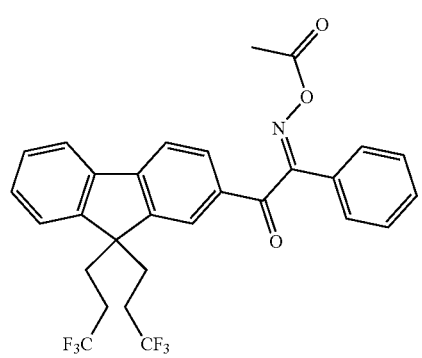
-continued
PI-71
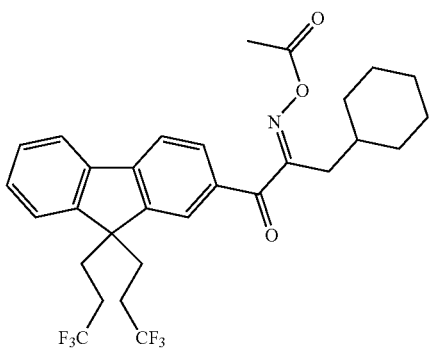
PI-72
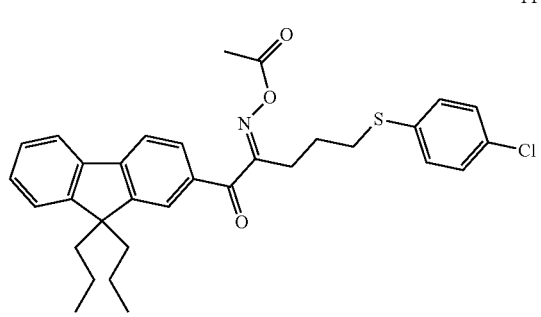
PI-73
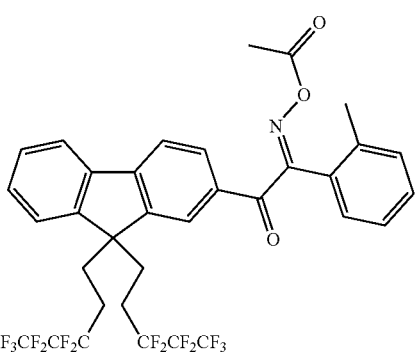
PI-74
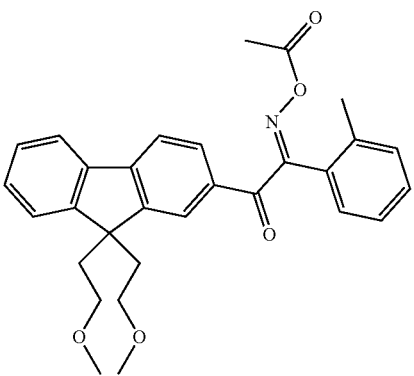

PI-75
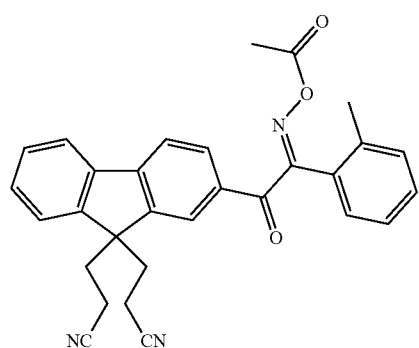
PI-76
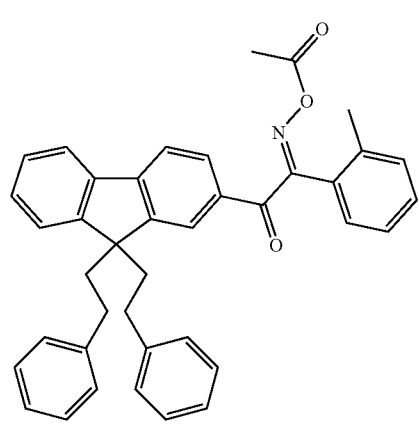
PI-77
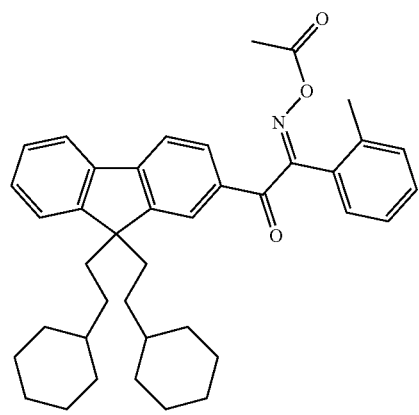
PI-78
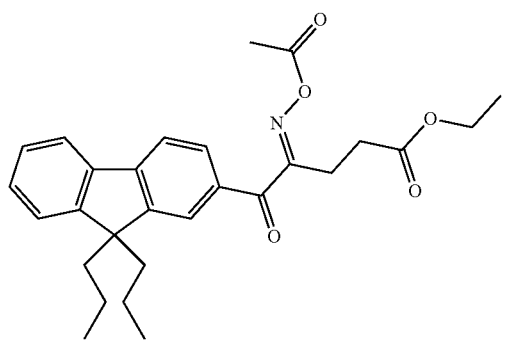
PI-79
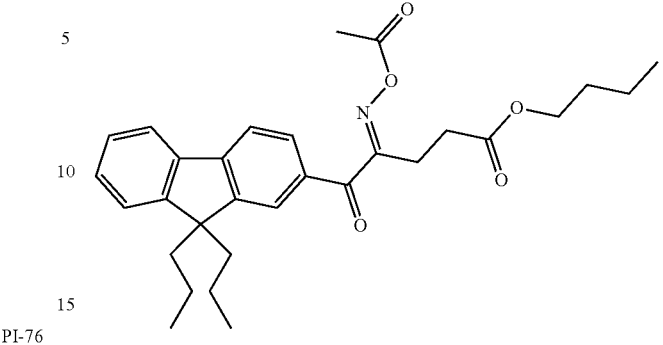
PI-80
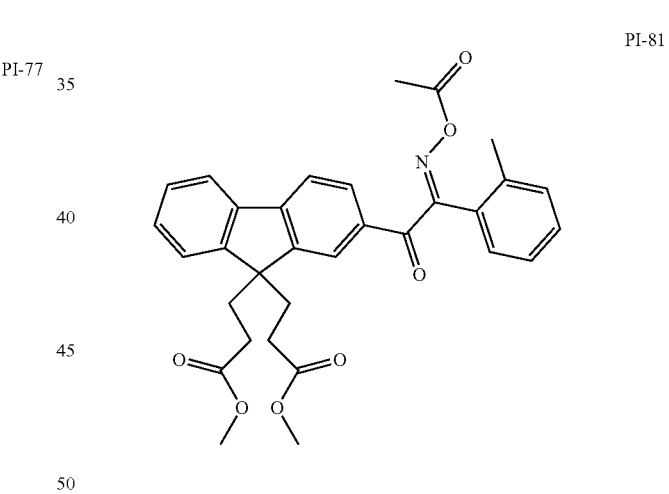
PI-81
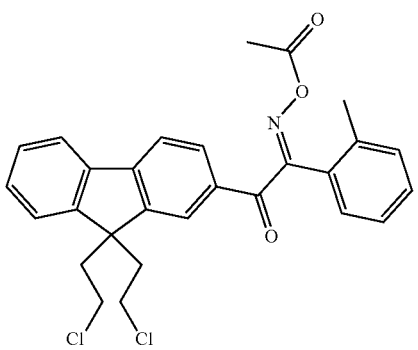
PI-82
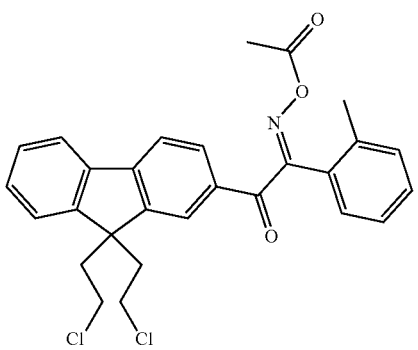

PI-83

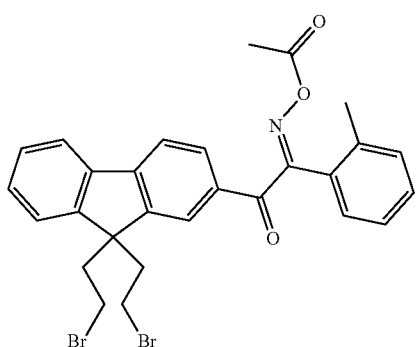

The content of the photopolymerization initiator (B) is preferably 0.5% by mass or more and 30% by mass or less, and more preferably 1% by mass or more and 20% by mass or less, based on the mass of the total solid component of the photosensitive resin composition. It is possible to obtain a photosensitive resin composition in which defective pattern shapes are less likely to occur by adjusting the content of the photopolymerization initiator (B) in the above range.

The photopolymerization initiator (B) may be used in combination with a photoinitiation auxiliary. Examples of the photoinitiation auxiliary include thiol compounds such as triethanolamine, methyldiethanolamine, N-phenyldiethanolamine, triisopropanolamine, methyl 4-dimethylaminobenzoate, ethyl 4-dimethylaminobenzoate, isoamyl 4-dimethylaminobenzoate, 2-ethylhexyl 4-dimethylaminobenzoate, benzoic acid 2-dimethylaminoethyl, N,N-dimethyl p-toluidine, 4,4'-bis(dimethylamino) benzophenone, 9,10-dimethoxyanthracene, 2-ethyl-9,10-dimethoxyanthracene, 9,10-diethoxyanthracene, 2-ethyl-9,10-diethoxyanthracene, 2-mercaptobenzothiazole, 2-mercaptobenzoxazole, 2-mercaptobenzimidazole, 2-mercapto-5-methoxybenzothiazole, 3-mercaptopropionic acid, methyl 3-mercaptopropionate, pentaerythritol tetramercaptoacetate, and 3-mercaptopropionate. These photoinitiation auxiliaries can be used alone, or two or more photoinitiation auxiliaries can be used in combination.

<Photopolymerizable Monomer (C)>

The photosensitive resin composition may include a photopolymerizable monomer (C) for the purpose of improving the photocurability. The photopolymerizable monomer (C) includes a monofunctional monomer and a polyfunctional monomer.

Examples of the monofunctional monomer include (meth)acrylamide, methylol(meth)acrylamide, methoxymethyl(meth)acrylamide, ethoxymethyl(meth)acrylamide, propoxymethyl(meth)acrylamide, butoxymethoxymethyl(meth)acrylamide, N-methylol(meth)acrylamide, N-hydroxymethyl(meth)acrylamide, (meth)acrylic acid, fumaric acid, maleic acid, maleic anhydride, itaconic acid, itaconic anhydride, citraconic acid, citraconic anhydride, crotonic acid, 2-acrylamide-2-methylpropanesulfonic acid, tert-butylacrylamidesulfonic acid, methyl (meth)acrylate, ethyl (meth)acrylate, butyl (meth)acrylate, 2-ethylhexyl (meth)acrylate, cyclohexyl (meth)acrylate, 2-hydroxyethyl (meth)acrylate, 2-hydroxypropyl (meth)acrylate, 2-hydroxybutyl (meth)acrylate, 2-phenoxy-2-hydroxypropyl (meth)acrylate, 2-(meth)acryloyloxy-2-hydroxypropyl phthalate, glycerin mono(meth)acrylate, tetrahydrofurfuryl (meth)acrylate, dimethylaminoethyl (meth)acrylate, glycidyl (meth)acrylate, 2,2,2-trifluoroethyl (meth)acrylate, 2,2,3,3-tetrafluoropropyl (meth)acrylate, a half (meth)acrylate of a phthalic acid derivative, and the like. These monofunctional monomers may be used alone, or two or more monofunctional monomers may be used in combination.

Examples of the polyfunctional monomer include ethylene glycol di(meth)acrylate, diethylene glycol di(meth)acrylate, triethylene glycol di(meth)acrylate, tetraethylene glycol di(meth)acrylate, propylene glycol di(meth)acrylate, polypropylene glycol di(meth)acrylate, butylene glycol di(meth) acrylate, neopentyl glycol di(meth)acrylate, 1,6-hexane glycol di(meth)acrylate, trimethylolpropane tri(meth)acrylate, glycerin di(meth)acrylate, pentaerythritol triacrylate, pentaerythritol tetraacrylate, dipentaerythritol pentaacrylate, dipentaerythritol hexaacrylate, pentaerythritol di(meth)acrylate, pentaerythritol tri(meth)acrylate, pentaerythritol tetra(meth)acrylate, dipentaerythritol penta(meth)acrylate, dipentaerythritol hexa(meth)acrylate, 2,2-bis(4-(meth)acryloxydiethoxyphenyl)propane, 2,2-bis(4-(meth)acryloxypolyethoxyphenyl)propane, 2-hydroxy-3-(meth)acryloyloxypropyl (meth)acrylate, ethylene glycol diglycidyl ether di(meth)acrylate, diethylene glycol diglycidyl ether di(meth)acrylate, phthalic acid diglycidyl ester di(meth)acrylate, glycerin triacrylate, glycerin polyglycidyl ether poly (meth)acrylate, urethane (meth)acrylate (i.e., tolylene diisocyanate), a reaction product of trimethylhexamethylene diisocyanate, hexamethylene diisocyanate, and 2-hydroxyethyl (meth)acrylate, methylenebis(meth)acrylamide, (meth)acrylamide methylene ether, a polyfunctional monomer such as a fused product of polyvalent alcohol and N-methylol(meth) acrylamide, triacryl formal, and the like. These polyfunctional monomers may be used alone, or two or more polyfunctional monomers may be used in combination.

The content of the photopolymerizable monomer (C) in the photosensitive resin composition is preferably 3% by mass or more and 50% by mass or less, and more preferably 5% by mass or more and 40% by mass or less, based on the mass of the total solid component of the photosensitive resin composition. It is possible to obtain a photosensitive resin composition in which defective pattern shapes are less likely to occur by adjusting the content of the photopolymerizable monomer (C) in the above range. A cured film with particularly excellent adhesion to substrates is easily formed by adjusting the content of the photopolymerizable monomer (C) in the above range.

<Coloring Agent (D)>

The photosensitive resin composition may include a coloring agent (D). The coloring agent (D) is not particularly limited, but it is preferable to use, for example, compounds which are classified into Pigment in Color Index (C.I.; published by The Society of Dyers and Colorist), and specifically those having the following color index (C.I.) numbers.

Suitable examples of the yellow pigment, which can be suitably used, include C.I. pigment yellow 1 (hereinafter, "C.I. pigment yellow" is the same, and only the numbers are listed), 3, 11, 12, 13, 14, 15, 16, 17, 20, 24, 31, 53, 55, 60, 61, 65, 71, 73, 74, 81, 83, 86, 93, 95, 97, 98, 99, 100, 101, 104, 106, 108, 109, 110, 113, 114, 116, 117, 119, 120, 125, 126, 127, 128, 129, 137, 138, 139, 147, 148, 150, 151, 152, 153, 154, 155, 156, 166, 167, 168, 175, 180, and 185.

Examples of the orange pigment, which can be suitably used, include C.I. pigment orange 1 (hereinafter, "C.I. pigment orange" is the same, and only the numbers are listed), 5, 13, 14, 16, 17, 24, 34, 36, 38, 40, 43, 46, 49, 51, 55, 59, 61, 63, 64, 71, and 73.

Examples of the violet pigment, which can be suitably used, include C.I. pigment violet 1 (hereinafter, "C.I. pigment violet" is the same, and only the numbers are listed), 19, 23, 29, 30, 32, 36, 37, 38, 39, 40, and 50.

Examples of the red pigment, which can be suitably used, include C.I. pigment red 1 (hereinafter, "C.I. pigment red" is the same, and only the numbers are listed), 2, 3, 4, 5, 6, 7, 8, 9, 10, 11, 12, 14, 15, 16, 17, 18, 19, 21, 22, 23, 30, 31, 32, 37, 38, 40, 41, 42, 48:1, 48:2, 48:3, 48:4, 49:1, 49:2, 50:1, 52:1, 53:1, 57, 57:1, 57:2, 58:2, 58:4, 60:1, 63:1, 63:2, 64:1, 81:1, 83, 88, 90:1, 97, 101, 102, 104, 105, 106, 108, 112, 113, 114, 122, 123, 144, 146, 149, 150, 151, 155, 166, 168, 170, 171, 172, 174, 175, 176, 177, 178, 179, 180, 185, 187, 188, 190, 192, 193, 194, 202, 206, 207, 208, 209, 215, 216, 217, 220, 223, 224, 226, 227, 228, 240, 242, 243, 245, 254, 255, 264, and 265.

Examples of the blue pigment, which can be suitably used, include C.I. pigment blue 1 (hereinafter, "C.I. pigment blue" is the same, and only the numbers are listed), 2, 15, 15:3, 15:4, 15:6, 16, 22, 60, 64, and 66.

Examples of the pigment with the other hue, which can be suitably used, include green pigments such as C.I. pigment green 7, C.I. pigment green 36, and C.I. pigment green 37; brown pigments such as C.I. pigment brown 23, C.I. pigment brown 25, C.I. pigment brown 26, and C.I. pigment brown 28; and black pigments such as C.I. pigment black 1 and C.I. pigment black 7.

The photosensitive resin composition may contain, as the coloring agent (D), a light shielding agent. The photosensitive resin composition containing a light shielding agent is suitably used to form a black matrix or a black column spacer in a liquid crystal display panel, and to form a bank for demarcation of a luminous layer in an organic EL element.

In the case where the light shielding agent is used as the coloring agent (D), it is preferable to use a black pigment or a purple pigment as the light shielding agent. Examples of the black pigment and the purple pigment include various types of pigments irrespective of whether it is an organic substance or an inorganic substance, such as carbon black, titanium black, and a metal oxide, a composite oxide, a metal sulfide, a metal sulfate, and a metal carbonate of copper, iron, manganese, cobalt, chromium, nickel, zinc, calcium, silver, or the like.

As the carbon black, known carbon black such as channel black, furnace black, thermal black, and lamp black are usable. Also, a resin-coated carbon black may be used.

As the carbon black, a carbon black having been processed to introduce an acidic group is preferable. The acidic group to be introduced to the carbon black is a functional group which is acidic according to the definition by Bronsted. Specific examples of the acidic group include a carboxyl group, a sulfonic group, and a phosphonic group. The acidic group introduced to the carbon black may form a salt. Cation forming the salt with the acidic group and the salt is not particularly limited as long as it does not interfere with the objective of the present invention. As an example of the cation, various metal ions, cations of a nitrogen-containing compound, ammonium ions and the like can be exemplified, and alkali metal ions such as sodium ions, potassium ions, and lithium ions as well as ammonium ions are preferable.

Among the above described carbon black having been processed to introduce an acidic group, carbon black having at least one functional group selected from a group consisting of a carboxylic acid group, a carboxylic acid salt group, a sulfonic group, and a sulfonic acid salt group is preferable, in view of achieving higher insulation properties of a light shielding cured film formed by using the photosensitive resin composition.

A method of introducing an acidic group to the carbon black is not particularly limited. As a method of introducing an acidic group, for example, the following methods may be exemplified:

1) A method of introducing a sulfonic group to the carbon black by means of direct substitution using strong sulfuric acid such as fuming sulfuric acid and chlorosulfonic acid, or indirect substitution using sulfite, hydrogen sulfite and the like;
2) A method of diazo-coupling an organic compound having an amino group and an acidic group with the carbon black;
3) A method of reacting an organic compound having a halogen atom and an acidic group with the carbon black having a hydroxyl group, by the Williamson etherification method;
4) A method of reacting an organic compound having a halo carbonyl group and an acidic group protected by a protecting group with the carbon black having a hydroxyl group; and
5) A method of performing Friedel-Crafts reaction on the carbon black using an organic compound having a halo carbonyl group and an acidic group protected by a protecting group and then deprotecting.

Among these methods, the method 2), allowing easy and safe introduction of an acidic group, is preferable. As the organic compound having an amino group and an acidic group used in the method 2), a compound in which an amino group and an acidic group are bound to an aromatic group is preferable. As such a compound, aminobenzenesulfonic acid such as sulfanilic acid and aminobenzoic acid such as 4-aminobenzoic acid can be exemplified.

A molar number of the acidic group to be introduced to the carbon black is not particularly limited as long as it does not interfere with the objective of the present invention. A molar number of the acidic group to be introduced to the carbon black is preferably 1 mmol or more and 200 mmol or less and more preferably 5 mmol or more and 100 mmol or less with respect to 100 g of carbon black.

Carbon black having an acidic group introduced thereinto may be subjected to a coating treatment with a resin. When using a photosensitive resin composition containing carbon black coated with a resin, it is easy to form a light shielding cured film with excellent light shielding property and insulation properties, and low surface reflectivity. The coating treatment with a resin does not exert an adverse influence particularly on a dielectric constant of a light shielding cured film formed by using the photosensitive resin composition. Examples of the resin, which can be used for coating of carbon black, include thermosetting resins such as a phenol resin, a melamine resin, a xylene resin, a diallyl phthalate resin, a glyptal resin, an epoxy resin, and an alkylbenzene resin, and thermoplastic resins such as polystyrene, polycarbonate, polyethylene terephthalate, polybutylene terephthalate, modified polyphenylene oxide, polysulfone, polyparaphenyleneterephthalamide, polyamideimide, polyimide, polyaminobismaleimide, polyether sulfopolyphenylene sulfone, polyarylate, and polyether ether ketone. The amount of the resin, with which carbon black is coated, is preferably 1% by mass or more and 30% by mass or less, based on the total mass of the carbon black and resin.

The light shielding agent is also preferably a perylene-based pigment. Specific examples of the perylene-based pigment include a perylene-based pigment represented by the following formula (d-1), a perylene-based pigment represented by the following formula (d-2), and a perylene-based pigment represented by the following formula (d-3).

It is possible to preferably use, as the perylene-based pigment, commercially available products, for example, K0084 and K0086, and Pigment Black 21, 30, 31, 32, 33, and 34 (product name) manufactured by BASF Ltd.

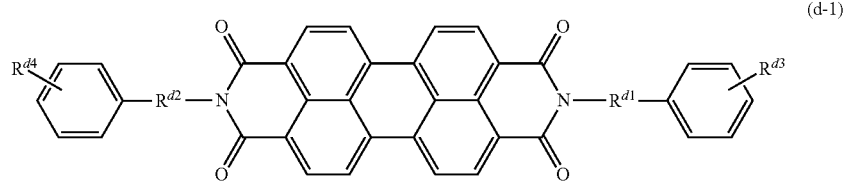

(d-1)

In the formula (d-1), $R^{d1}$ and $R^{d2}$ each independently represent an alkylene group having 1 or more and 3 or less carbon atoms, $R^{d3}$ and $R^{d4}$ each independently represent a hydrogen atom, a hydroxyl group, a methoxy group, or an acetyl group.

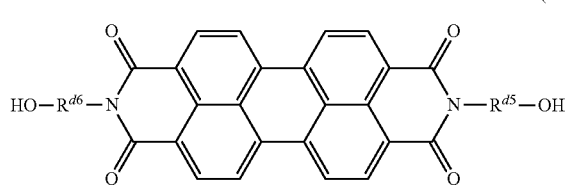

(d-2)

In the formula (d-2), $R^{d5}$ and $R^{d6}$ each independently represent an alkylene group having 1 or more and 7 or less carbon atoms.

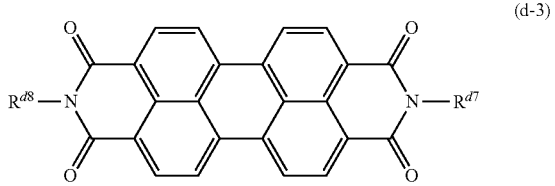

(d-3)

In the formula (d-3), $R^{d7}$ and $R^{d8}$ each independently represent a hydrogen atom, an alkyl group having 1 or more and 22 or less carbon atoms, and may contain a heteroatom of N, O, S, or P. When $R^{d7}$ and $R^{d8}$ are alkyl groups, the alkyl group may be either a straight-chain or branched-chain alkyl group.

The compound represented by the formula (d-1), the compound represented by the formula (d-2), the compound represented by the formula (d-3) can be synthesized by using the method mentioned, for example, in Japanese Unexamined Patent Application Publication No. 62-1753 and Japanese Examined Patent Application Publication No. 63-26784. Using perylene-3,5,9,10-tetracarboxylic acid or a dianhydride thereof and amines as raw materials, a heating reaction is performed in water or an organic solvent. The thus obtained crude product is reprecipitated in sulfuric acid, or recrystallized in water, an organic solvent, or a mixed solvent thereof, thus making it possible to obtain an objective substance.

To satisfactorily disperse a perylene-based pigment in the photosensitive resin composition, an average particle diameter of the perylene-based pigment is preferably 10 nm or more and 1,000 nm or less.

It is also possible to contain, as the light shielding agent, a lactam-based pigment. The lactam-based pigment includes, for example, a compound represented by the following formula (d-4):

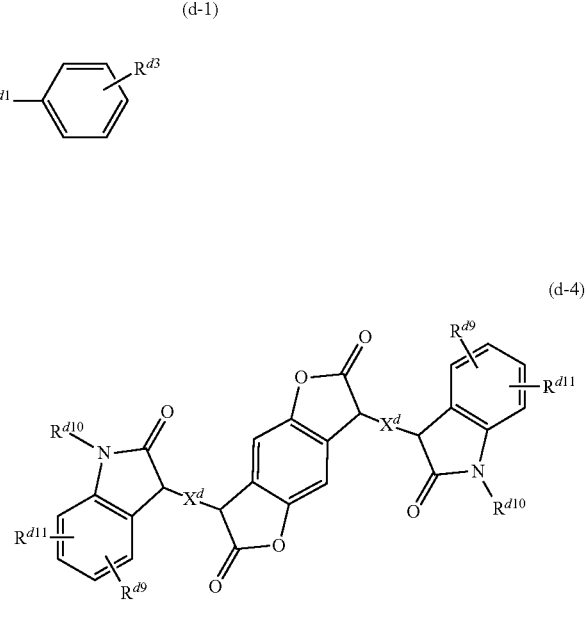

(d-4)

wherein, in the formula (d-4), $X^d$ represents a double bond, E form or Z form each independently exists as a geometrical isomer, $R^{d9}$(s) each independently represent a hydrogen atom, a methyl group, a nitro group, a methoxy group, a bromine atom, a chlorine atom, a fluorine atom, a carboxy group, or a sulfo group, $R^{d10}$(s) each independently represent a hydrogen atom, a methyl group, or a phenyl group, and $R^{d11}$(s) each independently represent a hydrogen atom, a methyl group, or a chlorine atom. Compounds represented by the formula (d-4) can be used alone, or two or more compounds can be used in combination. $R^{d9}$ is preferably bonded at the 6-position of a dihydroindolone ring in view of easily producing a compound represented by the formula (d-4), and $R^{d11}$ is preferably bonded at the 4-position of a dihydroindolone ring. From the same viewpoint, $R^{d9}$, $R^{d10}$, and $R^{d11}$ are preferably hydrogen atoms. The compound represented by the formula (d-4) includes, as geometrical isomers, EE form, ZZ form, and EZ form, and may be either a single compound of any one of them, or a mixture of these geometrical isomers. The compound represented by the formula (d-4) can be produced, for example, by the methods mentioned in WO 2000/24736 A, WO 2010/081624 A.

To satisfactorily disperse a lactam-based pigment in the composition, an average particle diameter of the lactam-based pigment is preferably 10 nm or more and 1,000 nm or less.

Fine particles containing a silver-tin (AgSn) alloy as a main component (hereinafter referred to as "AgSn alloy fine particles") are also preferably used as a light shielding agent. The AgSn alloy fine particles only need to contain an AgSn alloy as a main component, and also may contain Ni, Pd, Au, and the like as a metal component. An average particle diameter of the AgSn alloy fine particles is preferably 1 nm or more and 300 nm or less.

When the AgSn alloy is represented by the chemical formula AgxSn, a chemically stable AgSn alloy is obtained if x satisfies the inequality expression: $1 \leq x \leq 10$, and the chemical stability and blackness are simultaneously obtained if x satisfies the inequality expression: $3 \leq x \leq 4$. When a mass ratio of Ag in an AgSn alloy is determined in the above range of x, the following relations:

when x=1, Ag/AgSn=0.4762
when x=3, 3.Ag/Ag3Sn=0.7317
when x=4, 4.Ag/Ag4Sn=0.7843
when x=10, 10.Ag/Ag10Sn=0.9008 are obtained. Therefore, this AgSn alloy becomes chemically stable when containing 47.6% by mass or more and 90% by mass or less of Ag, and it is possible to obtain the chemical stability and blackness effectively to the amount of Ag when containing 73.17% by mass or more and 78.43% by mass or less of Ag.

The AgSn alloy fine particles can be fabricated by using a usual fine particle synthesis method. Examples of fine particle synthesis method include a gas phase reaction method, an atomized pyrolysis method, an atomizing method, a liquid phase reaction method, a freeze-drying method, a hydrothermal method, and the like.

Although AgSn alloy fine particles have high insulation properties, a surface thereof may be covered with an insulation film depending on applications of the photosensitive resin composition to further enhance insulation properties. The material of the insulation film is suitably metal oxide or an organic polymer compound. It is possible to suitably use, as the metal oxide, metal oxides with insulation properties, for example, silicon oxide (silica), aluminum oxide (alumina), zirconium oxide (zirconia), yttrium oxide (yttria), titanium oxide (titania), and the like. It is also possible to suitably use, as the organic polymer compound, resins with insulation properties, for example, polyimide, polyether, poly acrylate, polyamine compound, and the like.

To sufficiently enhance insulation properties of a surface of AgSn alloy fine particles, a thickness of the insulation film is preferably 1 nm or more and 100 nm or less, and more preferably 5 nm or more and 50 nm or less. The insulation film can be easily formed by surface modification technique or surface coating technique. Particularly, when using an alkoxide such as tetraethoxysilane or aluminum triethoxide, an insulation film with a uniform thickness can be formed at comparatively low temperature, preferably.

The above-mentioned perylene-based pigment, lactam-based pigment, and AgSn alloy fine particles may be used alone as the light shielding agent, or these materials may be used in combination. For the purpose of adjusting color tone, the light shielding agent may contain colors with red, blue, green, and yellow hues, together with black pigmnets or violet pigments mentioned above. It is possible to appropriately select colors with other hues of black pigments and violet pigments from known colors. It is possible to use, as colors with other hues of black pigmnets and violet pigments, various pigments mentioned above. The amount of colors with other hues of black pigments and violet pigments to be used is preferably 15% by mass or less, and more preferably 10% by mass or less, based on the total mass of the light shielding agent.

Further, a dispersant may be used for uniformly dispersing the coloring agent in the composition. As the dispersant, polyethylene imine-based, urethane resin-based, or acryl resin-based polymer dispersants is preferably used. Particularly, in the case where the carbon black is used as the coloring agent, it is preferable to use the acryl resin-based dispersant as the dispersant. Due to the decomposition of the dispersant, a corrosive gas may be generated from the cured film of the photosensitive resin composition. Therefore, the coloring agent is preferably subjected to a dispersion treatment without using the dispersant.

Inorganic and organic pigments may be used alone, or two or more pigments may be used in combination. When using these pigments in combination, the organic pigment is preferably used in the amount in a range of 10 parts by mass or more and 80 parts by mass or less, and more preferably 20 parts by mass or more and 40 parts by mass or less, based on 100 parts by mass of the total amount of inorganic and organic pigments.

The photosensitive resin composition can also use a dye as the coloring agent (D), in addition to the pigment. This dye only needs to be appropriately selected from known materials. Examples of the dye applicable to the photosensitive resin composition of the present embodiment include an azo dye, a metal complex salt azo dye, an anthraquinone dye, a triphenylmethane dye, a xanthene dye, a cyanine dye, a naphthoquinone dye, a quinoneimine dye, a methine dye, a phthalocyanine dye, and the like. These dyes can also be used as the coloring agent (D) after dispersing in an organic solvent by laking (salification). It is also possible to preferably use, in addition to these dyes, dyes mentioned in Japanese Unexamined Patent Application Publication No. 2013-225132, Japanese Unexamined Patent Application Publication No. 2014-178477, Japanese Unexamined Patent Application Publication No. 2013-137543, Japanese Unexamined Patent Application Publication No. 2011-38085, Japanese Unexamined Patent Application Publication No. 2014-197206, and the like. These dyes can also be used in combination with pigments mentioned above (e.g., perylene-based pigment, lactam-based pigment, AgSn alloy fine particles, etc.).

The amount of the coloring agent (D) to be used in photosensitive resin composition can be appropriately selected as long as it does not interfere with the object of the present invention. Typically, the amount is preferably 5% by mass or more and 70% by mass or less, and more preferably 25% by mass or more and 60% by mass or less, based on the mass of the total solid component of the photosensitive resin composition.

The coloring agent (D) is preferably added to the photosensitive resin composition after being converted into a dispersion by dispersing in a proper concentration in the presence or absence of a dispersant. As used herein, it is possible to define the amount of the above-mentioned coloring agent (D) to be used, as the value containing this existing dispersant.

<Organic Solvent (S)>

The photosensitive resin composition usually contains an organic solvent (S) for the purpose of adjusting the coatability. The organic solvent (S) is not particularly limited as long as it can dissolve components such as a resin (A), a photopolymerization initiator (B), and a photopolymerizable monomer (C).

Examples of the organic solvent (S) include nitrogen-containing polar solvents such as N-methyl-2-pyrrolidone (NMP), N,N-dimethylacetamide (DMAc), N,N-dimethylisobutylamide, N,N-diethylacetamide, N,N-dimethylformamide (DMF), N,N-diethylformamide, N-methylcaprolactam, 1,3-dimethyl-2-imidazolidinone (DMI), pyridine, and N,N,N',N'-tetramethylurea (TMU); lactone-based polar solvents such as β-propiolactone, γ-butyrolactone, γ-valerolactone, δ-valerolactone, γ-caprolactone, and ε-caprolactone; dimethyl sulfoxide; hexamethylphosphoric tripamides; acetonitrile; fatty acid esters such as ethyl lactate, butyl lactate and methyl acetate, and ethyl acetate; ethers such as diethylene glycol dimethyl ether, diethylene glycol diethyl ether, dioxane, tetrahydrofuran, methyl cellosolve acetate, and ethyl cellosolve acetate, glyme; and aromatic solvents such as benzene, toluene, and xylene. Among these organic solvents, from the viewpoint of the solubility of the resin (A) and the like, nitrogen-containing polar organic solvents such as N-methyl-2-pyrrolidone, N,N-dimethylacetamide, N,N-diethylacetamide, N,N-dimethylformamide, N,N-diethylformamide, N,N-dimethylisobutylamide, N-methylcaprolactam, and N,N,N',N'-tetramethylurea, or fatty acid esters such as ethyl lactate and butyl lactate are preferable. It is also possible to use these organic solvents in combination.

The amount of the organic solvent (S) to be used is not particularly limited as long as long as it does not interfere with the object of the present invention. Typically, the organic solvent (S) is used so that the solid component concentration of the photosensitive resin composition is 3% by mass or more and 50% by mass or less, preferably 5% by mass or more and 40% by mass or less, and more preferably 10% by mass or more and 35% by mass or less.

<Other Components>

The photosensitive resin composition can optionally contain additives such as a surfactant, an anticorrosive, a heat crosslinking agent, an adhesion improver, a thermal polymerization inhibitor, a defoamer, and a silane coupling agent. It is possible to use, as any additives, conventionally known additives. The photosensitive resin composition may contain a silane coupling agent since a cured film with excellent adhesion to substrates is formed particularly easily. It is possible to use, as the silane coupling agent, conventionally known one without particular limitation. Examples of the surfactant include anionic, cationic, and nonionic compounds, examples of the thermal polymerization inhibitor include hydroquinone and hydroquinone monoethyl ether, and examples of the defoamer include silicone-based and fluorine-based compounds. It is possible to use the anticorrosive by appropriately selecting from conventionally known various anticorrosives depending on type of a substance which is prevented from corrosion.

The heat crosslinking agent is a compound which allows the resin (A) to further crosslink by heating, or which itself undergoes crosslinking. The photosensitive resin composition contains a heat crosslinking agent, whereby, a cured film with particularly excellent heat resistance and chemical resistance can be formed. It is possible to preferably used, as the heat crosslinking agent, an amino resin and derivatives thereof. Among these, a urea resin, a glycol-urea resin, a hydroxyethylene-urea resin, a melamine resin, benzoguanamine resin, and derivatives thereof are suitably used. An alkoxymethylated urea compound and an alkoxymethylated melamine compound are particularly preferably used. The amount of the heat crosslinking agent to be used is preferably 0.1% by mass or more and 30% by mass or less, more preferably 0.5% by mass or more and 20% by mass or less, and particularly preferably 2% by mass or more and 10% by mass or less, based on the mass of the resin (A).

<Method for Preparing Photosensitive Resin Composition>

The above-described photosensitive resin composition is obtained by mixing the above respective components in each predetermined amount, and uniformly mixing using a stirrer. The mixture may be filtered through a filter so that the thus obtained mixture becomes more uniform.

<<Method for Producing Cured Film>>

Hereinafter, a description will be made of a method for producing a cured film according to the sixth aspect of the present invention, and a cured film according to the seventh aspect. The method for producing a cured film according to the sixth aspect is a method using the photosensitive resin composition according to the first aspect. The cured film according to the seventh aspect is a cured film which is obtained by curing the photosensitive resin composition according to the first aspect.

It is possible to appropriately select, as the method for producing a cured film, from conventionally known methods for producing a cured film, as far as it is possible to satisfactorily polymerize molecules of a polyamide resin contained in a resin (A), or to polymerize the molecule of a polyamide resin contained in a resin (A) with a photopolymerizable monomer (C).

Suitable method for producing a cured film includes a method including:
applying the photosensitive resin composition mentioned above to form a coating film, and
exposing the coating film.

To form a cured film by using a photosensitive resin composition, first, the photosensitive resin composition is applied on a substrate selected depending on applications of the cured film to form a coating film. The method for forming a coating film is not particularly limited and performed using, for example, a contact transfer type applicator such as a roll coater, a reverse coater, or a bar coater, or a non-contact type applicator such as a spinner (rotary applicator) or a curtain flow coater.

The thus applied photosensitive resin composition is optionally dried to form a coating film. The drying method is not particularly limited and includes, for example, (1) a method of drying at a temperature of 80° C. or higher and 120° C. or lower, and preferably at 90° C. or higher and 100° C. or lower, for 60 seconds or more and 120 seconds or less using a hot plate, (2) a method of standing at room temperature for several hours or more and several days or less, and (3) a method of placing in a warm air heater or an infrared heater for several tens of minutes to several hours to remove an organic solvent.

Then, exposure to a coating film is performed. Exposure is performed by irradiation with active energy rays such as ultraviolet rays and excimer laser light. Exposure is regioselectively performed, for example, by a method of exposing through a negative mask. The energy dose irradiated varies depending on the composition of the photosensitive resin composition and is preferably, for example, about 40 mJ/cm$^2$ or more and 200 mJ/cm$^2$ or less. When the entire surface of the coating film is exposed, a non-patterned cured film having a shape corresponding to a shape of the coating film is formed.

When the coating film is regioselectively exposed, the exposed film is developed with a developing solution, whereby, the unexposed area is removed by dissolving in the developing solution, thus forming a patterned cured film. The development method is not particularly limited and, for example, a dipping method, a spraying method, and the like can be used. The developing solution is appropriately selected depending on the composition of the photosensitive resin composition. An organic solvent and an alkali developing solution are preferably used as the developing solution.

The organic solvent to be used as the developing solution is not particularly limited as long as it does not dissolve the exposed area and dissolves the unexposed area. Examples of the organic solvent, which is preferable as the developing solution, include N-methyl-2-pyrrolidone, N-cyclohexyl-2-pyrrolidone, N,N-dimethylacetamide, N,N-diethylacetamide, N,N-dimethylformamide, N,N-diethylformamide, N,N-dimethylisobutylamide, cyclopentanone, cyclohexanone, γ-butyrolactone, α-acetyl-γ-butyrolactone, N-methylcaprolactam, and N,N,N',N'-tetramethylurea. Two or more organic solvents can be used in combination.

The developing solution is preferably a mixed solvent of the above-mentioned preferable organic solvent and a poor solvent, which is less likely to dissolve a photosensitive resin composition. It is possible to adjust the solubility of the exposed area and the unexposed area in the developing solution by adjusting the type and amount of the poor solvent.

Examples of the poor solvent include toluene, xylene, methanol, ethanol, isopropyl alcohol, ethyl lactate, propylene glycol monomethyl ether acetate, and water. Two or more poor solvents can be used in combination.

As an alkaline developing solution, an aqueous solution containing one or more alkali compounds selected from inorganic alkali compounds and organic alkali compounds can be used. The concentration of an alkali compound in a developing solution is not particularly limited, as long as the developing solution can satisfactorily develop a coating film or a formed article after the exposure. Typically, the concentration of an alkali compound in a developing solution is preferably 1% by mass or higher and 10% by mass or lower.

Examples of the inorganic alkali compounds include lithium hydroxide, sodium hydroxide, potassium hydroxide, diammonium hydrogen phosphate, dipotassium hydrogen phosphate, disodium hydrogen phosphate, lithium silicate, sodium silicate, potassium silicate, lithium carbonate, sodium carbonate, potassium carbonate, lithium borate, sodium borate, potassium borate, ammonia, and the like. Examples of the organic alkali compounds include tetramethylammonium hydroxide, tetraethylammonium hydroxide, trimethylhydroxyethylammonium hydroxide, methylamine, dimethylamine, trimethylamine, monoethylamine, diethylamine, triethylamine, n-propylamine, di-n-propylamine, isopropylamine, diisopropylamine, methyldiethylamine, dimethylethanolamine, ethanolamine, triethanolamine, and the like.

Further, in the developing solution, appropriate amounts of water-soluble organic solvents such as methanol, ethanol, propanol or ethylene glycol, a surfactant, a preservation stabilizer and a resin-dissolution suppressing agent can be added, as needed.

The developed cured film is optionally rinsed with water and then dried, thus obtaining a cured film. The cured film thus obtained by using the photosensitive resin composition satisfactorily adheres to a substrate, and is therefore suitably used in various applications. Particularly, when the photosensitive resin composition contains no coloring agent, a cured film with excellent transparency is formed by using the photosensitive resin composition. The transparency of the cured film is not particularly limited. Regarding the cured film formed under the following conditions, a transmittance of light in the entire wavelength region of 380 nm or more and 780 nm or less is 80% or more, and more preferably 90% or more.

<Curing Conditions>

A photosensitive resin composition is applied on a glass substrate to obtain a coating film having a thickness of 10 μm. Then, the thus formed coating film is exposed at light exposure of 100 mJ/cm². After exposure, baking is performed under nitrogen atmosphere at 300° C. for 2 hours to form a cured film.

<<Polyamide Resin>>

Hereinafter, a description will be made of a polyamide resin according to the second aspect of the present invention. The polyamide resin according to the second aspect is directed to a polyamide resin comprising a structural unit represented by the following formula (a1):

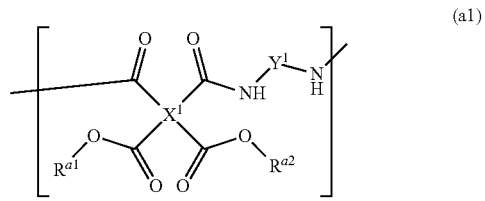

wherein, in the formula (a1), $X^1$ is a tetravalent group represented by the following formula (a2):

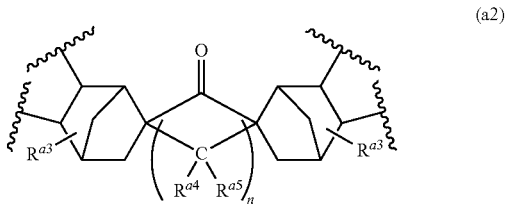

$Y^1$ is a divalent organic group,
$R^{a1}$ and $R^{a2}$ each independently represent a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

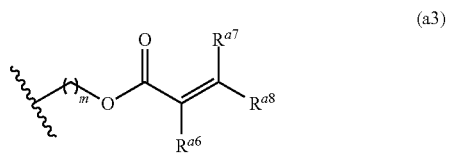

at least one of $R^{a1}$ and $R^{a2}$ is a group represented by the formula (a3),
in the above formula (a2), $R^{a3}$, $R^{a4}$, and $R^{a5}$ each independently represent one selected from the group consisting of a hydrogen atom, an alkyl group having 1 or more and 10 or less carbon atoms, and a fluorine atom,
n is an integer of 0 or more and 12 or less,
in the above formula (a3), $R^{a6}$, $R^{a7}$, and $R^{a8}$ each independently represent a hydrogen atom or an organic group having 1 or more and 3 or less carbon atoms,
m is an integer of 2 or more and 10 or less, and
when at least one of the $R^{a1}$ and the $R^{a2}$ is a hydrogen atom, a carboxy group represented by —COOR$^{a1}$ or —COOR$^{a2}$ may form an acid halide or may form a salt.

The polyamide resin according to the second aspect is the same as the polyamide resin mentioned as the component of the photosensitive resin composition, except that, when at least one of $R^{a1}$ and $R^{a2}$ in the formula (a1) is a hydrogen atom, a carboxy group represented by —COOR$^{a1}$ or —COOR$^{a2}$ may form an acid halide, or may form a salt. The acid halide is preferably acid chloride and acid bromide, and more preferably acid chloride. Cations forming a carboxylate may be either inorganic cations or organic cations. Examples of the carboxylate include metal salts of alkali metals such as lithium, sodium, and potassium, and salts of Group 2 metals such as magnesium, calcium, and strontium, and salts with organic bases such has ammonia, triethylamine, and pyridine.

A method of converting a carboxy group into an acid halide is not particularly limited, and conversion is performed in accordance with an ordinary method. For example, acid chloride is produced by reacting the carboxy group with a reagent such as thionyl chloride, oxalyl chloride, phosphoryl chloride, sulfuryl chloride, phosphorus trichloride, phosphorus pentachloride, and phosphorus oxychloride.

<<Method for Producing Polyamide Resin>>

Hereinafter, a description will be made of a method for producing a polyamide resin according to the third aspect of the present invention. The third aspect of the present invention is directed to a method for producing the polyamide resin according to the second aspect, the method including condensing a polyvalent carboxylic acid compound represented by the following formula (I):

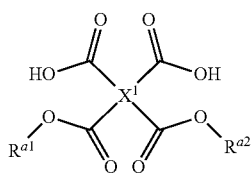

(I)

wherein, in the formula (I), $X^1$ is a tetravalent group represented by the following formula (a2):

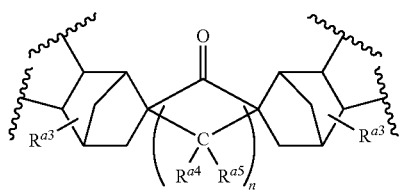

(a2)

$R^{a1}$ and $R^{a2}$ each independently represent a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

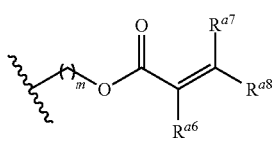

(a3)

at least one of $R^{a1}$ and $R^{a2}$ is a group represented by the formula (a3),
in the formula (a2), $R^{a3}$, $R^{a4}$, and $R^{a5}$ each independently represent one selected from the group consisting of a hydrogen atom, an alkyl group having 1 or more and 10 or less carbon atoms, and a fluorine atom,
n is an integer of 0 or more and 12 or less, in the formula (a3), $R^{a6}$, $R^{a7}$, and $R^{a8}$ each independently represent a hydrogen atom or an organic group having 1 or more and 3 or less carbon atoms,
m is an integer of 2 or more and 10 or less, and/or
an acid halide of the polyvalent carboxylic acid compound, and a diamine compound represented by the following formula (II):

$$H_2N-Y^1-NH_2 \qquad (II)$$

wherein, in the formula (II), $Y^1$ is a divalent organic group.

The method for producing a polyamide resin according to the third aspect is the same as the preferred method for producing a polyamide resin mentioned above as the component of the photosensitive resin composition, except that, when at least one of $R^{a1}$ and $R^{a2}$ in the formula (a1) is a hydrogen atom in the polyamide resin to be produced according to the second aspect, a carboxy group represented by $-COOR^{a1}$ or $-COOR^{a2}$ may form an acid halide, or may form a salt. The acid halide and the carbonate are as described about the polyamide resin according to the second aspect.

<<Compound and Method for Producing Compound>>

Hereinafter, a description will be made of the compound according to the fourth aspect of the present invention, and a method for producing the compound according to the fifth aspect of the present invention, which is a suitable method for producing the compound according to the fourth aspect.

The compound according to the fourth aspect is, for example, suitably used to produce a polyamide resin including a structural unit represented by the formula (a1), which is an essential component in the photosensitive resin composition according to the first aspect. The compound according to the fourth aspect is directed to a compound represented by the following formula (I):

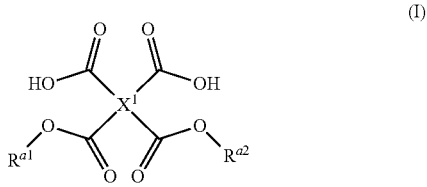

(I)

wherein, in the formula (I), $X^1$ is a tetravalent group represented by the following formula (a2):

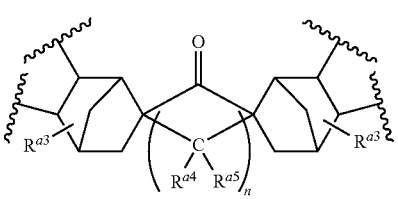

(a2)

$R^{a1}$ and $R^{a2}$ each independently represent a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

(a3)

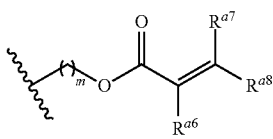

at least one of $R^{a1}$ and $R^{a2}$ is a group represented by the formula (a3), in the formula (a2), $R^{a3}$, $R^{a4}$, and $R^{a5}$ each independently represent one selected from the group consisting of a hydrogen atom, an alkyl group having 1 or more and 10 or less carbon atoms, and a fluorine atom, n is an integer of 0 or more and 12 or less, in the formula (a3), $R^{a6}$, $R^{a7}$, and $R^{a8}$ each independently represent a hydrogen atom or an organic group having 1 or more and 3 or less carbon atoms, m is an integer of 2 or more and 10 or less, and a carboxy group contained in the compound may form an acid halide, or may form a salt.

As mentioned above, when a compound represented by the formula (I) has a carboxy group, a carboxy group may form an acid halide, or may form a salt. The acid halide is preferably acid chloride and acid bromide, and more preferably acid chloride. Cations forming a carboxylate may be either inorganic cations or organic cations. Examples of the carboxylate include metal salts of alkali metals such as lithium, sodium, and potassium, and salts of Group 2 metals such as magnesium, calcium, and strontium, and salts with organic bases such has ammonia, triethylamine, and pyridine.

A method of converting a carboxy group into an acid halide is not particularly limited, and conversion is performed in accordance with an ordinary method. For example, acid chloride is produced by reacting the carboxy group with a reagent such as thionyl chloride, oxalyl chloride, phosphoryl chloride, sulfuryl chloride, phosphorus trichloride, phosphorus pentachloride, and phosphorus oxychloride.

There is no limitation on the method for producing a compound according to the fourth aspect Preferable method includes a method for producing a compound according to the fifth aspect of the present invention, which will be described below.

The method for producing a compound according to the fifth aspect of the present invention is directed to a method for producing the compound, the method including reacting a tetracarboxylic dianhydride represented by the following formula (a4):

(a4)

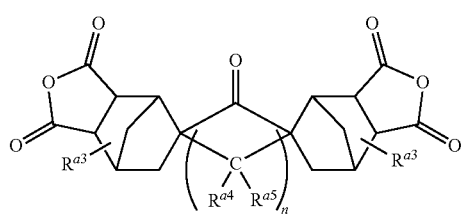

wherein, in the formula (a4), $R^{a3}$, $R^{a4}$, and $R^{a5}$ each independently represent one selected from the group consisting of a hydrogen atom, an alkyl group having 1 or more and 10 or less carbon atoms, and a fluorine atom, n is an integer of 0 or more and 12 or less, with an unsaturated carboxylic acid ester represented by the following formula (a5):

(a5)

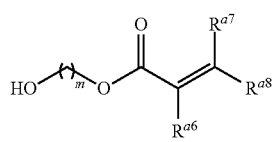

wherein, in the formula (a5), $R^{a6}$, $R^{a7}$, and $R^{a8}$ each independently represent a hydrogen atom or an organic group having 1 or more and 3 or less carbon atoms, and m is an integer of 2 or more and 10 or less.

Examples of the tetracarboxylic dianhydride represented by the formula (a4) include norbornane-2-spiro-α-cyclopentanone-α'-spiro-2"-norbornane-5,5",6,6"-tetracarboxylic dianhydride (another name "norbornane-2-spiro-2'-cyclopentanone-5'-spiro-2"-norbornane-5,5",6,6"-tetracarboxylic dianhydride"), methylnorbornane-2-spiro-α-cyclopentanone-α'-spiro-2"-(methylnorbornane)-5,5",6,6"-tetracarboxylic dianhydride, norbornane-2-spiro-α-cyclohexanone-α'-spiro-2"-norbornane-5,5",6,6"-tetracarboxylic dianhydride (another name "norbornane-2-spiro-2'-cyclohexanone-6'-spiro-2"-norbornane-5,5",6,6"-tetracarboxylic dianhydride"), methylnorbornane-2-spiro-α-cyclohexanone-α'-spiro-2"-(methylnorbornane)-5,5",6,6"-tetracarboxylic dianhydride, norbornane-2-spiro-α-cyclopropanone-α'-spiro-2"-norbornane-5,5",6,6"-tetracarboxylic dianhydride, norbornane-2-spiro-α-cyclobutanone-α'-spiro-2"-norbornane-5,5",6,6"-tetracarboxylic dianhydride, norbornane-2-spiro-α-cycloheptanone-α'-spiro-2"-norbornane-5,5",6,6"-tetracarboxylic dianhydride, norbornane-2-spiro-α-cyclooctanone-α'-spiro-2"-norbornane-5,5",6,6"-tetracarboxylic dianhydride, norbornane-2-spiro-α-cyclononanone-α'-spiro-2"-norbornane-5,5",6,6"-tetracarboxylic dianhydride, norbornane-2-spiro-α-cyclodecanone-α'-spiro-2"-norbornane-5,5",6,6"-tetracarboxylic dianhydride, norbornane-2-spiro-α-cycloundecanone-α'-spiro-2"-norbornane-5,5",6,6"-tetracarboxylic dianhydride, norbornane-2-spiro-α-cyclododecanone-α'-spiro-2"-norbornane-5,5",6,6"-tetracarboxylic dianhydride, norbornane-2-spiro-α-cyclotridecanone-α'-spiro-2"-norbornane-5,5",6,6"-tetracarboxylic dianhydride, norbornane-2-spiro-α-cyclotetradecanone-α'-spiro-2"-norbornane-5,5",6,6"-tetracarboxylic dianhydride, norbornane-2-spiro-α-cyclopentadecanone-α'-spiro-2"-norbornane-5,5",6,6"-tetracarboxylic dianhydride, norbornane-2-spiro-α-(methylcyclopentanone)-α'-spiro-2"-norbornane-5,5",6,6"-tetracarboxylic dianhydride, norbornane-2-spiro-α-(methylcyclohexanone)-α'-spiro-2"-norbornane-5,5",6,6"-tetracarboxylic dianhydride, and the like.

From the viewpoint of adjustment of film properties, thermophysical properties, mechanical properties, optical properties, and electrical properties of the cured film formed by using the photosensitive resin composition, the tetracarboxylic dianhydride represented by the formula (a4) preferably contains at least one of a compound (A1-I) represented by the following formula (a1-I):

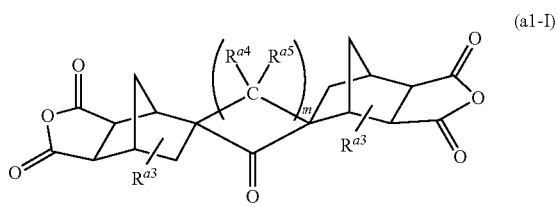

in the formula (a1-I), $R^{a3}$, $R^{a4}$, $R^{a5}$, and n are the same as $R^{a3}$, $R^{a4}$, $R^{a5}$, and n defined in the formula (a2), and
A compound (A1-II) represented by the following formula (a1-II):

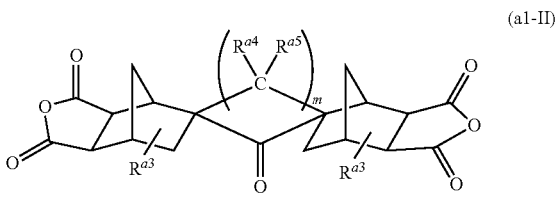

in the formula (a1-II), $R^{a3}$, $R^{a4}$, $R^{a5}$, and n are the same as $R^{a3}$, $R^{a4}$, $R^{a5}$, and n defined in the formula (a2)), and the total amount of compound (A1-I) and compound (A1-II) relative to the total mol number of tetracarboxylic dianhydride is 30 mol % or more.

The compound (A1-I) represented by the formula (a1-I) is an isomer of tetracarboxylic dianhydride represented by the formula (a4) in which two norbornane groups are trans-configurated and a carbonyl group of a cycloalkanone is configured at the end to each of two norbornane groups. The compound (A1-II) represented by the formula (a1-II) is an isomer of tetracarboxylic dianhydride represented by the formula (a4) in which two norbornane groups are cis-configurated and a carbonyl group of a cycloalkanone is configured at the end to each of two norbornane groups. The method for producing a tetracarboxylic dianhydride containing such an isomer at the above ratio is not particularly limited, and a known method can be appropriately employed and, for example, the method mentioned in WO 2014/034760 A may be appropriately employed.

Suitable examples of the unsaturated carboxylic acid ester represented by the formula (a5) include 2-hydroxyethyl acrylate, 2-hydroxyethyl methacrylate, 3-hydroxy-n-propyl acrylate, 3-hydroxy-n-propyl methacrylate, 4-hydroxy-n-butyl acrylate, and 4-hydroxy-n-butyl methacrylate.

A ratio of the amount of the tetracarboxylic dianhydride represented by the formula (a4) to be used to the amount of the unsaturated carboxylic acid ester represented by the formula (a5) to be used is not particularly limited as long as a compound of a desired structure can be synthesized.

The amount of the unsaturated carboxylic acid ester represented by the formula (a5) is preferably 2.0 mol or less, more preferably 0.1 mol or more and 2.0 mol or less, still more preferably 0.5 mol or more and 2.0 mol or less, and particularly preferably 1.0 mol or more 2.0 mol or less, based on 1.0 mol of the tetracarboxylic dianhydride represented by the formula (a4). By using the unsaturated carboxylic acid ester represented by the formula (a5) in such an amount, a compound of a desired structure is easily obtained while preventing excess esterification of carboxy groups.

In the compound represented by the formula (I), which is a compound according to the fourth aspect, $R^{a1}$ and $R^{a2}$ may not be a hydrogen atom or a group represented by the formula (a3), but a saturated aliphatic hydrocarbon group having 1 or more and 20 or less carbon atoms, an aryl group having 6 or more and 20 or less carbon atoms, and an aralkyl group having 7 or more and 20 or less carbon atoms. In such a case, it is possible to obtain a compound of a desired structure represented by the formula (I) by reacting 1.0 mol of a tetracarboxylic dianhydride represented by the formula (a4) with less than 2.0 mol of an unsaturated carboxylic acid ester represented by the formula (a5), followed by reaction with a desired amount of a hydroxyl group-containing compound represented by $R^{a1}$—OH or $R^{a2}$—OH in which $R^{a1}$ or $R^{a2}$ represent a saturated aliphatic hydrocarbon group having 1 or more and 20 or less carbon atoms, an aryl group having 6 or more and 20 or less carbon atoms, or an aralkyl group having 7 or more and 20 or less carbon atoms. It is also possible to obtain a compound of a desired structure represented by the formula (I) by reacting 1.0 mol of a tetracarboxylic dianhydride represented by the formula (a4) with 1.0 mol or less of a hydroxyl group-containing compound represented by $R^{a1}$—OH or $R^{a2}$—OH in which $R^{a1}$ or $R^{a2}$ represent a saturated aliphatic hydrocarbon group having 1 or more and 20 or less carbon atoms, an aryl group having 6 or more and 20 or less carbon atoms, or an aralkyl group having 7 or more and 20 or less carbon atoms, followed by reaction with a desired amount of an unsaturated carboxylic acid ester represented by the formula (a5).

A reaction of a tetracarboxylic dianhydride represented by the formula (a4) with an unsaturated carboxylic acid ester represented by the formula (a5), or a hydroxyl group compound represented by $R^{a1}$—OH or $R^{a2}$—OH is preferably performed in the presence of a catalyst compound which catalyzes ring opening of an acid anhydride group and esterification. Use of such a catalyst enables satisfactory proceeding of an esterification reaction even not under severe conditions where a raw material compound or product undergo pyrolysis. It is possible to use, as the catalyst, for example, an imidazole compound containing an imidazole ring.

It is possible to appropriately select the organic solvent to be used when a compound represented by the formula (I) is synthesized, considering the reaction rate in a synthesis reaction, solubility of the compound, operatability, and the like. The organic solvent is preferably a nitrogen-containing polar organic solvent such as N-methyl-2-pyrrolidone, N,N-dimethylacetamide, N,N-dimethylisobutylamide, N,N-diethylacetamide, N,N-dimethylformamide, N,N-diethylformamide, N-methylcaprolactam, and N,N,N',N'-tetramethylurea.

There is no particular limitation on the temperature at which a tetracarboxylic dianhydride represented by the formula (a4) is reacted with an unsaturated carboxylic acid ester represented by the formula (a5), and the temperature is preferably 0° C. or higher and 80° C. or lower, and more preferably 10° C. or higher and 70° C. or lower. The reaction time is not particularly limited, and preferably 0.5 hour or more and 30 hours or less, and more preferably 1 hour or more and 20 hours or less. When the reaction is performed under these conditions, a compound of a desired structure is easily produced while suppressing gelation due to the side reaction.

EXAMPLES

The present invention will be specifically described below by way of Examples, but the scope of the present invention is not limited to these Examples.

Example 1

(Preparation of Tetracarboxylic Dianhydride)

In accordance with the methods mentioned in Synthesis Example 1, Example 1 and Example 2 of WO 2011/099518 A, a tetracarboxylic dianhydride (norbornane-2-spiro-α-cyclopentanone-α'-spiro-2"-norbornane-5,5",6,6"-tetracarboxylic dianhydride) represented by the following formula was prepared.

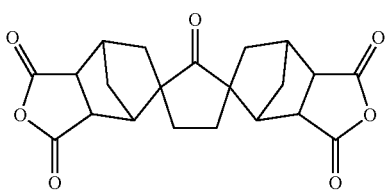 [SMILES: O=C1OC(=O)C2C1C1CC2C2(CCC3(CC4CC3C3C(=O)OC(=O)C43)C2=O)C1]

One part by mol of the tetracarboxylic dianhydride of the above structure, a part by mol of 2-hydroxymethyl methacrylate 1, and 0.03 part by mol of an imidazole compound as a catalyst were charged in N-methyl-2-pyrrolidone so that the solid component concentration became 40% by mass, followed by reaction while stirring under the conditions at 60° C. for 10 hours. After the reaction, the reaction solution was analyzed by HPLC/LC-MS. As a result of LC-MS analysis, the production of a compound corresponding to m/z=550 and a compound corresponding to m/z=662 was confirmed.

m/z=550 corresponds with the molecular weight of a compound of the following structure. The compound of the following structure is also referred to as a monoester. A yield of the monoester was 2.3% based on the charge amount of the tetracarboxylic dianhydride in Example 1.

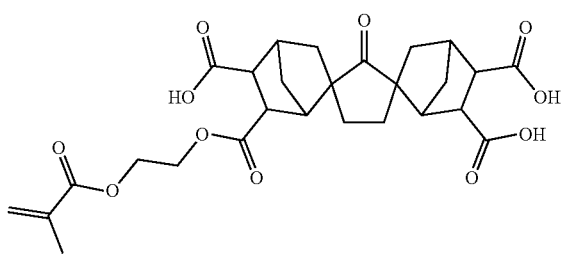 [SMILES: C=C(C)C(=O)OCCOC(=O)C1C(C(=O)O)C2CC1C1(CCC3(CC4CC3C(C(=O)O)C4C(=O)O)C1=O)C2]

m/z=662 corresponds with the molecular weight of a compound of the following structure. The compound of the following structure is also referred to as a diester. A yield of the diester was 95.4% based on the charge amount of the tetracarboxylic dianhydride in Example 1.

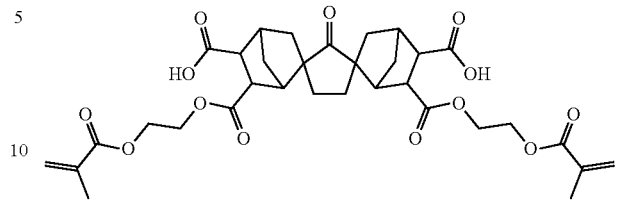

Example 2

First, a reaction vessel made of glass was sufficiently dried by heating. After replacing the atmosphere inside a reaction vessel by nitrogen gas atmosphere, the reaction solution obtained in Example 1 was charged in the reaction vessel. In the reaction vessel, 1.0 part by mol of 4,4'-diaminobenzanilide and 2.0 parts by mol of N,N-dimethyl-4-aminopyridine were charged under the room temperature condition. Part by mol is the value converted when the amount of the diester is 1.0 part by mol. Subsequently, the reaction vessel was cooled to 0° C. under ice bath condition and 2.0 parts by mol of diphenyl (2,3-dihydro-2-thioxo-3-benzooxazolyl)phosphonate was slowly added dropwise while stirring, thereby starting a condensation reaction. The polycondensation reaction was performed under the conditions at 0° C. for 30 minutes, room temperature for 30 minutes, and then 40° C. for 20 hours.

After completion of the reaction, methanol was added to the reaction solution, thereby precipitating a polyamide resin, which was recovered. A yield of the polyamide resin was 95.0% based on the amount of the diester. A weight average molecular weight (Mw) in terms of polystyrene measured by GPC of the resulting polyamide resin was 10,300, and dispersion degree (weight average molecular weight (Mw)/number average molecular weight (Mn)) was 2.50.

Reference Example 1

In the same manner as in Example 1, except that norbornane-2-spiro-α-cyclopentanone-α'-spiro-2"-norbornane-5,5",6,6"-tetracarboxylic dianhydride was changed to 3,3',4,4'-biphenylethertetracarboxylic dianhydride, a mixture of three types of diesters mentioned below was obtained.

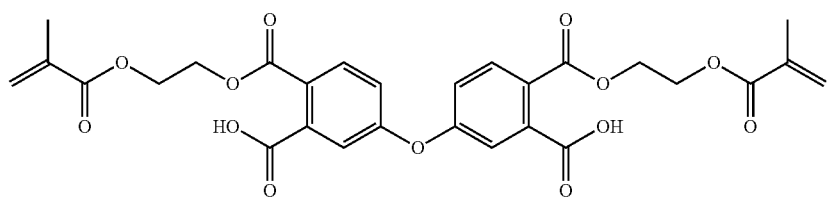

-continued

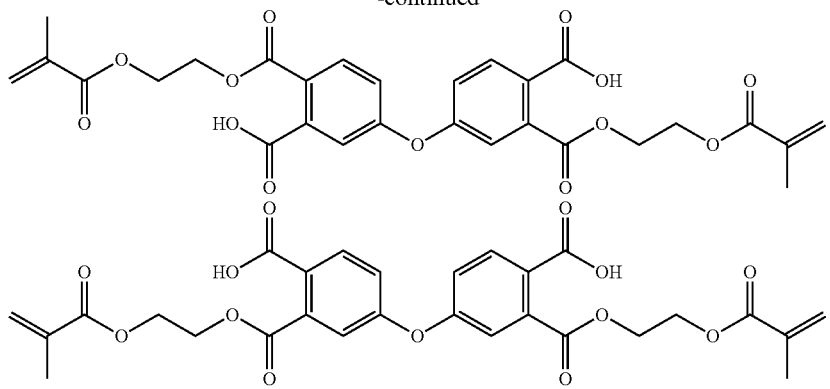

In the same method as in Example 2, except that the diester obtained in the same manner as in Example 1 was changed to the mixture of diesters obtained in Reference Example 1, and 4,4'-diaminobenzanilide was changed to 4,4'-diaminodiphenylether and the reaction conditions were appropriately adjusted, a polyamide resin was obtained. A weight average molecular weight (Mw) in terms of polystyrene measured by GPC of the resulting polyamide resin was 20,000.

Examples 3 to 6 and Comparative Example 1

A hundred parts by mass of a resin (A) of type mentioned in Table 1, 4 parts by mass of the compound mentioned above as a photopolymerization initiator (B), 8 parts by mass of tetraethylene glycol dimethacrylate as a photopolymerizable monomer (C), 4 parts by mass of N,N'-dimethoxymethylurea as a heat crosslinking agent, 4 parts by mass of N-phenyldiethanolamine as a sensitizer, and 1.5 parts by mass of 1,3,5-tris(3-hydroxy-4-tert-butyl-2,6-dimethylbenzyl)-1,3,5-triazine-2,4,6(1H,3H,5H)-trione as an anticorrosive were dissolved in N-methyl-2-pyrrolidone so that the solid component concentration became 25% by mass to obtain photosensitive resin compositions of Examples 3 to 6 and Comparative Example 1.

As the resin (A), the following PA1 to PA5 each being a polyamide resin were used. The weight average molecular weight of PA1 to PA4 was adjusted by finely adjusting the temperature, stirring conditions and time of the condensation reaction.

PA1: Polyamide resin (weight average molecular weight 11,000) obtained by condensing 4,4'-diaminobenzanilide in an equimolar ratio in terms of diester, using the reaction solution obtained by the method of Example 1

PA2: Polyamide resin (weight average molecular weight 10,000) obtained by condensing 4,4'-diamino-2,2'-bis(trifluoromethyl)biphenyl in an equimolar ratio in terms of diester, using the reaction solution obtained by the method of Example 1

PA3: Polyamide resin (weight average molecular weight 15,000) obtained by condensing 4,4'-diaminodiphenylether in an equimolar ratio in terms of diester, using the reaction solution obtained by the method of Example 1

PA4: Polyamide resin (weight average molecular weight 12,000) obtained by condensing 2,2-bis(3-amino-4-hydroxyphenyl)hexafluoropropene in an equimolar ratio in terms of diester, using the reaction solution obtained by the method of Example 1

PA5: Polyamide resin including a skeleton derived from 3,3',4,4'-biphenylethertetracarboxylic dianhydride (weight average molecular weight 20,000) obtained in Reference Example 1

A compound having the following structure was used as the photopolymerization initiator (B).

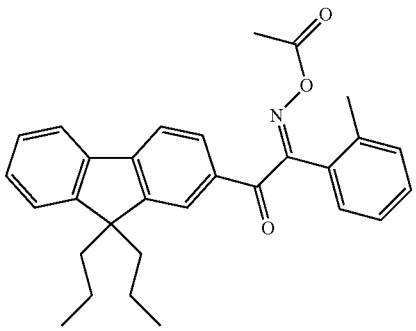 [SMILES: CCCC1(CCC)c2ccccc2-c2ccc(C(=O)/C(=N/OC(C)=O)c3ccccc3C)cc21]

Using the resulting photosensitive resin composition, pattern detachment and transparency of the thus formed film were evaluated in accordance with the following method. These evaluation results are shown in Table 1.

(Evaluation of Pattern Detachment)

Each of photosensitive resin compositions of Examples and Comparative Example was applied on a glass substrate, followed by baking at 90° C. for 120 seconds to obtain a coating film having a thickness of 10 μm. The thus formed coating film was exposed through a negative mask at light exposure 100 mJ/cm$^2$ so as to form a line pattern with a line width of 5 μm, using a mirror projection aligner (product name: MPA-600FA, manufactured by Canon Inc.). After exposure, development was performed under the conditions at 23° C. for 60 seconds, using cyclopentanone as a developing solution. The line pattern with a line width of 5 μm obtained after the development was observed by a microscope, and then it was evaluated whether pattern detachment occurred. The case where pattern detachment was observed was rated "Poor", while the case where no pattern detachment was observed was rated "Good".

(Evaluation of Transparency)

In the same manner as in the evaluation of pattern detachment, except that the entire surface of the coating film was exposed, a cured film of a photosensitive resin composition was obtained. The resulting cured film was baked under nitrogen atmosphere at 300° C. for 2 hours. A light transmittance of the cured film after baking was measured, and then the transparency of the cured film was evaluated according to the following criteria.

"Excellent": Transmittance of light in the entire wavelength region of 380 nm or more and 780 nm or less is 90% or more.

"Good": Transmittance of light in the entire wavelength region of 380 nm or more and 780 nm or less is 80% or more.

"Poor": Transmittance of light in the entire wavelength region of 380 nm or more and 780 nm or less is less than 80%.

TABLE 1

| | Resin (A) | | |
|---|---|---|---|
| Type | Weight average molecular weight | Pattern detachment | Transparency |
| Ex. 3 | PA1 | 11,000 | Good | Good |
| Ex. 4 | PA2 | 10,000 | Good | Excellent |
| Ex. 5 | PA3 | 15,000 | Good | Good |
| Ex. 6 | PA4 | 12,000 | Good | Excellent |
| Comp. Ex. 1 | PA5 | 20,000 | Poor | Poor |

As is apparent from a comparison between Examples 3 to 6 and Comparative Example 1, a structural unit derived from an alicyclic tetracarboxylic dianhydride of a specific structure is included as a mother nucleus of a polyamide resin, whereby, the resulting cured film satisfactorily adheres to substrates and is excellent in transparency.

Examples 7 to 9

A hundred parts by mass of a resin (A) of type mentioned in Table 2, 4 parts by mass of the compound mentioned above as a photopolymerization initiator (B), 8 parts by mass of tetraethylene glycol dimethacrylate as a photopolymerizable monomer (C), 4 parts by mass of N,N'-dimethoxymethylurea as a heat crosslinking agent, 4 parts by mass of N-phenyldiethanolamine as a sensitizer, and 1.5 parts by mass of 1,3,5-tris(3-hydroxy-4-tert-butyl-2,6-dimethylbenzyl)-1,3,5-triazine-2,4,6(1H,3H,5H)-trione as an anticorrosive were dissolved in N-methyl-2-pyrrolidone so that the solid component concentration became 25% by mass to obtain photosensitive resin compositions of Examples 7 to 9.

Among resins mentioned in Table 2, PA4 is as mentioned above. PA6 and PA7 are as mentioned below. PA6: Polyamide resin (weight average molecular weight 19,000) obtained by condensing 3,3'-dihydroxy-4,4'-diaminobiphenyl in an equimolar ratio in terms of diester, using the reaction solution obtained by the method of Example 1

PA7: Polyamide resin (weight average molecular weight 19,500) obtained by condensing 2,2-bis(3-hydroxy-4-aminophenyl)propane in an equimolar ratio in terms of diester, using the reaction solution obtained by the method of Example 1

The evaluation method of pattern detachment and the evaluation method of a transmittance in Examples 7 to 9 are the same as in Examples 3 to 6, except for the development method. In Examples 7 to 9, the development with an aqueous solution having the concentration of 2.38% by mass of tetramethylammonium hydroxide was performed in place of the development with cyclopentanone in Examples 3 to 6. The evaluation results of pattern detachment and the evaluation results of a transmittance with respect to the photosensitive resin compositions of Examples 7 to 9 are shown in Table 2.

TABLE 2

| | Resin (A) | | |
|---|---|---|---|
| Type | Weight average molecular weight | Pattern detachment | Transparency |
| Ex. 7 | PA4 | 12,000 | Good | Good |
| Ex. 8 | PA6 | 19,000 | Good | Excellent |
| Ex. 9 | PA7 | 19,500 | Good | Good |

As is apparent from Examples 3 to 6 and Examples 7 to 9, a structural unit derived from an alicyclic tetracarboxylic dianhydride of a specific structure is included as a mother nucleus of a polyamide resin, whereby, the resulting cured film satisfactorily adheres to substrates and is excellent in transparency even if the development method is a method of development with an organic solvent, or a method of development with an alkali developing solution.

What is claimed is:

1. A photosensitive resin composition comprising a resin (A) and a photopolymerization initiator (B), wherein the resin (A) is a polyamide resin including a structural unit represented by the following formula (a1):

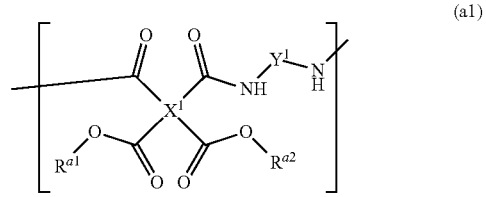

(a1)

wherein, in the formula (a1), $X^1$ is a tetravalent group represented by the following formula (a2):

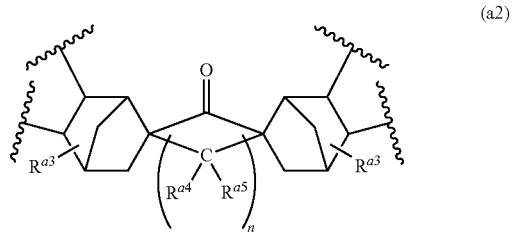

(a2)

$Y^1$ is a divalent organic group,
$R^{a1}$ and $R^{a2}$ each independently represents a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

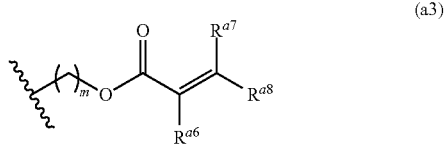

(a3)

at least one of $R^{a1}$ and $R^{a2}$ is a group represented by the above formula (a3), in the formula (a2), $R^{a3}$, $R^{a4}$, and $R^{a5}$ each independently represents one selected from the group consisting of a hydrogen atom, an alkyl group having 1 or more and 10 or less carbon atoms, and a fluorine atom, n is an integer of 0 or more and 12 or less, in the above formula (a3), $R^{a6}$, $R^{a7}$, and $R^{a8}$ each independently represents a hydrogen atom or an organic group having 1 or more and 3 or less carbon atoms, and m is an integer of 2 or more and 10 or less.

2. The photosensitive resin composition according to claim 1, wherein the polyamide resin is a condensate of a polyvalent carboxylic acid compound represented by the following formula (I):

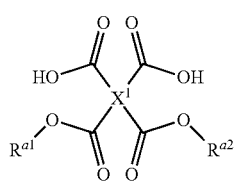

(I)

wherein, in the formula (I), $X^1$ is $R^{a1}$, and $R^{a2}$ is the same as defined in the formula (a1), and/or an acid halide of the polyvalent carboxylic acid compound with a diamine compound represented by the following formula (II):

$H_2N—Y^1—NH_2$ (II)

wherein, in the formula (II), $Y^1$ is as the same as defined in the formula (a1).

3. The photosensitive resin composition according to claim 1, further comprising a photopolymerizable monomer (C).

4. The photosensitive resin composition according to claim 1, wherein the polyamide resin has a weight average molecular weight of 50,000 or less.

5. A method for producing a cured film, the method comprising:
applying the photosensitive resin composition according to claim 1 to form a coating film; and
exposing the coating film to an active energy ray.

6. The method for producing a cured film according to claim 5, wherein exposure of the coating film is regioselectively performed, and the method further comprises developing the exposed coating film.

7. A cured film which is obtained by curing the photosensitive resin composition according to claim 1.

8. A polyamide resin comprising a structural unit represented by the following formula (a1):

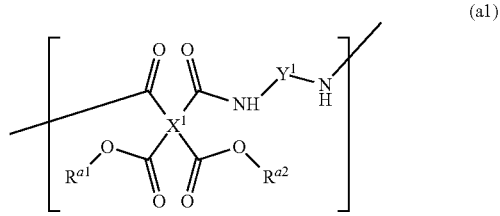

(a1)

wherein, in the formula (a1), $X^1$ is a tetravalent group represented by the following formula (a2):

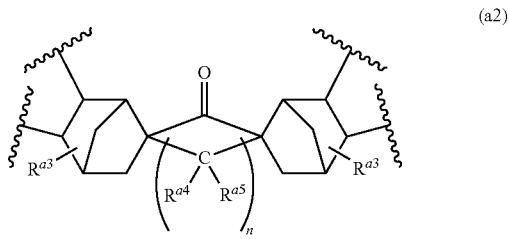

(a2)

$Y^1$ is a divalent organic group, $R^{a1}$ and $R^{a2}$ each independently represents a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

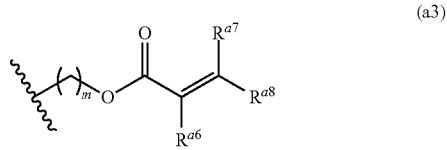

(a3)

at least one of $R^{a1}$ and $R^{a2}$ is a group represented by the formula (a3), in the above formula (a2), $R^{a3}$, $R^{a4}$, and $R^{a5}$ each independently represents one selected from the group consisting of a hydrogen atom, an alkyl group having 1 or more and 10 or less carbon atoms, and a fluorine atom, n is an integer of 0 or more and 12 or less, in the above formula (a3), $R^{a6}$, $R^{a7}$, and $R^{a8}$ each independently represents a hydrogen atom or an organic group having 1 or more and 3 or less carbon atoms, m is an integer of 2 or more and 10 or less, wherein —COOR$^{a1}$ or —COOR$^{a2}$ of the structural unit (a1) may be replaced with —COX$^{a1}$ or —COX$^{a2}$, respectively, wherein X$^{a1}$ and X$^{a2}$ are halogen atoms, to form an acid halide, or —COOR$^{a1}$ or —COOR$^{a2}$ of the structural unit (a1) may be replaced with —COOY$^{a1}$ or —COOY$^{a2}$, respectively, wherein Y$^{a1}$ and Y$^{a2}$ are cations, to form a carboxylate salt.

9. The polyamide resin according to claim 8, which is a condensate of a polyvalent carboxylic acid compound represented by the following formula (I):

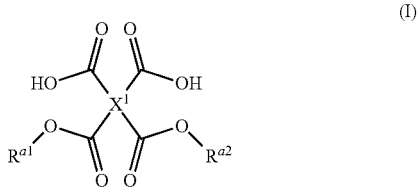

(I)

wherein, in the formula (I), $X^1$, $R^{a1}$, and $R^{a2}$ are the same as defined in the formula (a1), wherein —COOR$^{a1}$ or —COOR$^{a2}$ of the polyhydric carboxylic acid compound (I) may be replaced with —COX$^{a1}$ or —COX$^{a2}$, respectively, wherein X$^{a1}$ and X$^{a2}$ are halogen atoms, to form an acid halide, or —COOR$^{a1}$ or —COOR$^{a2}$ of the polyhydric carboxylic acid compound (I) may be replaced with —COOY$^{a1}$ or —COOY$^{a2}$, respectively, wherein Y$^{a1}$ and Y$^{a2}$ are cations, to form a carboxylate salt, and a diamine compound represented by the following formula (II):

$$H_2N—Y^1—NH_2 \quad (II)$$

wherein, in the formula (II), Y$^1$ is the same as defined in the formula (a1).

10. The polyamide resin according to claim 8, wherein the weight average molecular weight is 50,000 or less.

11. A method for producing the polyamide resin according to claim 8, the method comprising condensing a polyvalent carboxylic acid compound represented by the following formula (I):

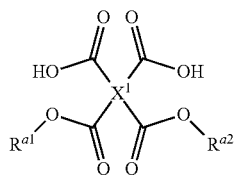

wherein, in the formula (I), X$^1$ is a tetravalent group represented by the following formula (a2):

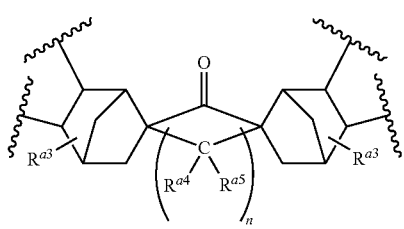

R$^{a1}$ and R$^{a2}$ each independently represents a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

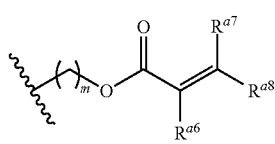

at least one of R$^{a1}$ and R$^{a2}$ is a group represented by the formula (a3), in the formula (a2), R$^{a3}$, R$^{a4}$, R$^{a5}$ each independently represents one selected from the group consisting of a hydrogen atom, an alkyl group having 1 or more and 10 or less carbon atoms, and a fluorine atom, n is an integer of 0 or more and 12 or less, in the formula (a3), R$^{a6}$, R$^{a7}$, and R$^{a8}$ each independently represents a hydrogen atom or an organic group having 1 or more and 3 or less carbon atoms, m is an integer of 2 or more and 10 or less, and/or an acid halide of the polyvalent carboxylic acid compound, with a diamine compound represented by the following formula (II):

$$H_2N—Y^1—NH_2 \quad (II)$$

wherein, in the formula (II), Y$^1$ is a divalent organic group.

12. A compound represented by the following formula (I):

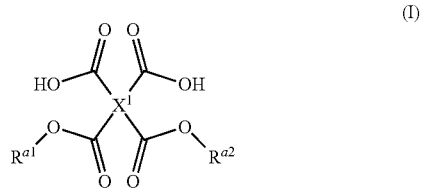

wherein, in the formula (I) X$^1$ is a tetravalent group represented by the following formula (a2):

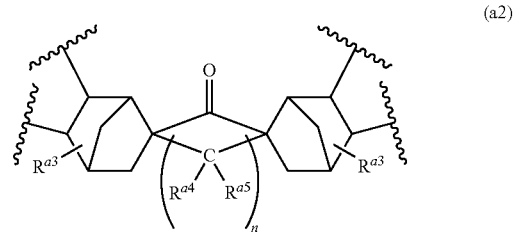

R$^{a1}$ and R$^{a2}$ each independently represents a hydrogen atom, a saturated aliphatic hydrocarbon group having 1 or more and 20 or less carbon atoms, an aryl group having 6 or more and 20 or less carbon atoms, an aralkyl group having 7 or more and 20 or less carbon atoms, or a group represented by the following formula (a3):

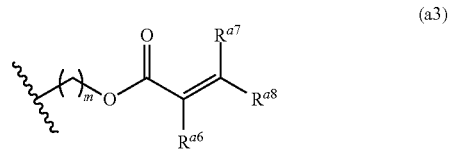

at least one of R$^{a1}$ and R$^{a2}$ is a group represented by the formula (a3), in the formula (a2), R$^{a3}$, R$^{a4}$, and R$^{a5}$ each independently represents one selected from the group consisting of a hydrogen atom, an alkyl group having 1 or more and 10 or less carbon atoms, and a fluorine atom, n is an integer of 0 or more and 12 or less, in the formula (a3), R$^{a6}$, R$^{a7}$, and R$^{a8}$ each independently represents a hydrogen atom or an organic group having 1 or more and 3 or less carbon atoms, m is an integer of 2 or more and 10 or less, and a carboxy group contained in the compound may form an acid halide, or may form a salt.

13. A method for producing the compound according to claim 12, the method comprising reacting a tetracarboxylic dianhydride represented by the following formula (a4):

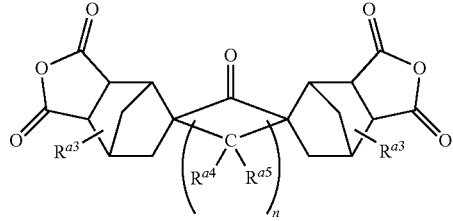

(a4)

wherein, in the formula (a4), $R^{a3}R^{a4}$, and $R^{a5}$ each independently represents one selected from the group consisting of a hydrogen atom, an alkyl group having 1 or more and 10 or less carbon atoms, and a fluorine atom, n is an integer of 0 or more and 12 or less, with an unsaturated carboxylic acid ester represented by: the following formula (a5):

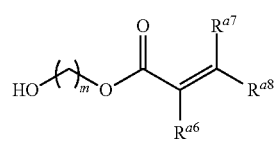

(a5)

wherein, in the formula (a5), $R^{a6}$, $R^{a7}$, and $R^{a8}$ each independently represents a hydrogen atom or an organic group having 1 or more and 3 or less carbon atoms, and m is an integer of 2 or more and 10 or less.

* * * * *